US012790624B2

(12) United States Patent
Saxena et al.

(10) Patent No.: US 12,790,624 B2
(45) Date of Patent: Nov. 10, 2026

(54) METHODS OF GENOTYPING ADENO-ASSOCIATED VIRUS INVERTED TERMINAL REPEAT SEQUENCES IN PLASMIDS USING FIXED FLANKING SEQUENCE MARKER-BASED EXTRACTION AND CLUSTERING

(71) Applicants: Regeneron Pharmaceuticals, Inc., Tarrytown, NY (US); Intellia Therapeutics, Inc., Cambridge, MA (US)

(72) Inventors: Ayush Saxena, Tarrytown, NY (US); Rong-sen Calvin Chen, Tarrytown, NY (US)

(73) Assignee: Intellia Therapeutics, Inc., Cambridge, MA (US)

( * ) Notice: Subject to any disclaimer, the term of this patent is extended or adjusted under 35 U.S.C. 154(b) by 32 days.

(21) Appl. No.: 18/742,805

(22) Filed: Jun. 13, 2024

(65) Prior Publication Data

US 2024/0417752 A1 Dec. 19, 2024

Related U.S. Application Data

(60) Provisional application No. 63/507,918, filed on Jun. 13, 2023.

(51) Int. Cl.
*C12N 15/86* (2006.01)
*C12Q 1/6869* (2018.01)

(52) U.S. Cl.
CPC ........... *C12N 15/86* (2013.01); *C12Q 1/6869* (2013.01); *C12N 2750/14143* (2013.01); *C12N 2750/14151* (2013.01)

(58) Field of Classification Search
None
See application file for complete search history.

(56) References Cited

FOREIGN PATENT DOCUMENTS

CN 113517024 A 10/2021

OTHER PUBLICATIONS

Carr et al., "Palidis: fast discovery of novel insertion sequences," Microbial Genomics, vol. 9:000917, 2023, pp. 1-9.
International Search Report and Written Opinion based on related application No. PCT/US2024/033872 mailed Dec. 13, 2024.

*Primary Examiner* — G. Steven Vanni
(74) *Attorney, Agent, or Firm* — Ballard Spahr LLP

(57) ABSTRACT

Disclosed are data pipelines for string extraction, clustering, and comparison. A method may include extracting, from each plasmid genome sequence sequenced from genomes of plasmids, based on the presence of fixed flanking sequence markers (FFSMs) in the plasmid genome sequence, sequence regions. Each sequence region is within the FFSMs and includes a candidate inverted terminal repeat (ITR) sequence. The example method further includes clustering, based on perfect sequence identity, two or more sequence regions of the sequence regions to generate a clusters, merging, based on an alignment between their corresponding sequence regions, two or more clusters of the clusters; when a single cluster remains, identifying, based on a local alignment, a genotype of a candidate ITR sequence of the single cluster, and manufacturing, based on the genotype of the candidate ITR sequence, a plurality of AAV vectors using plasmids having ITR sequences with the genotype of the candidate ITR sequence.

25 Claims, 31 Drawing Sheets

Specification includes a Sequence Listing.

1800

SEQUENCE LISTING

```
Sequence total quantity: 3
SEQ ID NO: 1           moltype = DNA  length = 145
FEATURE                Location/Qualifiers
source                 1..145
                       mol_type = other DNA
                       organism = synthetic construct
SEQUENCE: 1
aggaacccct agtgatggag ttggccactc cctctctgcg cgctcgctcg ctcactgagg  60
ccgcccgggc aaagcccggg cgtcgggcga cctttggtcg cccggcctca gtgagcgagc  120
gagcgcgcag agagggagtg gccaa                                        145

SEQ ID NO: 2           moltype = DNA  length = 145
FEATURE                Location/Qualifiers
source                 1..145
                       mol_type = other DNA
                       organism = synthetic construct
SEQUENCE: 2
aggaacccct agtgatggag ttggccactc cctctctgcg cgctcgctcg ctcactgagg  60
ccgggcgacc aaaggtcgcc cgacgcccgg gctttgcccg ggcggcctca gtgagcgagc  120
gagcgcgcag agagggagtg gccaa                                        145

SEQ ID NO: 3           moltype = DNA  length = 57
FEATURE                Location/Qualifiers
source                 1..57
                       mol_type = other DNA
                       organism = synthetic construct
SEQUENCE: 3
ctgaggccgg gcgaccaaag gtcgcccgac gcccgggctt tgcccgggcg gcctcag     57
```

METHODS OF GENOTYPING ADENO-ASSOCIATED VIRUS INVERTED TERMINAL REPEAT SEQUENCES IN PLASMIDS USING FIXED FLANKING SEQUENCE MARKER-BASED EXTRACTION AND CLUSTERING

CROSS REFERENCE TO RELATED PATENT APPLICATION

This application claims priority to U.S. Provisional Application No. 63/507,918 filed Jun. 13, 2023, herein incorporated by reference in its entirety.

REFERENCE TO SEQUENCE LISTING

The Sequence Listing submitted Aug. 6, 2024 as a text file named "37595.0044U2.xml," created on Aug. 5, 2024, and having a size of 3964 bytes is hereby incorporated by reference pursuant to 37 C.F.R. § 1.52(e)(5).

BACKGROUND

Adeno-associated viruses (AAVs) are small, non-enveloped viruses that belong to the Parvoviridae family. AAVs are known for their ability to infect both dividing and non-dividing cells and are not currently associated with any disease. These characteristics make AAVs attractive candidates for use as vectors in gene therapy applications.

Gene therapy is a technique to treat or prevent disease by inserting a gene into a patient's cells. Gene therapy includes, for example, replacing a mutated gene that causes disease with a healthy copy of the gene, inactivating, or "knocking out," a mutated gene that is functioning improperly, and introducing a new gene to help fight a disease.

In the context of gene therapy, a vector is a vehicle for delivering therapeutic genes to a patient's cells. The use of AAVs as vectors in gene therapy has been widely studied due to their ability to deliver genes to a wide range of tissues and their low immunogenicity. AAV vectors are created by removing the viral genes and replacing them with the therapeutic gene of interest. The resulting recombinant AAV (rAAV) vectors are then used to deliver the therapeutic gene to the patient's cells.

The AAV genome is composed of a single-stranded DNA molecule flanked by inverted terminal repeats (ITRs). ITRs are sequences of DNA that are the same when read in the 5' to 3' direction on one strand and the 3' to 5' direction on the complementary strand. These sequences play a role in the replication, packaging, and integration of the AAV genome. The ITRs are the sole cis-acting elements retained in the rAAV vector genome, serving as the origin of replication and packaging signal for the virus. The genotype of the ITRs can influence the efficiency of the vector in delivering the therapeutic gene to the patient's cells. Therefore, identifying the genotypes of ITRs is an integral part of manufacturing AAV vectors for gene therapy applications.

SUMMARY

Disclosed are methods and systems comprising sequencing genomes of a plurality of plasmids to obtain a plurality of plasmid genome sequences; receiving a specification of a fixed flanking sequence marker; extracting, from each plasmid genome sequence, based on the presence of the fixed flanking sequence markers in the plasmid genome sequence, a plurality of sequence regions, wherein each sequence region is within the fixed flanking sequence markers and comprises a candidate inverted terminal repeat (ITR) sequence; clustering, based on perfect sequence identity, two or more sequence regions of the plurality of sequence regions to generate a plurality of clusters; merging, based on an alignment between their corresponding sequence regions, two or more clusters of the plurality of clusters; when a single cluster remains, identifying, based on a local alignment, a genotype of a candidate ITR sequence of the single cluster; and manufacturing, based on the genotype of the candidate ITR sequence, a plurality of AAV vectors using plasmids having ITR sequences with the genotype of the candidate ITR sequence.

Disclosed are methods and systems comprising sequencing genomes of a plurality of plasmids to obtain a plurality of plasmid genome sequences; receiving a specification of a fixed flanking sequence marker; extracting, from each plasmid genome sequence, based on the presence of the fixed flanking sequence marker in that plasmid genome sequence, a plurality of sequence regions, wherein each sequence region is within the fixed flanking sequence markers and comprises a candidate inverted terminal repeat (ITR) sequence; clustering, based on sequence identity, two or more sequence regions of the plurality of sequence regions to generate a plurality of clusters; merging, based on an alignment between their corresponding sequence regions, two or more clusters of the plurality of clusters; and deeming, based on two or more clusters remaining after the merging, the plurality of plasmids unsuitable for production of recombinant vector genomes.

Disclosed are methods and systems comprising sequencing genomes of a plurality of plasmids to obtain a plurality of plasmid genome sequences; receiving a specification of a fixed flanking sequence marker; extracting, from each plasmid genome sequence, based on the presence of the fixed flanking sequence markers in that plasmid genome sequence, a plurality of sequence regions, wherein each sequence region is within the fixed flanking sequence markers and comprises a candidate inverted terminal repeat (ITR) sequence; clustering, based on sequence identity, two or more sequence regions of the plurality of sequence regions to generate a plurality of clusters; merging, based on an alignment between their corresponding sequence regions, two or more clusters of the plurality of clusters; and when a single cluster remains after said merging, identifying, based on a local alignment, a genotype of a candidate ITR sequence of a representative sequence region of the single cluster.

Disclosed are methods and systems comprising sequencing Adeno-associated virus (AAV) vector genomes, from a plurality of AAV vectors, to obtain a plurality of AAV vector genome sequences; receiving a specification of a fixed flanking sequence marker; extracting, from each AAV vector genome sequence of the plurality of AAV vectors, based on the presence of the fixed flanking sequence markers in that AAV vector genome sequence, a sequence region immediately to the left or immediately to the right of a fixed flanking sequence marker, wherein the sequence region comprises a candidate ITR sequence; clustering, based on perfect sequence identity, two or more sequence regions of the plurality of sequence regions to generate a plurality of clusters; merging, based on an alignment between their corresponding sequence regions, two or more clusters of the plurality of clusters; and deeming, based on two or more clusters remaining after the merging, the plurality of AAV vector genomes as unsuitable.

Disclosed are methods and systems comprising sequencing a plurality of Adeno-associated viral (AAV) vector genomes to obtain a plurality of AAV vector genome sequences; receiving a specification of a fixed flanking sequence marker; extracting, from each AAV vector genome sequence of the plurality of AAV vectors, based on the presence of the fixed flanking sequence markers in that AAV vector genome sequence, a sequence region immediately to the left or immediately to the right of a fixed flanking sequence marker, wherein the sequence region comprises a candidate ITR sequence; clustering, based on perfect sequence identity, two or more sequence regions of the plurality of sequence regions to generate a plurality of clusters; merging, based on an alignment between their corresponding sequence regions, two or more clusters of the plurality of clusters to generate a modified plurality of clusters; and when a single cluster remains after said merging, identifying, based on a local alignment, a genotype of a candidate ITR sequence of a representative sequence region of the single cluster.

Disclosed are methods of treating a subject in need thereof comprising administering to the subject a therapeutically effective amount of an Adeno-associated virus (AAV) vector comprising a vector genome encapsulated by an AAV capsid, wherein the AAV genome comprises at least two AAV inverted terminal repeats (ITR), a nucleic acid sequence encoding a therapeutic, wherein a genotype of the at least two AAV ITRs is identical to a reference AAV ITR as determined based on the methods disclosed herein.

Additional advantages of the disclosed method and compositions will be set forth in part in the description which follows, and in part will be understood from the description, or may be learned by practice of the disclosed method and compositions. The advantages of the disclosed method and compositions will be realized and attained by means of the elements and combinations particularly pointed out in the appended claims. It is to be understood that both the foregoing general description and the following detailed description are exemplary and explanatory only and are not restrictive of the invention as claimed.

BRIEF DESCRIPTION OF THE DRAWINGS

The accompanying drawings, which are incorporated in and constitute a part of this specification, illustrate several embodiments of the disclosed method and compositions and together with the description, serve to explain the principles of the disclosed methods and systems:

FIG. 2A shows SEQ ID NO:1 (Flip) and SEQ ID NO:2 (Flop).

FIG. 12 shows SEQ ID NO:1 (Flip) and SEQ ID NO:2 (Flop).

FIG. 13 shows SEQ ID NO:1 (Flip) and SEQ ID NO:2 (Flop).

FIG. 14 shows SEQ ID NO:15 (Flip) and SEQ ID NO:2 (Flop).

FIG. 12 shows SEQ ID NO:1 (Flip) and SEQ ID NO:2 (Flop).

DETAILED DESCRIPTION

Figure 1:
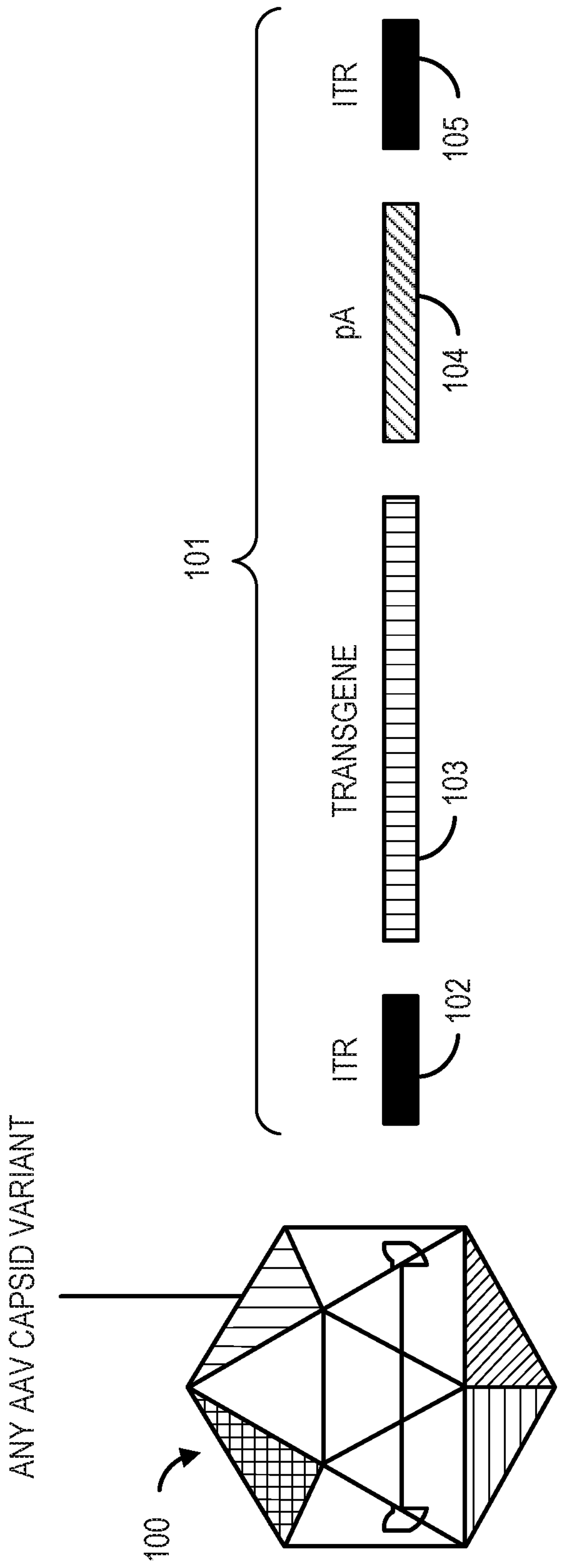
FIG. 1 shows an example diagram of an AAV vector.

The disclosed methods and compositions may be understood more readily by reference to the following detailed description of particular embodiments and the Example included therein and to the Figures and their previous and following description.

A. Definitions

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described herein. It is understood that the disclosed method and compositions are not limited to the particular methodology, protocols, and reagents described as these may vary. It is also to be understood that the terminology used herein is for the purpose of describing particular embodiments only, and is not intended to limit the scope of the present invention which will be limited only by the appended claims.

As used herein, "adapter," or "sequencing adapter" refers to short nucleic acids (e.g., less than about 500, less than about 100, less than about 50 nucleotides, between 20-30 nucleotides in length) that are typically at least partially double-stranded and used to link to either or both ends of a given sample nucleic acid molecule. Adapters can include nucleic acid primer binding sites to permit amplification of a nucleic acid molecule flanked by adapters at both ends, and/or a sequencing primer binding site, including primer binding sites for sequencing applications, such as various next generation sequencing (NGS) applications. Adapters can also include binding sites for capture probes, such as an oligonucleotide attached to a flow cell support or the like. Adapters can also include a nucleic acid tag as described herein. Nucleic acid tags are typically positioned relative to amplification primer and sequencing primer binding sites, such that a nucleic acid tag is included in amplicons and sequencing reads of a given nucleic acid molecule. Adapters of the same or different sequence can be linked to the respective ends of a nucleic acid molecule. In certain embodiments, the same adapter is linked to the respective ends of the nucleic acid molecule except that the nucleic acid tag differs in its sequence. In some embodiments, the adapter is a Y-shaped adapter in which one end is blunt ended or tailed as described herein, for joining to a nucleic acid molecule, which is also blunt ended or tailed with one or more complementary nucleotides. In still other exemplary embodiments, an adapter is a bell-shaped adapter that includes a blunt or tailed end for joining to a nucleic acid molecule to be analyzed. Other exemplary adapters include T-tailed and C-tailed adapters.

As used herein, "administer" or "administering" a therapeutic agent (e.g., an immunological therapeutic agent, a DNA damage response (DDR) inhibitor (e.g., a poly (ADP-ribose) polymerase (PARP) inhibitor (PARPi)), an adeno-associated virus (AAV), a liquid nanoparticle (LNP), etc.) to a subject means to give, apply or bring the composition into contact with the subject. Administration can be accomplished by any of a number of routes, including, for example, topical, oral, subcutaneous, intramuscular, intraperitoneal, intravenous, intrathecal, and/or intradermal.

As used herein, "align," alignment," "aligning," "map," and "mapping" in the context of nucleic acids refers to arranging sequences of DNA or RNA to identify regions of similarity. Similarity may be related to the nucleotide sequence, structural, functional, and/or evolutionary relationships between the sequences. Alignment of DNA or RNA sequences involves alignment of DNA or RNA of one sequence to DNA or RNA of at least one other sequence. Such alignment may exclude non-genomic DNA or non-transcript RNA, such as a molecular barcode, padding bases, and the like. For example, DNA of a sequence read may be aligned to genomic DNA of a reference DNA sequence, excluding any molecular tag or adapter sequence that may be attached to the sequence read. Alignment may be performed using any number of tools, including but not limited to, BLAST, BLASR, BWA-MEM, DAMAPPER, NGMLR, GraphMap, Minimap, among others.

Throughout the description and claims of this specification, the word "comprise" and variations of the word, such as "comprising" and "comprises," means "including but not limited to," and is not intended to exclude, for example, other additives, components, integers or steps. In particular, in methods stated as comprising one or more steps or operations it is specifically contemplated that each step comprises what is listed (unless that step includes a limiting term such as "consisting of"), meaning that each step is not intended to exclude, for example, other additives, components, integers or steps that are not listed in the step.

As used herein, recitation that nucleotides "correspond to" nucleotides in a sequence refers to nucleotides identified upon alignment with the sequence to maximize identity using an alignment method, such as any method based on Smith-Waterman or a related method.

Gene therapy involves the modification (e.g., addition, substitution, removal, etc. . . . ) of genetic material of host cells with the goal of treating or curing disease. One approach for correcting faulty gene expression is to insert a normal gene (transgene) into a specific location within the genome to replace a nonfunctional or defective, disease-causing gene. Gene therapy can also be used as a platform for the delivery of a therapeutic protein or RNA to treat various diseases so that the therapeutic product is expressed for a prolonged period of time, eliminating the need for repeat dosing. A carrier molecule called a vector must be used to deliver a transgene to the patient's target cells, the most common vector being a virus that has been genetically altered to carry normal human genes. Viruses have evolved a way of encapsulating and delivering their genes to human cells in a pathogenic manner and thus, virus genomes can be manipulated to insert therapeutic genes. Stable transgene expression can be achieved following in vivo delivery of vectors based on adenoviruses or adeno-associated viruses (AAVs) into non-dividing cells, and also by transplantation of stem cells transduced ex vivo with integrating and non-integrating vectors, such as those based on retroviruses and lentiviruses.

The term "DNA (deoxyribonucleic acid)" refers to a chain of nucleotides comprising deoxyribonucleosides that each comprise one of four nucleobases, namely, adenine (A), thymine (T), cytosine (C), and guanine (G). The term "RNA (ribonucleic acid)" refers to a chain of nucleotides comprising four types of ribonucleosides that each comprise one of four nucleobases, namely; A, uracil (U), G, and C. Certain pairs of nucleotides specifically bind to one another in a complementary fashion (called complementary base pairing). In DNA, adenine (A) pairs with thymine (T) and cytosine (C) pairs with guanine (G). In RNA, adenine (A) pairs with uracil (U) and cytosine (C) pairs with guanine (G). When a first nucleic acid strand binds to a second nucleic acid strand made up of nucleotides that are complementary to those in the first strand, the two strands bind to form a double strand. As used herein, "nucleic acid sequencing data," "nucleic acid sequencing information," "nucleic acid sequence," "nucleotide sequence", "genomic sequence," "genetic sequence," or "fragment sequence," or "nucleic acid sequencing read" denotes any information or data that is indicative of the order of the nucleotide bases (e.g., adenine, guanine, cytosine, and thymine or uracil) in a molecule (e.g., a whole genome, whole transcriptome, exome, oligonucleotide, polynucleotide, or fragment) of a nucleic acid such as DNA or RNA. It should be understood that the present teachings contemplate sequence information obtained using all available varieties of techniques, platforms or technologies, including, but not limited to: capillary electrophoresis, microarrays, ligation-based systems, polymerase-based systems, hybridization-based systems, direct or indirect nucleotide identification systems, pyrosequencing, ion- or pH-based detection systems, and electronic signature-based systems.

"Exemplary" means "an example of" and is not intended to convey an indication of a preferred or ideal configuration. "Such as" is not used in a restrictive sense, but for explanatory purposes.

A nucleic acid sequence may be eukaryotic in origin. In this regard, eukaryotic genes are comprised of "exons" and "introns." The term "exon," as used herein, refers to a nucleic acid sequence present in a gene which is represented in the mature form of an RNA molecule after excision of introns during transcription. Exons are translated into protein. The term "intron," as used herein, refers to a nucleic acid sequence present in a given gene which is not translated into protein and is generally found between exons. During transcription, introns are removed from precursor messenger RNA (pre-mRNA), and exons are joined via RNA splicing. Thus, in an embodiment, a nucleic acid sequence may comprise one or more exons and introns. The term "transcription," as used herein, is the process of creating an equivalent RNA copy of a sequence of DNA, and involves the steps of initiation, elongation, termination, and RNA processing (which includes splicing) (see, e.g., Griffiths et al., eds., Modern Genetic Analysis: Integrating Genes and Genomes, 2nd ed., W.H. Freeman and Co., New York (2002)).

Vector sequences including AAV vectors can include one or more "expression control elements." Typically, expression control elements are nucleic acid sequence(s) that influence expression of an operably linked polynucleotide. Control elements, including expression control elements as set forth herein such as promoters and enhancers, present within a vector are included to facilitate proper heterologous polynucleotide transcription and if appropriate translation (e.g., a promoter, enhancer, splicing signal for introns, maintenance of the correct reading frame of the gene to permit in-frame translation of mRNA and, stop codons etc.). Such elements typically act in cis, referred to as a "cis acting" element, but may also act in trans, referred to as a "trans acting" element. Expression control can be effected at the level of transcription, translation, splicing, message stability, etc. Typically, an expression control element that modulates transcription is juxtaposed near the 5' end (i.e., "upstream") of a transcribed polynucleotide. Expression control elements can also be located at the 3' end (i.e., "downstream") of the transcribed sequence or within the transcript (e.g., in an intron). Expression control elements can be located adjacent to or at a distance away from the transcribed sequence (e.g., 1-10, 10-25, 25-50, 50-100, 100 to 500, or more nucleotides from the polynucleotide), even at considerable distances. Nevertheless, owing to the polynucleotide length limitations of certain vectors, such as AAV vectors, such expression control elements will typically be within 1 to 1000 nucleotides from the transcribed polynucleotide. Functionally, expression of operably linked heterologous polynucleotide is at least in part controllable by the element (e.g., promoter) such that the element modulates transcription of the polynucleotide and, as appropriate, translation of the transcript. A specific example of an expression control element is a promoter, which is usually located 5' of the transcribed sequence. Another example of an expression control element is an enhancer, which can be located 5', 3' of the transcribed sequence, or within the transcribed sequence. A "promoter" as used herein can refer to a nucleic acid (e.g., DNA) sequence that is located adjacent to a polynucleotide sequence that encodes a recombinant product. A promoter is typically operatively linked to an adjacent sequence, e.g., heterologous polynucleotide. A promoter typically increases an amount expressed from a heterologous polynucleotide as compared to an amount expressed when no promoter exists. An "enhancer" as used herein can refer to a sequence that is located adjacent to the heterologous polynucleotide. Enhancer elements are typically located upstream of a promoter element but also function and can be located downstream of or within a DNA sequence (e.g., a heterologous polynucleotide). Hence, an enhancer element can be located 100 base pairs, 200 base pairs, or 300 or more base pairs upstream or downstream of a heterologous polynucleotide. Enhancer elements typically increase expressed of a heterologous polynucleotide above increased expression afforded by a promoter element.

Expression control elements (e.g., promoters and/or enhancers) include those active in a particular tissue or cell type, referred to herein as a "tissue-specific expression control elements/promoters." Tissue-specific expression control elements are typically active in specific cell or tissue (e.g., liver, brain, central nervous system, spinal cord, eye, retina, bone, muscle, lung, pancreas, heart, kidney cell, etc.). Expression control elements are typically active in these cells, tissues or organs because they are recognized by transcriptional activator proteins, or other regulators of transcription, that are unique to a specific cell, tissue or organ type. Examples of promoters active in skeletal muscle include promoters from genes encoding skeletal α-actin, myosin light chain 2A, dystrophin, muscle creatine kinase, as well as synthetic muscle promoters with activities higher than naturally-occurring promoters (see, e.g., Li, et al., Nat. Biotech. 17:241-245 (1999)). Examples of promoters that are tissue-specific for liver are the human alpha 1-antitrypsin (hAAT) promoter; albumin, Miyatake, et al. J. Virol., 71:5124-32 (1997); hepatitis B virus core promoter, Sandig, et al., Gene Ther. 3:1002-9 (1996); alpha-fetoprotein (AFP), Arbuthnot, et al., Hum. Gene. Ther., 7:1503-14 (1996)1, bone (osteocalcin, Stein, et al., Mol. Biol. Rep., 24:185-96 (1997); bone sialoprotein, Chen, et al., J. Bone Miner. Res. 11:654-64 (1996)), lymphocytes (CD2, Hansal, et al., J. Immunol., 161:1063-8 (1998); immunoglobulin heavy chain; T cell receptor a chain), neuronal (neuron-specific enolase (NSE) promoter, Andersen, et al., Cell. Mol. Neurobiol., 13:503-15 (1993); neurofilament light-chain gene, Piccioli, et al., Proc. Natl. Acad. Sci. USA, 88:5611-5 (1991); the neuron-specific vgf gene, Piccioli, et al., Neuron, 15:373-84 (1995); among others. An example of an enhancer active in liver is apolipoprotein E (apoE) HCR-1 and HCR-2 (Allan et al., J. Biol. Chem., 272:29113-19 (1997)). Expression control elements also include ubiquitous or promiscuous promoters/enhancers which are capable of driving expression of a polynucleotide in many different cell types. Such elements include, but are not limited to the cytomegalovirus (CMV) immediate early promoter/enhancer sequences, the Rous sarcoma virus (RSV) promoter/enhancer sequences and the other viral promoters/enhancers active in a variety of mammalian cell types, or synthetic elements that are not present in nature (see, e.g., Boshart et al, Cell, 41:521-530 (1985)), the SV40 promoter, the dihydrofolate reductase promoter, the cytoplasmic 3-actin promoter and the phosphoglycerol kinase (PGK) promoter. Expression control elements also can confer expression in a manner that is regulatable, that is, a signal or stimuli increases or decreases expression of the operably linked heterologous polynucleotide. A regulatable element that increases expression of the operably linked polynucleotide in response to a signal or stimuli is also referred to as an "inducible element" (i.e., is induced by a signal). Particular examples include, but are not limited to, a hormone (e.g., steroid) inducible promoter. A regulatable element that decreases expression of the operably linked polynucleotide in response to a signal or stimuli is referred to as a "repressible element" (i.e., the signal decreases expression such that when the signal, is removed or absent, expression is increased). Typically, the amount of increase or decrease conferred by such elements is proportional to the amount of signal or stimuli present; the greater the amount of signal or stimuli, the greater the increase or decrease in expression. Particular non-limiting examples include zinc-inducible sheep metallothionine (MT) promoter; the steroid hormone-inducible mouse mammary tumor virus (MMTV) promoter; the T7 polymerase promoter system (WO 98/10088); the tetracycline-repressible system (Gossen, et al., Proc. Natl. Acad. Sci. USA, 89:5547-5551 (1992)); the tetracycline-inducible system (Gossen, et al., Science. 268:1766-1769 (1995); see also Harvey, et al., Curr. Opin. Chem. Biol. 2:512-518 (1998)); the RU486-inducible system (Wang, et al., Nat. Biotech. 15:239-243 (1997) and Wang, et al., Gene Ther. 4:432-441 (1997)1; and the rapamycin-inducible system (Magari, et al., J. Clin. Invest. 100:2865-2872 (1997); Rivera, et al., Nat. Medicine. 2:1028-1032 (1996)). Other regulatable control elements which may be useful in this context are those which are regulated by a specific physiological state, e.g., temperature, acute phase, development. Expression control elements also include the native elements(s) for the heterologous polynucleotide. A native control element (e.g., promoter) may be used when it is desired that expression of the heterologous polynucleotide should mimic the native expression. The native element may be used when expression of the heterologous polynucleotide is to be regulated temporally or developmentally, or in a tissue-specific manner, or in response to specific transcriptional stimuli. Other native expression control elements, such as introns, polyadenylation sites or Kozak consensus sequences may also be used.

As used herein, "gene" refers to any segment of DNA. Thus, genes include coding sequences and optionally, the regulatory sequences required for their expression. Genes also optionally include non-expressed DNA segments that, for example, form recognition sequences for other proteins.

For a recombinant plasmid, a vector "genome" refers to the portion of the recombinant plasmid sequence that is ultimately packaged or encapsidated to form a viral (e.g., AAV) particle. In cases where recombinant plasmids are used to construct or manufacture recombinant vectors, the vector genome does not include the portion of the "plasmid" that does not correspond to the vector genome sequence of the recombinant plasmid. This non vector genome portion of the recombinant plasmid is referred to as the "plasmid backbone," which is important for cloning and amplification of the plasmid, a process that is needed for propagation and recombinant virus production, but is not itself packaged or encapsidated into virus (e.g., AAV) particles. Thus, a vector "genome" refers to the portion of the vector plasmid that is packaged or encapsidated by virus (e.g., AAV), and which contains a heterologous polynucleotide sequence. The non-vector genome portion of the recombinant plasmid is the "plasmid backbone" that is important for cloning and amplification of the plasmid, e.g., has a selectable marker, such as Kanamycin, but is not itself packaged or encapsidated by virus (e.g., AAV). Amounts of rAAV that encapsidate/package vector genomes can be determined, for example, by quantitative PCR. This assay measures the physical number of packaged vector genomes by real-time quantitative polymerase chain reaction and can be performed at various stages of the manufacturing/purification process, for example, on bulk AAV vector and final product.

As used herein, a "global alignment" is an alignment that aligns two sequences from beginning to end, aligning each base in each sequence only once. An alignment is produced regardless of whether or not there is similarity or identity between the sequences. For example, 50% sequence identity based on "global alignment" means that in an alignment of the full sequence of two compared sequences each of 100 nucleotides in length, 50% of the bases are the same. It is understood that global alignment also can be used in determining sequence identity even when the length of the aligned sequences is not the same. The differences in the terminal ends of the sequences will be taken into account in determining sequence identity, unless the "no penalty for end gaps" is selected. Generally, a global alignment is used on sequences that share significant similarity over most of their length. Exemplary methods for performing global alignment include the Needleman-Wunsch method (Needleman et al. J. Mol. Biol. 48: 443 (1970)). Exemplary programs for performing global alignment are publicly available and include the Global Sequence Alignment Tool available at the National Center for Biotechnology Information (NCBI) website (ncbi.nlm.nih.gov/), and the program available at blast.ncbi.nlm.nih.gov/Blast.cgi?PAGE_TYPE=BlastSearch&BLAST_SPEC=GlobalAln.

A "heterologous" polynucleotide refers to a polynucleotide inserted into a vector (e.g., AAV) for purposes of vector mediated transfer/delivery of the polynucleotide into a cell. Heterologous polynucleotides are typically distinct from vector (e.g., AAV) nucleic acid, i.e., are non-native with respect to viral (e.g., AAV) nucleic acid. Once transferred/delivered into the cell, a heterologous polynucleotide, contained within the vector, can be expressed (e.g., transcribed, and translated if appropriate). Alternatively, a transferred/delivered heterologous polynucleotide in a cell, contained within the vector, need not be expressed. Although the term "heterologous" is not always used herein in reference to polynucleotides, reference to a polynucleotide even in the absence of the modifier "heterologous" is intended to include heterologous polynucleotides in spite of the omission. In some aspects, a heterologous polynucleotide can be a transgene. For example, a transgene can be a therapeutic being delivered to a cell using a recombinant AAV vector wherein the transgene is heterologous to the AAV vector.

The terms "homologous" or "homology" mean that two or more referenced entities share at least partial identity over a given region or portion. "Areas, regions or domains" of homology or identity mean that a portion of two or more referenced entities share homology or are the same. Thus, where two sequences are identical over one or more sequence regions they share identity in these regions. "Substantial homology" means that a molecule is structurally or functionally conserved such that it has or is predicted to have at least partial structure or function of one or more of the structures or functions (e.g., a biological function or activity) of the reference molecule, or relevant/corresponding region or portion of the reference molecule to which it shares homology. The extent of identity (homology) between two sequences can be ascertained using a computer program and/or mathematical algorithm. Such algorithms that calculate percent sequence identity (homology) generally account for sequence gaps and mismatches over the comparison region or area. For example, a BLAST (e.g., BLAST 2.0) search algorithm (see, e.g., Altschul et al., J. Mol. Biol. 215:403 (1990), publicly available through NCBI) has exemplary search parameters as follows: Mismatch-2; gap open 5; gap extension 2. For polypeptide sequence comparisons, a BLASTP algorithm is typically used in combination with a scoring matrix, such as PAM100, PAM 250, BLOSUM 62 or BLOSUM 50. FASTA (e.g., FASTA2 and FASTA3) and SSEARCH sequence comparison programs are also used to quantitate extent of identity (Pearson et al., Proc. Natl. Acad. Sci. USA 85:2444 (1988); Pearson, Methods Mol Biol. 132:185 (2000); and Smith et al., J. Mol. Biol. 147:195 (1981)). Programs for quantitating protein structural similarity using Delaunay-based topological mapping have also been developed (Bostick et al., Biochem Biophys Res Commun. 304:320 (2003)).

The term "identical," and grammatical variations thereof, mean that two or more referenced entities (e.g., a polypeptide or polynucleotide sequence) are the same, when they are "aligned" sequences. An "aligned" sequence refers to multiple polynucleotide or protein (amino acid) sequences, often containing corrections for missing or additional bases or amino acids (gaps) as compared to a reference sequence. Thus, by way of example, when two polypeptide sequences are identical, they have the same amino acid sequence, at least within the referenced region or portion. Where two polynucleotide sequences are identical, they have the same polynucleotide sequence, at least within the referenced region or portion. The identity can be over a defined area (region or domain) of the sequence. An "area" or "region" of identity refers to a portion of two or more referenced entities (e.g., a polypeptide or polynucleotide) that are identical. Thus, where two protein or nucleic acid sequences are identical over one or more sequence areas or regions they share identity within that region. The identity can extend over the entire length or a portion of the sequence. In particular aspects, the length of the sequence sharing the percent identity is 2, 3, 4, 5 or more contiguous polynucleotide or amino acids, e.g., 6, 7, 8, 9, 10, 11, 12, 13, 14, 15, 16, 17, 18, 19, 20, etc. contiguous polynucleotides or amino acids. In additional particular aspects, the length of the sequence sharing identity is 21 or more contiguous polynucleotide or amino acids, e.g., 21, 22, 23, 24, 25, 26, 27, 28, 29, 30, 31, 32, 33, 34, 35, 36, 37, 38, 39, 40, etc. contiguous polynucleotides or amino acids. In further particular aspects, the length of the sequence sharing identity is 41 or more contiguous polynucleotide or amino acids, e.g. 42, 43, 44, 45, 45, 47, 48, 49, 50, etc., contiguous polynucleotides or amino acids. In yet further particular aspects, the length of the sequence sharing identity is 50 or more contiguous polynucleotide or amino acids, e.g., 50-55, 55-60, 60-65, 65-70, 70-75, 75-80, 80-85, 85-90, 90-95, 95-100, 100-110, etc. contiguous polynucleotide or amino acids.

As used herein, a "local alignment" is an alignment that aligns two sequences, but only aligns those portions of the sequences that share similarity or identity. Hence, a local alignment determines if sub-segments of one sequence are present in another sequence. If there is no similarity, no alignment will be returned. Example local alignment methods include, but are not limited to, BLAST or Smith-Waterman method (Adv. Appl. Math. 2: 482 (1981)). For example, 50% sequence identity based on "local alignment" means that in an alignment of the full sequence of two compared sequences of any length, a region of similarity or identity of 100 nucleotides in length has 50% of the bases that are the same in the region of similarity or identity.

Polynucleotides, polypeptides and subsequences thereof include modified and variant forms. As used herein, the terms "modified" or "variant," and grammatical variations thereof, mean that a polynucleotide, polypeptide or subsequence thereof deviates from a reference sequence. Modified and variant sequences may therefore have substantially the same, greater or less activity or function than a reference sequence, but at least retain partial activity or function of the reference sequence. In particular embodiments, a variant ITR has one or more deletions, additions or substitutions compared to wild type AAV ITR. An example of an amino acid substitution is a conservative amino acid substitution. Another example of an amino acid substitution is an arginine for a lysine residue (e.g., one or more arginine substitution of a lysine as set forth in any of 4-1, 15-1, 15-2, 15-3/15-5, 15-4 and/or 15-6). Further modifications include additions (e.g., insertions or 1-3, 3-5, 5-10, 10-15, 15-20, 20-25, 25-30, 30-40, 40-50, 50-100, or more nucleotides or residues) and deletions (e.g., subsequences or fragments) of a reference sequence. In particular embodiments, a modified or variant sequence retains at least part of a function or an activity of unmodified sequence. Such modified forms and variants can have the same, less than, or greater, but at least a part of, a function or activity of a reference sequence, for example, as described herein.

As set forth herein, a variant can have one or more non-conservative or a conservative amino acid sequence differences or modifications, or both. A "conservative substitution" is the replacement of one amino acid by a biologically, chemically or structurally similar residue. Biologically similar means that the substitution does not destroy a biological activity. Structurally similar means that the amino acids have side chains with similar length, such as alanine, glycine and serine, or a similar size. Chemical similarity means that the residues have the same charge or are both hydrophilic or hydrophobic. Particular examples include the substitution of one hydrophobic residue, such as isoleucine, valine, leucine or methionine for another, or the substitution of one polar residue for another, such as the substitution of arginine for lysine, glutamic for aspartic acids, or glutamine for asparagine, serine for threonine, and the like. Particular examples of conservative substitutions include the substitution of a hydrophobic residue such as isoleucine, valine, leucine or methionine for another, the substitution of a polar residue for another, such as the substitution of arginine for lysine, glutamic for aspartic acids, or glutamine for asparagine, and the like. For example, conservative amino acid substitutions typically include substitutions within the following groups: glycine, alanine; valine, isoleucine, leucine; aspartic acid, glutamic acid; asparagine, glutamine; serine, threonine; lysine, arginine; and phenylalanine, tyrosine. A "conservative substitution" also includes the use of a substituted amino acid in place of an unsubstituted parent amino acid.

As used herein, "nucleic acid sequencing data," "nucleic acid sequencing information," "nucleic acid sequence," "nucleotide sequence," "genomic sequence," "genetic sequence," "fragment sequence," "nucleic acid sequencing read," "sequence data" and the like, denotes any information or data that is indicative of the order of the nucleotide bases (e.g., adenine, guanine, cytosine, and thymine or uracil) in a molecule (e.g., a whole genome, whole transcriptome, exome, oligonucleotide, polynucleotide, or fragment) of a nucleic acid such as DNA or RNA. It should be understood that the present teachings contemplate sequence information obtained using all available varieties of techniques, platforms or technologies, including, but not limited to: NGS, capillary electrophoresis, microarrays, ligation-based systems, polymerase-based systems, hybridization-based systems, direct or indirect nucleotide identification systems, pyrosequencing, ion- or pH-based detection systems, and electronic signature-based systems.

As used herein, the term "operable linkage" or "operably linked" refers to a physical or functional juxtaposition of the components so described as to permit them to function in their intended manner. In the example of an expression control element in operable linkage with a nucleic acid, the relationship is such that the control element modulates expression of the nucleic acid. More specifically, for example, two DNA sequences operably linked means that the two DNAs are arranged (cis or trans) in such a relationship that at least one of the DNA sequences is able to exert a physiological effect upon the other sequence. Accordingly, modified nucleic acid sequences encoding a human protein, and vectors and plasmids, including viral vectors such as AAV vectors, as well as compositions thereof, can include additional nucleic acid elements. These elements include, without limitation one or more copies of an AAV ITR sequence, an expression control (e.g., promoter/enhancer) element, a transcription termination signal or stop codon, 5' or 3' untranslated regions (e.g., polyadenylation (polyA) sequences) which flank a polynucleotide sequence, or an intron. Nucleic acid elements further include, for example, filler or stuffer polynucleotide sequences, for example to improve packaging and reduce the presence of contaminating nucleic acid, e.g., to reduce packaging of the plasmid backbone. As disclosed herein, AAV vectors typically accept inserts of DNA having a defined size range which is generally about 4 kb to about 5.2 kb, or slightly more. Thus, for shorter sequences, inclusion of a stuffer or filler in the insert fragment in order to adjust the length to near or at the normal size of the virus genomic sequence acceptable for AAV vector packaging into virus particle. In various embodiments, a filler/stuffer nucleic acid sequence is an untranslated (non-protein encoding) segment of nucleic acid. In particular embodiments of an AAV vector, a heterologous polynucleotide sequence has a length less than 4.7 kb and the filler or stuffer polynucleotide sequence has a length that when combined (e.g., inserted into a vector) with the heterologous polynucleotide sequence has a total length between about 3.0-5.5 kb, or between about 4.0-5.0 Kb, or between about 4.3-4.8 Kb. An intron can also function as a filler or stuffer polynucleotide sequence in order to achieve a length for AAV vector packaging into a virus particle. Introns and intron fragments that function as a filler or stuffer polynucleotide sequence also can enhance expression. Inclusion of an intron element may enhance expression compared with expression in the absence of the intron element (Kurachi et al., 1995, supra). Expression control elements, ITRs, poly A sequences, filler or stuffer polynucleotide sequences can vary in length. In particular aspects, an expression control element, ITR, polyA, or a filler or stuffer polynucleotide sequence is a sequence between about 1-10, 10-20, 20-30, 30-40, 40-50, 50-60, 60-75, 75-100, 100-150, 150-200, 200-250, 250-300, 300-400, 400-500, 500-750, 750-1,000, 1,000-1,500, 1,500-2,000, or 2,000-2,500 nucleotides in length.

"Optional" or "optionally" means that the subsequently described event, circumstance, or material may or may not occur or be present, and that the description includes instances where the event, circumstance, or material occurs or is present and instances where it does not occur or is not present.

The terms "polynucleotide" and "nucleic acid" are used interchangeably herein to refer to all forms of nucleic acid, oligonucleotides, including deoxyribonucleic acid (DNA) and ribonucleic acid (RNA). Polynucleotides include genomic DNA, cDNA and antisense DNA, and spliced or unspliced mRNA, rRNA tRNA and inhibitory DNA or RNA (RNAi, e.g., small or short hairpin (sh)RNA, microRNA (miRNA), small or short interfering (si)RNA, trans-splicing RNA, or antisense RNA). Polynucleotides include naturally occurring, synthetic, and intentionally modified or altered polynucleotides (e.g., having reduced CpG dinucleotides). Polynucleotides can be single, double, or triplex, linear or circular, and can be of any length. In discussing polynucleotides, a sequence or structure of a particular polynucleotide may be described herein according to the convention of providing the sequence in the 5' to 3' direction. Polynucleotides include additions and insertions, for example, one or more heterologous domains. An addition (e.g., heterologous domain) can be a covalent or non-covalent attachment of any type of molecule to a composition.

Typically additions and insertions (e.g., a heterologous domain) confer a complementary or a distinct function or activity. Additions and insertions include chimeric and fusion sequences, which is a polynucleotide or protein sequence having one or more molecules not normally present in a reference native (wild type) sequence covalently attached to the sequence. The terms "fusion" or "chimeric" and grammatical variations thereof, when used in reference to a molecule means that a portions or part of the molecule contains a different entity distinct (heterologous) from the molecule—as they do not typically exist together in nature. That is, for example, one portion of the fusion or chimera, includes or consists of a portion that does not exist together in nature, and is structurally distinct.

The "polypeptides," "proteins" and "peptides" encoded by "polynucleotide" or "nucleic acid" sequences include full-length native sequences, as with naturally occurring proteins, as well as functional subsequences, modified forms or sequence variants so long as the subsequence, modified form or variant retains some degree of functionality of the native full-length protein. In methods and uses of the invention, such polypeptides, proteins and peptides encoded by the polynucleotide sequences can be but are not required to be identical to the endogenous protein that is defective, or whose expression is insufficient, or deficient in the treated mammal.

A "promoter" or "promoter sequence" is a DNA regulatory region capable of binding RNA polymerase in a cell and initiating transcription of a polynucleotide or polypeptide coding sequence such as messenger RNA, ribosomal RNAs, small nuclear of nucleolar RNAs or any kind of RNA transcribed by any class of any RNA polymerase I, II or III As used herein, the term "recombinant," as a modifier of viral vector, such as recombinant AAV vectors, as well as a modifier of sequences such as recombinant polynucleotides and polypeptides, means that the compositions (e.g., AAV or sequences) have been manipulated (i.e., engineered) in a fashion that generally does not occur in nature. A particular example of a recombinant vector, such as an AAV vector would be where a polynucleotide that is not normally present in the wild-type viral (e.g., AAV) genome is inserted within the viral genome. For example, an example of a recombinant polynucleotide would be where a heterologous polynucleotide (e.g., gene) encoding a protein is cloned into a vector, with or without 5', 3' and/or intron regions that the gene is normally associated within the viral (e.g., AAV) genome. Although the term "recombinant" is not always used herein in reference to vectors, such as viral and AAV vectors, as well as sequences such as polynucleotides and polypeptides, recombinant forms of viral, AAV, and sequences including polynucleotides and polypeptides, are expressly included in spite of any such omission.

A recombinant viral "vector" or "AAV vector" is derived from the wild type genome of a virus, such as AAV by using molecular methods to remove the wild type genome from the virus (e.g., AAV), and replacing with a non-native nucleic acid, such as a heterologous polynucleotide sequence. Typically, for AAV one or both inverted terminal repeat (ITR) sequences of AAV genome are retained in the AAV vector. A "recombinant" viral vector (e.g., AAV) is distinguished from a viral (e.g., AAV) genome, since all or a part of the viral genome has been replaced with a non-native sequence with respect to the viral (e.g., AAV) genomic nucleic acid such as a heterologous polynucleotide sequence. Incorporation of a non-native sequence therefore defines the viral vector (e.g., AAV) as a "recombinant" vector, which in the case of AAV can be referred to as a "rAAV vector." A recombinant vector (e.g., rAAV) sequence can be packaged—referred to herein as a "particle" for subsequent infection (transduction) of a cell, ex vivo, in vitro or in vivo. Where a recombinant vector sequence is encapsidated or packaged into an AAV particle, the particle can also be referred to as a "rAAV." Such particles include proteins that encapsidate or package the vector genome. Particular examples include viral envelope proteins, and in the case of AAV, capsid proteins. Recombinant vector sequences are manipulated by insertion or incorporation of a polynucleotide. As disclosed herein, a vector plasmid generally contains at least an origin of replication for propagation in a cell and one or more expression control elements.

As used herein, "sequence identity," "sequence homology," or "identity" refers to the number of identical or similar nucleotide bases in an alignment between two or more polynucleotide sequences. In one non-limiting example, "at least 90% identical to" refers to percent identities from 90 to 100% relative to the reference polynucleotide. Identity at a level of 90% or more is indicative of the fact that, assuming for exemplification purposes a test and reference polynucleotide length of 100 nucleotides are compared, no more than 10% (i.e., 10 out of 100) of nucleotides in the test polynucleotide differs from that of the reference polynucleotide. Such differences can be represented as point mutations randomly distributed over the entire length of a nucleotide sequence or they can be clustered in one or more locations of varying length up to the maximum allowable, e.g., 10/100 nucleotide difference (approximately 90% identity). Differences are defined as nucleic acid substitutions, insertions or deletions. Sequence identity can be determined by sequence alignment of nucleic acid sequences to identify regions of similarity or identity. For purposes herein, sequence identity is generally determined by alignment to identify identical bases. The alignment can be local or global. Matches, mismatches and gaps can be identified between compared sequences. Gaps are null nucleotides inserted between the bases of aligned sequences so that identical or similar characters are aligned. Generally, there can be internal and terminal gaps. Sequence identity can be determined by taking into account gaps as the number of identical bases/length of the shortest sequence×100. When using gap penalties, sequence identity can be determined with no penalty for end gaps (e.g., terminal gaps are not penalized). Alternatively, sequence identity can be determined without taking into account gaps as the number of identical positions/length of the total aligned sequence×100.

As used herein, the terms "sequencing" or "sequencer" refer to any of a number of technologies used to determine the sequence of a biomolecule, e.g., a nucleic acid such as DNA or RNA. Exemplary sequencing methods include, but are not limited to, targeted sequencing, single molecule real-time sequencing, exon sequencing, electron microscopy-based sequencing, panel sequencing, transistor-mediated sequencing, direct sequencing, random shotgun sequencing, Sanger dideoxy termination sequencing, whole-genome sequencing, sequencing by hybridization, pyrosequencing, duplex sequencing, cycle sequencing, single-base extension sequencing, solid-phase sequencing, high-throughput sequencing, massively parallel signature sequencing, emulsion PCR, co-amplification at lower denaturation temperature-PCR (COLD-PCR), multiplex PCR, sequencing by reversible dye terminator, paired-end sequencing, near-term sequencing, exonuclease sequencing, sequencing by ligation, short-read sequencing, single-molecule sequencing, sequencing-by-synthesis, real-time sequencing, reverse-terminator sequencing, nanopore sequencing, 454 sequencing, Solexa Genome Analyzer sequencing, SOLiD™ sequencing, MS-PET sequencing, and a combination thereof. In some embodiments, sequencing can be performed by a gene analyzer such as, for example, gene analyzers commercially available from Illumina, Applied Biosystems, Oxford Nanopore Technologies, and Pacific Biosciences.

As used herein, "subject" or "patient" refers to an animal, such as a mammalian species (e.g., human) or avian (e.g., bird) species, or other organism, such as a plant. More specifically, a subject can be a vertebrate, e.g., a mammal such as a mouse, a primate, a simian, or a human. Animals include farm animals (e.g., production cattle, dairy cattle, poultry, horses, pigs, and the like), sport animals, and companion animals (e.g., pets or support animals). A subject can be a healthy individual, an individual that has or is suspected of having a disease or a predisposition to the disease, or an individual that is in need of therapy or suspected of needing therapy. The terms "individual" or "patient" are intended to be interchangeable with "subject." In some embodiments, the subject is a human who has, or is suspected of having a disease. The disease may be a genetic disease (e.g., monogenic disease). The disease may be cancer. For example, a subject can be an individual who has been diagnosed with having a cancer, is going to receive a cancer therapy, and/or has received at least one cancer therapy. The subject can be in remission of a cancer. As another example, the subject can be an individual who is diagnosed of having an autoimmune disease. As another example, the subject can be a female individual who is pregnant or who is planning on getting pregnant, who may have been diagnosed with or suspected of having a disease, e.g., a cancer, an auto-immune disease. A "reference subject" refers to a subject known to have or lack specific properties (e.g., known cancer or disease status, known nucleic acid variant(s), known cellular origin, known tumor fraction, known coverage, and/or the like).

A "therapeutic" in one embodiment is a peptide or protein that may alleviate or reduce symptoms that result from an absence or defect in a protein in a cell or subject. Alternatively, a "therapeutic" peptide or protein encoded by a transgene is one that confers a benefit to a subject, e.g., to correct a genetic defect, to correct a gene (expression or functional) deficiency. All mammalian and non-mammalian forms of polynucleotides encoding gene products, including the non-limiting genes and proteins disclosed herein are expressly included, either known or unknown. Thus, the invention includes genes and proteins from non-mammals, mammals other than humans, and humans, which genes and proteins function in a substantially similar manner to the human genes and proteins described herein.

The terms "transduce" and "transfect" refer to introduction of a molecule such as a polynucleotide into a cell or host organism. A cell into which the transgene has been introduced is referred to as a "transduced cell." Accordingly, a "transduced" cell (e.g., in a mammal, such as a cell or tissue or organ cell), means a genetic change in a cell following incorporation of an exogenous molecule, for example, a polynucleotide or protein (e.g., a transgene) into the cell. Thus, a "transduced" cell is a cell into which, or a progeny thereof in which an exogenous molecule has been introduced, for example. The cell(s) can be propagated and the introduced protein expressed, or nucleic acid transcribed. For gene therapy uses and methods, a transduced cell can be in a subject. The introduced polynucleotide may or may not be integrated into nucleic acid of the recipient cell or organism. If an introduced polynucleotide becomes integrated into the nucleic acid (genomic DNA) of the recipient cell or organism it can be stably maintained in that cell or organism and further passed on to or inherited by progeny cells or organisms of the recipient cell or organism. Finally, the introduced nucleic acid may exist in the recipient cell or host organism only transiently. Cells that may be transduced include a cell of any tissue or organ type, of any origin (e.g., mesoderm, ectoderm or endoderm). Non-limiting examples of cells include liver (e.g., hepatocytes, sinusoidal endothelial cells), pancreas (e.g., beta islet cells), lung, central or peripheral nervous system, such as brain (e.g., neural, glial or ependymal cells) or spine, kidney, eye (e.g., retinal, cell components), spleen, skin, thymus, testes, lung, diaphragm, heart (cardiac), muscle or psoas, or gut (e.g., endocrine), adipose tissue (white, brown or beige), muscle (e.g., fibroblasts), synoviocytes, chondrocytes, osteoclasts, epithelial cells, endothelial cells, salivary gland cells, inner ear nervous cells or hematopoietic (e.g., blood or lymph) cells. Additional examples include stem cells, such as pluripotent or multipotent progenitor cells that develop or differentiate into liver (e.g., hepatocytes, sinusoidal endothelial cells), pancreas (e.g., beta islet cells), lung, central or peripheral nervous system, such as brain (e.g., neural, glial or ependymal cells) or spine, kidney, eye (retinal, cell components), spleen, skin, thymus, testes, lung, diaphragm, heart (cardiac), muscle or psoas, or gut (e.g., endocrine), adipose tissue (white, brown or beige), muscle (e.g., fibroblasts), synoviocytes, chondrocytes, osteoclasts, epithelial cells, endothelial cells, salivary gland cells, inner ear nervous cells or hematopoietic (e.g., blood or lymph) cells.

A nucleic acid sequence may be introduced into a cell by "transfection," "transformation," or "transduction." "Transfection," "transformation," or "transduction," as used herein, refers to the introduction of one or more exogenous polynucleotides into a host cell by using physical or chemical methods, including, for example, an expression vector. Many transfection techniques are known in the art and include, for example, calcium phosphate DNA co-precipitation (see, e.g., Murray E. J. (ed.), Methods in Molecular Biology, Vol. 7, Gene Transfer and Expression Protocols, Humana Press (1991)); DEAE-dextran; electroporation; cationic liposome-mediated transfection; tungsten particle-facilitated microparticle bombardment (Johnston, Nature, 346: 776-777 (1990)); and strontium phosphate DNA co-precipitation (Brash et al., Mol. Cell. Biol., 7: 2031-2034 (1987)). Phage or viral vectors can be introduced into host cells, after growth of infectious particles in suitable packaging cells, which are commercially available.

As used herein, "transgene" refers to a polynucleotide that can be expressed, via recombinant techniques, in a non-native environment or heterologous cell under appropriate conditions. The transgene coding region may be inserted in a viral vector. In one embodiment, the viral vector is an adeno-associated viral vector. The transgene may be derived from the same type of cell in which it is to be expressed, but introduced from an exogenous source, modified as compared to a corresponding native form and/or expressed from a non-native site, or it may be derived from a heterologous cell. "Transgene" is synonymous with "exogenous gene," "foreign gene," "heterologous coding sequence," and "heterologous gene." In the context of a vector, a "heterologous polynucleotide" or "heterologous gene" or "transgene" is any polynucleotide or gene that is not present in the corresponding wild-type vector or virus. The transgene coding sequence may be a sequence found in nature that codes for a certain protein. The transgene coding sequence may alternatively be a non-natural coding sequence. For example, one skilled in the art can readily recode a coding sequence to optimize the codons for expression in a certain species using a codon usage chart. In one embodiment, the recoded sequence still codes for the same amino acid sequence as a natural coding sequence for the transgene. A transgene may be a therapeutic gene. A transgene does not necessarily code for a protein.

The term "vector" or "expression vector," as used herein, refers to a molecule (typically a nucleic acid molecule) that contains the necessary sequences to allow transcription and/or translation of a gene or genes cloned therein. A "vector" may be a plasmid, phage, cosmid, virus or viral construct (e.g., AAV vector), or other vehicle that can be manipulated by insertion or incorporation of a polynucleotide. Such vectors can be used for genetic manipulation (i.e., "cloning vectors"), to introduce/transfer polynucleotides into cells, and to transcribe or translate the inserted polynucleotide in cells. A vector nucleic acid sequence generally contains at least an origin of replication for propagation in a cell and optionally additional elements, such as a heterologous polynucleotide sequence, expression control element (e.g., a promoter, enhancer), intron, ITR(s), selectable marker (e.g., antibiotic resistance), poly-Adenine (also referred to as poly-adenylation) sequence. A viral vector is derived from or based upon one or more nucleic acid elements that comprise a viral genome. Particular viral vectors include adeno-associated virus (AAV) vectors. As described, AAV vectors, including AAV1, AAV2, AAV3, AAV4, AAV5, AAV6, AAV7, AAV8, AAV9, AAV10, AAV11, Rh10, Rh74 or AAV-2i8 and related AAV variants such as AAV-Rh74 variants (e.g., capsid variants such as 4-1, 15-1, 15-2, 15-3/15-5, 15-4 and 15-6) can be used to introduce/deliver polynucleotides stably or transiently into cells and progeny thereof.

In some aspects, vectors have circular genomes. In some aspects vectors have linear genomes. In some aspects, a vector or expression vector is a plasmid or virus designed to carry a gene of interest and express the gene of interest in a cell. The expression vector may be inserted into a specific (e.g., targeted) locus. The expression vector can be "episomal." In some aspects, an "episome" is a vector that is able to replicate in a host cell, and persists as an extrachromosomal segment of DNA within the host cell in the presence of appropriate selective pressure (see, e.g., Conese et al., Gene Therapy, 11: 1735-1742 (2004)). Representative commercially available episomal expression vectors include, but are not limited to, episomal plasmids that utilize Epstein Barr Nuclear Antigen 1 (EBNA1) and the Epstein Barr Virus (EBV) origin of replication (oriP). The vectors pREP4, pCEP4, pREP7, and pcDNA3.1 from Invitrogen (Carlsbad, Calif), and pBK-CMV from Stratagene (La Jolla, Calif.) represent non-limiting examples of an episomal vector that uses T-antigen and the SV40 origin of replication in lieu of EBNA1 and oriP. In some aspects, the episome can be an AAV episome that does not replicate in a host cell. In some aspects, AAV episomes do not integrate into the host genome and therefore, in dividing cells they can be lost over repeated rounds of cell division. Other suitable vectors include integrating expression vectors, which may randomly integrate into the host cell's DNA, or may include a recombination site to enable the specific recombination between the expression vector and the host cell's chromosomes. Such integrating expression vectors may utilize the endogenous expression control sequences of the host cell's chromosomes to effect expression of the desired protein. Examples of vectors that integrate in a site-specific manner include, for example, components of the flp-in system from Invitrogen (Carlsbad, Calif.) (e.g., pcDNA™5/FRT), or the cre-lox system, such as is found in the pExchange-6 Core Vectors from Stratagene (La Jolla, Calif.). Examples of vectors that randomly integrate into host cell chromosomes include, for example, pcDNA3.1 (when introduced in the absence of T-antigen) from Invitrogen (Carlsbad, Calif), and pCI or pFN10A (ACT) FLEXI™ from Promega (Madison, Wis.). Other suitable vectors may include non-viral vectors or liquid nanoparticle (LNP) vectors. The expression vector can be a viral vector. Representative viral expression vectors include, but are not limited to, adeno-associated viral (AAV) vector, adenovirus, hybrid adenoviral system, a portion of any of these, or a fragment of any of these, or any combination thereof.).

As used herein, the singular forms "a," "and," and "the" include plural referents unless the context clearly indicates otherwise. Thus, for example, reference to "a nucleic acid" includes a plurality of such nucleic acids, reference to "a vector" includes a plurality of such vectors, and reference to "a virus" or "particle" includes a plurality of such virions/particles. Likewise, for example, reference to "a sequence" includes a plurality of sequences, reference to "the sequence" is a reference to one or more sequences and equivalents thereof known to those skilled in the art, and so forth.

As used herein, all numerical values or ranges include fractions of the values and integers within such ranges and fractions of the integers within such ranges unless the context clearly indicates otherwise. Thus, to illustrate, reference to 80% or more identity, includes 81%, 82%, 83%, 84%, 85%, 86%, 87%, 88%, 89%, 90%, 91%, 92%, 93%, 94% etc., as well as 81.1%, 81.2%, 81.3%, 81.4%, 81.5%, etc., 82.1%, 82.2%, 82.3%, 82.4%, 82.5%, etc., and so forth. Reference to a numerical range, such as 1-10 includes 1, 2, 3, 4, 5, 6, 7, 8, 9, 10, as well as 1.1, 1.2, 1.3, 1.4, 1.5, etc., and so forth. Reference to a range of 1-50 therefore includes 1, 2, 3, 4, 5, 6, 7, 8, 9, 10, 11, 12, 13, 14, 15, 16, 17, 18, 19, 20, etc., up to and including 50, as well as 1.1, 1.2, 1.3, 1.4, 1.5, etc., 2.1, 2.2, 2.3, 2.4, 2.5, etc., and so forth. Reference to a series of ranges includes ranges which combine the values of the boundaries of different ranges within the series. Thus, to illustrate reference to a series of ranges, for example, of 1-10, 10-20, 20-30, 30-40, 40-50, 50-60, 60-75, 75-100, 100-150, 150-200, 200-250, 250-300, 300-400, 400-500, 500-750, 750-1,000, 1,000-1,500, 1,500-2,000, 2,000-2,500, 2,500-3,000, 3,000-3,500, 3,500-4,000, 4,000-4,500, 4,500-5,000, 5,500-6,000, 6,000-7,000, 7,000-8,000, or 8,000-9,000, includes ranges of 10-50, 50-100, 100-1,000, 1,000-3,000, 2,000-4,000, etc. Ranges may also be expressed herein as from "about" one particular value, and/or to "about" another particular value. When such a range is expressed, also specifically contemplated and considered disclosed is the range from the one particular value and/or to the other particular value unless the context specifically indicates otherwise. Similarly, when values are expressed as approximations, by use of the antecedent "about," it will be understood that the particular value forms another, specifically contemplated embodiment that should be considered disclosed unless the context specifically indicates otherwise. It will be further understood that the endpoints of each of the ranges are significant both in relation to the other endpoint, and independently of the other endpoint unless the context specifically indicates otherwise. Finally, it should be understood that all of the individual values and subranges of values contained within an explicitly disclosed range are also specifically contemplated and should be considered disclosed unless the context specifically indicates otherwise. The foregoing applies regardless of whether in particular cases some or all of these embodiments are explicitly disclosed.

The invention is generally disclosed herein using affirmative language to describe the numerous embodiments and aspects. The invention also specifically includes embodiments in which particular subject matter is excluded, in full or in part, such as substances or materials, method steps and conditions, protocols, or procedures. For example, in certain embodiments or aspects of the invention, materials and/or method steps are excluded. Thus, even though the invention is generally not expressed herein in terms of what the invention does not include aspects that are not expressly excluded in the invention are nevertheless disclosed herein.

All of the features disclosed herein may be combined in any combination. Each feature disclosed in the specification may be replaced by an alternative feature serving a same, equivalent, or similar purpose. Thus, unless expressly stated otherwise, disclosed features (e.g., modified nucleic acid, vector, plasmid, a recombinant vector (e.g., rAAV) sequence, vector genome, or recombinant virus particle) are an example of a genus of equivalent or similar features.

All applications, publications, patents and other references, GenBank citations and ATCC citations cited herein are incorporated by reference in their entirety. In case of conflict, the specification, including definitions, will control.

B. Adeno-Associated Viral (AAV) Vectors

FIG. 1 shows an example diagram of an AAV vector 100 and DNA 101 packaged within the AAV vector 100. In some aspects, the AAV vector is referred to as a recombinant AAV vector. A recombinant AAV vector comprises a non-native sequence, such as a heterologous transgene. Two inverted terminal repeat (ITR) sequences 102 and 105 from the AAV genome, one on the 5' end (102) and one on the 3' end (105), are required in the packaged DNA 101 of AAV vector 100. Foreign DNA (including the transgene/gene of interest) can be introduced between the ITRs 102 and 105. The foreign DNA can include, but is not limited to, a transgene/gene of interest 103, and/or polyA 104 as shown in FIG. 1. Optionally, a promoter (with or without enhancer elements) may be included in the foreign DNA.

The transgene sequence 103 encodes a gene product of interest, which can be an RNA molecule (e.g., mRNA, tRNA, and/or shRNA) or a polypeptide (also referred to herein as a "protein"). In some instances, the gene product of interest may be Factor 9 ("F9"). Examples of suitable proteins include, for example, surface proteins, intracellular proteins, membrane proteins, and secreted proteins from any unmodified or synthetic source. The gene product of interest may be an antibody heavy chain or portion thereof, an antibody light chain or portion thereof, an enzyme, a receptor, a structural protein, a co-factor, a polypeptide, a peptide, an intrabody, a selectable marker, a toxin, a growth factor, or a peptide hormone.

The gene product of interest can be any suitable enzyme, including enzymes associated with microbiological fermentation, metabolic pathway engineering, protein manufacture, bio-remediation, and plant growth and development (see, e.g., Olsen et al., Methods Mol. Biol., 230: 329-349 (2003); Turner, Trends Biotechnol., 21(11): 474-478 (2003); Zhao et al., Curr. Opin. Biotechnol., 13(2): 104-110 (2002); and Mastrobattista et al., Chem. Biol., 12(12): 1291-300 (2005)).

The gene product of interest can be an antigen. An "antigen" is any molecule that induces an immune response in a mammal. An "immune response" can entail, for example, antibody production and/or the activation of immune effector cells (e.g., T-cells). An antigen can comprise any subunit, fragment, or epitope of any proteinaceous or non-proteinaceous (e.g., carbohydrate or lipid) molecule which provokes an immune response in mammal. By "epitope" is meant a sequence on an antigen that is recognized by an antibody or an antigen receptor. Epitopes also are referred to in the art as "antigenic determinants."

In an embodiment, the gene product of interest is an antibody or a portion thereof. For example, the gene product of interest can be an antibody heavy chain or portion thereof or an antibody light chain or portion thereof. The nucleic acid sequence can encode an antibody, or fragment thereof, directed against any suitable antigen. Nucleic acid sequences encoding all naturally occurring germline, affinity matured, synthetic, or semi-synthetic antibodies, as well as fragments thereof, can be used. The gene product can be any suitable antibody fragment, such as, e.g., F(ab')2, Fab', Fab, Fv, scFv, dsFv, dAb, or a single chain binding polypeptide. The antibody, or fragment thereof, desirably is a mammalian antibody (e.g., a human antibody or a non-human antibody). The antibody may be a human antibody. A human antibody, a non-human antibody, or a chimeric antibody can be obtained by any means, including in vitro sources (e.g., a hybridoma or a cell line producing an antibody recombinantly) and in vivo sources (e.g., rodents). Methods for generating antibodies are known in the art and are described in, for example, see, e.g., Köhler and Milstein, Eur. J. Immunol., 5: 511-519 (1976); Harlow and Lane (eds.), Antibodies: A Laboratory Manual, CSH Press (1988); and C. A. Janeway et al. (eds.), Immunobiology, 5th Ed., Garland Publishing, New York, N.Y. (2001)).

In certain embodiments, a human antibody or a chimeric antibody can be generated using a transgenic animal (e.g., a mouse) wherein one or more endogenous immunoglobulin genes are replaced with one or more human immunoglobulin genes. Examples of transgenic mice wherein endogenous antibody genes are effectively replaced with human antibody genes include, but are not limited to, the HUMAB-MOUSE™, the Kirin TC MOUSE™, and the KM-MOUSE™ (see, e.g., Lonberg N., Nat. Biotechnol., 23(9): 1117-25 (2005); and Lonberg N., Handb. Exp. Pharmacol., 181: 69-97 (2008)).

In some embodiments, the gene product of interest can be a fusion protein (also referred to in the art as a "chimeric protein"). Fusion proteins are generated by transcriptionally linking two or more nucleic acid sequences which code for separate proteins. Translation of the linked genes produces a single polypeptide with functional properties derived from each of the individual proteins. The fusion protein can be naturally occurring (e.g., antibody proteins or the bcr-abl fusion protein), or the fusion protein can be synthetically generated using recombinant DNA techniques known in the art. For example, a nucleic acid sequence encoding a peptide tag can be ligated to a second nucleic acid sequence encoding a gene product of interest to facilitate protein purification and/or identification. Suitable peptide tags include, for example, a glutathione-S-transferase (GST) protein, a FLAG peptide, or a polyhistidine (HIS) tag. Fc fusion proteins are another type of synthetic fusion protein that can be used. Fc fusion proteins contain a soluble antibody constant fragment (Fc). Soluble Fc fusion proteins can be used as reagents for several in vitro and in vivo applications, including, but not limited to, immunotherapy, flow cytometry, immunohistochemistry, and in vitro activity assays. Fc fusion proteins are described in, for example, Flanagan et al., "Soluble Fc Fusion Proteins for Biomedical Research," In: M. Albitar, ed., Monoclonal Antibodies: Methods and Protocols (Methods in Molecular Biology), Human Press, Inc., pp. 33-52 (2008). The fusion protein can be used for therapeutic or diagnostic purposes. For example, a therapeutic fusion protein can be generated in which one portion of the fusion protein is capable of directing the fusion protein to a specific cell or tissue, while the other portion of the fusion protein is a biologically active protein or peptide (also referred to in the art as a "payload"), such as an antibody or a cytotoxic protein.

Figure 2A:
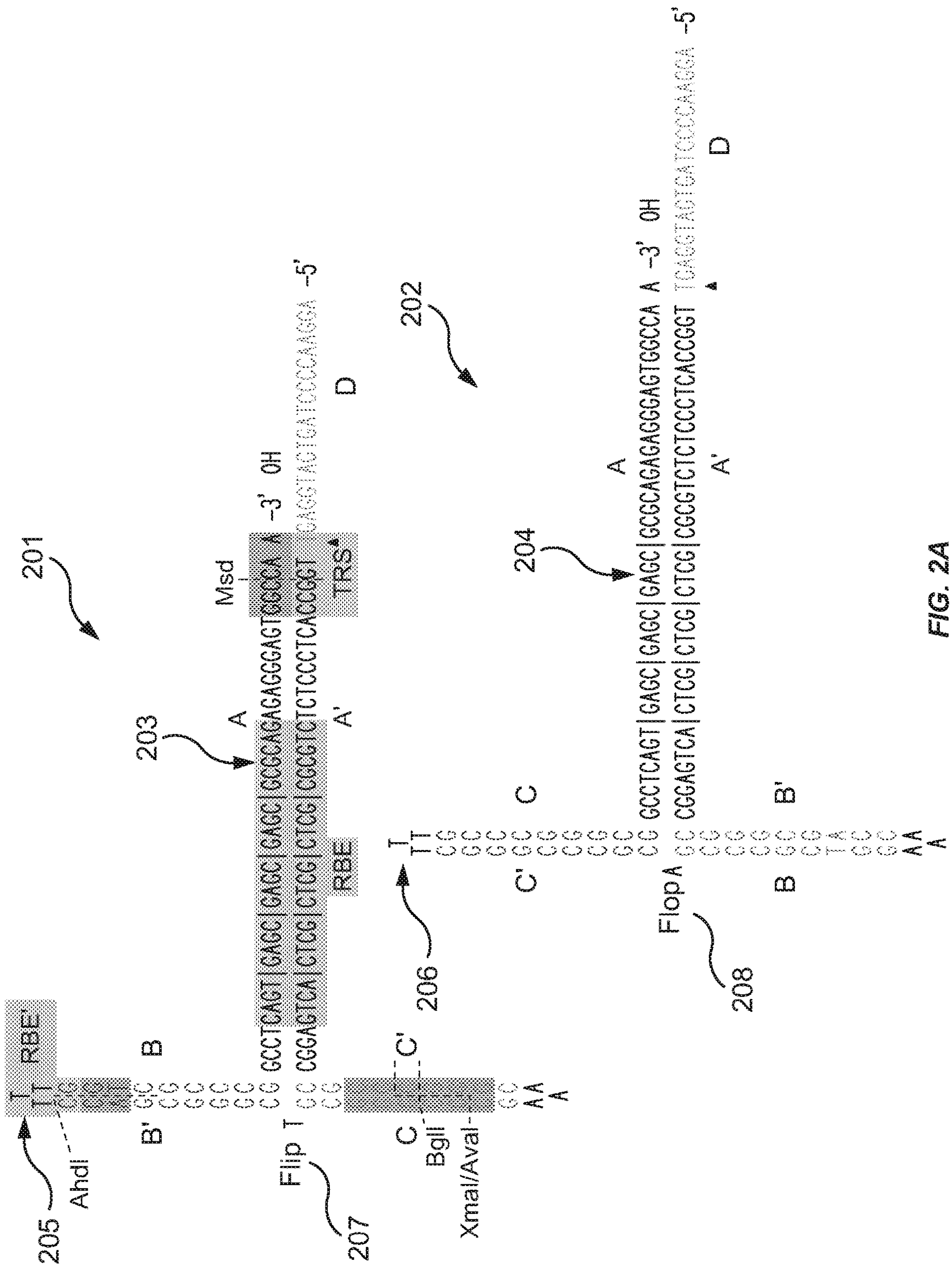
FIG. 2A shows secondary structure of ITRs of the AAV viral genome.

As shown in FIG. 2A, the ITRs of the AAV viral genome (e.g., the ITRs 102 and/or 105) may be characterized by a secondary structure (201, 202). The secondary structure (201, 202) may be referred to as hairpin structures (201, 202), which are cruciform (e.g., "T") configurations that can form when a single strand of DNA folds back on itself and pairs with a complementary sequence within the same strand. These hairpin structures (201, 202) are a defining feature of ITRs and play a role in the replication, packaging, and integration of the AAV genome. The hairpin structure (201, 202) of ITRs may include a stem region (203, 204), composed of perfectly or nearly perfectly base-paired sequences, and a loop region (205, 206), where the DNA strand turns to pair back on itself. The stability and sequence of these hairpin structures (201, 202) can influence the efficiency of the AAV vector in gene delivery, as they are involved in the initiation of replication and are recognized by the cellular and viral proteins that mediate replication and packaging. In some cases, the hairpin structures (201, 202) may also contain palindromic sequences, which can further enhance the formation of the hairpin by providing complementary bases that facilitate the folding and base pairing. Identifying the genotype of these ITR sequences, including any variations in their hairpin structures (201, 202), may be integral to optimizing the production and therapeutic efficacy of AAV vectors.

Figure 2B:
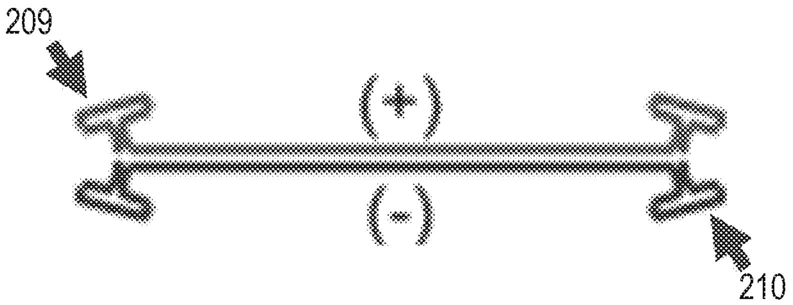
FIG. 2B shows a flip L-ITR strand and a flip R-ITR strand.

In some aspects, the ITR hairpin structures (201, 202) may exist in two variant forms known as "flip" (207) and "flop" (208). These variants may be distinguished by the orientation of the palindromic sequences within the loop region (205, 206) of the hairpin structure (201, 202). In the "flip" variant (207), the palindromic sequences are oriented in such a way that they facilitate the formation of a hairpin (201) with a particular polarity. Conversely, in the "flop" variant (202), the orientation of the palindromic sequences is reversed, leading to the formation of a hairpin (202) with the opposite polarity. The presence of these flip (207) and flop (208) variants can have implications for the replication and packaging of the AAV genome, as the orientation of the hairpin (201, 202) may affect the interaction with replication and packaging machinery. Produced viruses will proportionally contain flip (207) and flop (208) variants in each ITR (4 different combinations). As shown in FIG. 2B, a flip L-ITR in a (+) strand 209 has identical sequence to a flip R-ITR in a (–) strand 210. In some cases, the flip-flop configuration may also influence the site-specific integration of the AAV genome into the host genome. Therefore, the identification of the flip (207) or flop (208) variant forms of the ITR hairpin structures (201, 202) in a candidate ITR sequence may provide valuable information for the design and optimization of AAV vectors for gene therapy applications.

Provided herein are nucleic acid sequences, expression vectors, and plasmids used to generate AAV vectors, In some aspects, the AAV vectors comprise nucleic acid sequences that encode therapeutics. Nucleic acids encoding desired therapeutics can be included in nucleic acid sequences, expression vectors, and plasmids used to generate AAV vectors. As a vector for nucleic acid sequence delivery, AAV vectors drive expression of a transgene in cells. Transgenes, or polynucleotides that encode proteins, such as a nucleic acid encoding therapeutics, are able to be expressed after administration, optionally at therapeutic levels. In some aspects, a recombinant AAV vector comprises a viral genome comprising a transgene, wherein the viral genome comprises two inverted terminal repeat (ITR) sequences from the AAV genome, one on the 3' end and one on the 5' end, are required in the packaged DNA of an AAV gene therapy vector. By way of example, each ITRs may be 145 bp long (with the left ITR and the right ITR being identical). The DNA between the two ITRs can include, but is not limited to, a promoter (with or without enhancer elements), transgene (e.g. gene of interest, therapeutic), polyA, etc.

Accordingly, there are provided recombinant AAV vectors that include (encapsidate, package) vector genomes that include a nucleic acid encoding one or more gene therapies. In particular embodiments, a recombinant AAV particle encapsidates or packages a vector genome. Such recombinant AAV particles include a viral vector genome which includes a heterologous polynucleotide sequence (e.g., nucleic acid encoding a therapeutic). In one embodiment, a vector genome that includes a nucleic acid encoding a desired therapeutic is encapsidated or packaged by an AAV capsid or an AAV capsid variant.

In the recombinant AAV vectors, the heterologous polynucleotide sequence may be transcribed and subsequently translated into a protein. In various aspects, the heterologous polynucleotide sequence encodes a therapeutic protein. In more particular aspects, the vector includes a nucleic acid encoding a therapeutic protein. In some aspects, the therapeutic protein can be any protein encoded by any known gene therapy.

AAV and AAV variants such as capsid variants can deliver polynucleotides and/or proteins that provide a desirable or therapeutic benefit, thereby treating a variety of diseases. For example, AAV1, AAV2, AAV3, AAV4, AAV5, AAV6, AAV7, AAV8, AAV9, AAV10, AAV11, Rh10, Rh74 or AAV-2i8, and variants thereof and AAV capsid variants (e.g., 4-1) are useful vectors to deliver therapeutic genes to cells, tissues and organs.

The recombinant viral and AAV vectors that include (encapsidate, package) a vector genome (viral or AAV) include additional elements that function in cis or in trans. In particular embodiments, a recombinant viral (e.g., AAV) vector that includes (encapsidate, package) a vector genome also comprises: one or more inverted terminal repeat (ITR) sequences that flank the 5' or 3' terminus of the heterologous polynucleotide sequence (e.g., nucleic acid encoding a therapeutic; an expression control element that drives transcription (e.g., a promoter or enhancer) of the heterologous polynucleotide sequence (e.g., nucleic acid encoding a therapeutic protein), such as a constitutive or regulatable control element, or tissue-specific expression control element; an intron sequence, a stuffer or filler polynucleotide sequence; and/or a poly-adenylation sequence located 3' of the heterologous polynucleotide sequence.

Accordingly, vectors can further include an intron, an expression control element (e.g., a constitutive or regulatable control element, or a tissue-specific expression control element or promoter such as for liver expression, e.g., a human al-anti-trypsin (hAAT) Promoter and/or apolipoprotein E (ApoE) HCR-1 and/or HCR-2 enhancer), one or more adeno-associated virus (AAV) inverted terminal repeats (ITRs) (e.g., an ITR sequence of any of: AAV1, AAV2, AAV3, AAV4, AAV5, AAV6, AAV7, AAV8, AAV9, AAV10, AAV11, Rh10, Rh74 or AAV-2i8 AAV serotypes) and/or a filler polynucleotide sequence. Positions of such additional elements can vary. In particular aspects, an intron is within the sequence encoding a therapeutic protein, and/or the expression control element is operably linked to the sequence encoding the therapeutic protein, and/or the AAV ITR(s) flanks the 5' or 3'end of the sequence encoding the therapeutic protein, and/or wherein the filler polynucleotide sequence flanks the 5' or 3'end of the sequence encoding the therapeutic protein.

Exemplary AAV vectors include AAV capsid sequence of any of AAV1, AAV2, AAV3, AAV4, AAV5, AAV6, AAV7, AAV8, AAV9, AAV10, AAV11, Rh10, Rh74 or AAV-2i8, or a capsid variant of AAV1, AAV2, AAV3, AAV4, AAV5, AAV6, AAV7, AAV8, AAV9, AAV10, AAV11, Rh10, Rh74 or AAV-2i8. Recombinant AAV particles disclosed also include AAV1, AAV2, AAV3, AAV4, AAV5, AAV6, AAV7, AAV8, AAV9, AAV10, AAV11, Rh10, Rh74 or AAV-2i8, and variants thereof.

Methods and uses for administration or delivery include any mode compatible with a subject. In particular embodiments, a lenti- or parvo-virus (e.g., AAV) vector such as AAV1, AAV2, AAV3, AAV4, AAV5, AAV6, AAV7, AAV8, AAV9, AAV10, AAV11, Rh10, Rh74 and AAV-2i8, and variants, or plurality of such viral particles is administered or delivered parenterally, such as intravenously, intraarterially, intramuscularly, subcutaneously, or via catheter.

Subjects include mammals, such as humans and non-humans (e.g., primates). In particular embodiments, a subject would benefit from or is in need of expression of a heterologous polynucleotide sequence.

Methods of producing recombinant AAV vectors such as AAV1, AAV2, AAV3, AAV4, AAV5, AAV6, AAV7, AAV8, AAV9, AAV10, AAV11, Rh10, Rh74 and AAV-2i8, and variants, that include (encapsidate, package) vector genome are well known in the art. In one embodiment, a method includes introducing into a packaging cell a recombinant vector (e.g., AAV) plasmid to produce a productive viral infection; and culturing the packaging cells under conditions to produce recombinant viral particles. In another embodiment, a method of producing recombinant viral or AAV particles with reduced amounts of recombinant viral particles in which the recombinant viral vector includes contaminating nucleic acid, includes introducing into a packaging cell a recombinant vector (e.g., AAV) plasmid; and culturing the packaging cells under conditions to produce recombinant viral particles, wherein the recombinant viral particles produced have reduced numbers of viral particles with vector genomes that contain contaminating nucleic acid compared to the numbers of viral particles that contain contaminating nucleic acid produced under conditions in which a filler or stuffer polynucleotide sequence is absent from the recombinant viral vector. In particular aspects, the contaminating nucleic acid is bacterial nucleic acid; or a sequences other than the heterologous polynucleotide sequence, or ITR, promoter, enhancer, origin of replication, poly-A sequence, or selectable marker.

Packaging cells include mammalian cells. In particular embodiments, a packaging cell includes helper (e.g., AAV) functions to package the (heterologous polynucleotide) sequence (e.g., modified nucleic acid encoding a therapeutic), expression vector (e.g., vector genome), into a viral particle (e.g., AAV particle). In particular aspects, a packaging cell provides AAV Rep and/or Cap proteins (e.g., Rep78 or/and Rep68 proteins); a packaging cell is stably or transiently transfected with polynucleotide(s) encoding Rep and/or Cap protein sequence(s); and/or a packaging cell is stably or transiently transfected with Rep78 and/or Rep68 protein polynucleotide encoding sequence(s).

Recombinant AAV vectors, and accompanying cis (e.g., expression control elements, ITRs, polyA,) or trans (e.g., capsid proteins, packaging functions such as Rep/Cap protein) elements can be based upon any organism, species, strain or serotype. Recombinant AAV viral particles may be based upon AAV1, AAV2, AAV3, AAV4, AAV5, AAV6, AAV7, AAV8, AAV9, AAV10, AAV11, Rh10, Rh74 and AAV-2i8, and variants, but also include hybrids or chimeras of different serotypes. Representative AAV serotypes include, without limitation, AAV1, AAV2, AAV3, AAV4, AAV5, AAV6, AAV7, AAV8, AAV9, AAV10, AAV11, Rh10, Rh74 and AAV-2i8 serotypes. Accordingly, recombinant viral (e.g., AAV) particles comprising vector genomes can include a capsid protein from a different serotype, a mixture of serotypes, or hybrids or chimeras of different serotypes, such as a VP1, VP2 or VP3 capsid protein of AAV1, AAV2, AAV3, AAV4, AAV5, AAV6, AAV7, AAV8, AAV9, AAV10, AAV11, Rh10, Rh74 or AAV-2i8 serotype. Furthermore, recombinant lenti- or parvo-virus (e.g., AAV) vectors such as AAV1, AAV2, AAV3, AAV4, AAV5, AAV6, AAV7, AAV8, AAV9, AAV10, AAV11, Rh10, Rh74 and AAV-2i8, sequences, plasmids, vector genomes, can include elements from any one serotype, a mixture of serotypes, or hybrids or chimeras of different serotypes. In various embodiments, a recombinant AAV vector includes a, ITR, Cap, Rep, and/or sequence derived from AAV1, AAV2, AAV3, AAV4, AAV5, AAV6, AAV7, AAV8, AAV9, AAV10, AAV11, Rh10, Rh74 and/or AAV-2i8 serotype, or a mixture, hybrid or chimera of any of the foregoing AAV serotypes.

As set forth herein, viral vectors such as AAV vectors provide a means for delivery of polynucleotide sequences into cells ex vivo, in vitro and in vivo, which can encode proteins such that the cells express the encoded proteins. For example, a recombinant AAV vector can include a heterologous polynucleotide encoding a desired protein or peptide. Vector delivery or administration to a subject (e.g., mammal) therefore provides encoded proteins and peptides to the subject. Thus, viral vectors such as AAV vectors, can be used to transfer/deliver heterologous polynucleotides for expression, and optionally for treating a variety of diseases.

In particular embodiments, a recombinant vector (e.g., AAV) is a parvovirus vector. Parvoviruses are small viruses with a single-stranded DNA genome. "Adeno-associated viruses" (AAV) are in the parvovirus family.

Parvoviruses including AAV are viruses useful as gene therapy vectors as they can penetrate cells and introduce nucleic acid/genetic material so that the nucleic acid/genetic material may be stably maintained in cells. In addition, these viruses can introduce nucleic acid/genetic material into specific sites, for example, such as a specific site on chromosome 19. Because AAV are not associated with pathogenic disease in humans, AAV vectors are able to deliver heterologous polynucleotide sequences (e.g., therapeutic proteins and agents) to human patients without causing substantial AAV pathogenesis or disease.

AAV and AAV variants (e.g., capsid variants such as 4-1) serotypes (e.g., VP1, VP2, and/or VP3 sequences) may or may not be distinct from other AAV serotypes, including, for example, AAV1-AAV11, Rh74 or Rh10 (e.g., distinct from VP1, VP2, and/or VP3 sequences of any of AAV1-AAV11, Rh74 or Rh10 serotypes).

Methods and uses disclosed provide a means for delivering (transducing) heterologous polynucleotides (transgenes) into host cells, including dividing and/or non-dividing cells. The recombinant vector (e.g., rAAV) sequences, vector genomes, recombinant virus particles, methods, uses and pharmaceutical formulations disclosed are additionally useful in a method of delivering, administering or providing a nucleic acid, or protein to a subject in need thereof, as a method of treatment. In this manner, the nucleic acid is transcribed and the protein may be produced in vivo in a subject. The subject may benefit from or be in need of the nucleic acid or protein because the subject has a deficiency of the nucleic acid or protein, or because production of the nucleic acid or protein in the subject may impart some therapeutic effect, as a method of treatment or otherwise.

In general, recombinant AAV vector sequences, vector genomes, recombinant virus particles, methods and uses may be used to deliver any heterologous polynucleotide (transgene) with a biological effect to treat or ameliorate one or more symptoms associated with any disorder related to insufficient or undesirable gene expression. Recombinant AAV vector sequences, plasmids, vector genomes, recombinant virus particles, methods and uses may be used to provide therapy for various disease states.

Disclosed herein are nucleic acids, vectors, recombinant vectors (e.g., rAAV), vector genomes, and recombinant virus particles, methods and uses that permit the treatment of genetic diseases. In general, disease states fall into two classes: deficiency states, usually of enzymes, which are generally inherited in a recessive manner, and unbalanced states, at least sometimes involving regulatory or structural proteins, which are inherited in a dominant manner. For deficiency state diseases, gene transfer could be used to bring a normal gene into affected tissues for replacement therapy, as well as to create animal models for the disease using antisense mutations. For unbalanced disease states, gene transfer could be used to create a disease state in a model system, which could then be used in efforts to counteract the disease state. The use of site-specific integration of nucleic acid sequences to correct defects is also possible.

In accordance with the invention, treatment methods and uses are provided that include invention nucleic acids, vectors, recombinant vectors (e.g., rAAV), vector genomes, and recombinant virus particles. Methods and uses of the invention are broadly applicable to providing, or increasing or stimulating, gene expression or function, e.g., gene addition or replacement.

C. Methods of Producing Viral Vectors

Disclosed herein are methods for producing viral vectors. By way of example, methods for producing viral vectors may comprise creation of plasmids, transformation, selection, amplification and extraction of plasmid DNA, transfection into producer cells, production of viral vectors, harvesting and purification, and quality control.

The first step involves the creation of plasmids, which are small, circular pieces of DNA that can replicate independently of the chromosomal DNA in a bacterium. The plasmid DNA is engineered to carry the transgene of interest along with other necessary elements. These may include a strong promoter for expression of the transgene, an antibiotic resistance gene for the selection of successfully transformed bacterial cells, and sequences necessary for replication and packaging of the viral genome.

Once the plasmid carrying the transgene has been created, the plasmid is then introduced into *E. coli* using a process known as transformation. This can be achieved by various methods such as heat shock or electroporation which make the bacterial cell walls permeable to the plasmid DNA.

Following transformation, the *E. coli* cells are cultured on a growth medium containing a specific antibiotic. Only the cells that have taken up the plasmid, and therefore the antibiotic resistance gene, can survive and proliferate in this environment. This process effectively selects for the transformed cells.

The selected bacterial cells are grown in larger volumes to amplify the plasmid DNA. The cells are then lysed (broken open) and the plasmid DNA is purified from the cell debris using various extraction and purification procedures.

The purified plasmid DNA is then transfected into a line of producer cells (e.g., a mammalian cell line), where the viral vector production will occur. This may be achieved using chemical, physical or viral methods. For example, calcium phosphate precipitation or lipofection can be used for chemical methods, electroporation for physical methods, and lentivirus or adenovirus can be used for viral methods.

Inside the producer cells, the viral sequences contained in the plasmid DNA are transcribed and translated, leading to the production of viral proteins. These proteins then self-assemble into viral particles, packaging the transgene into their genomes in the process.

The viral vectors carrying the transgene are harvested from the producer cells and then purified using methods such as ultracentrifugation or column chromatography.

Finally, one or more quality control procedures may be performed. For example, the viral vectors may be tested for transduction efficiency (ability to deliver the transgene into target cells), safety (absence of replication-competent viruses and residual producer cells), and purity.

Quality control processes are important as the hairpin structure and high GC content (e.g., 70%) of ITRs contributes to the instability of ITR-containing plasmids. One or more quality control assays may be performed including, but not limited to, XmaI digests, agarose gel electrophoresis, capillary electrophoresis, Sanger sequencing, and/or AAV-ITR sequencing. XmaI digests (CCCGGG) are traditionally done to check for ITR integrity. Agarose gel electrophoresis results in qualitative size separation and indicates the presence, but not the nature of, ITR mutations. Capillary electrophoresis (CE) results in size separation and quantitation (peak area calculation), but does not reveal the nature of any ITR mutation. Sanger sequencing cannot reliably sequence through the ITR structure. AAV-ITR sequencing requires the mutated species to be at some threshold for reliable detection and cannot quantify the relative amounts of variants present in sample.

Provided herein are quality control process utilizing next generation sequencing (NGS) techniques. Without being limited by any theory in particular, the provided NGS quality control techniques provide greater depth than Sanger sequencing, can quantify variants present in the plasmid pool, and can identify major and minor variants.

Figure 3:
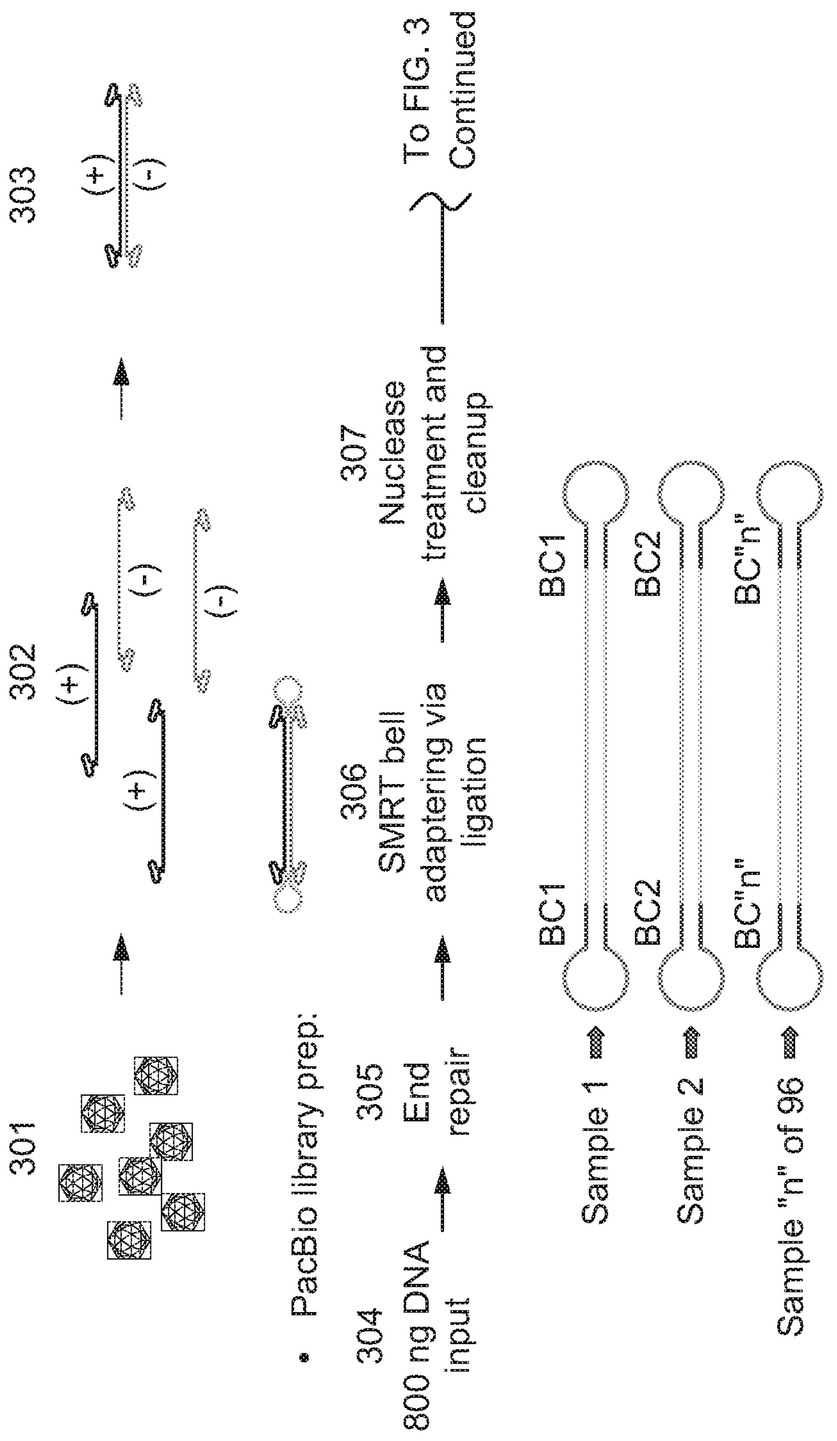
FIG. 3 provides an overview of sample preparation prior to next generation sequencing.
Figure 3:
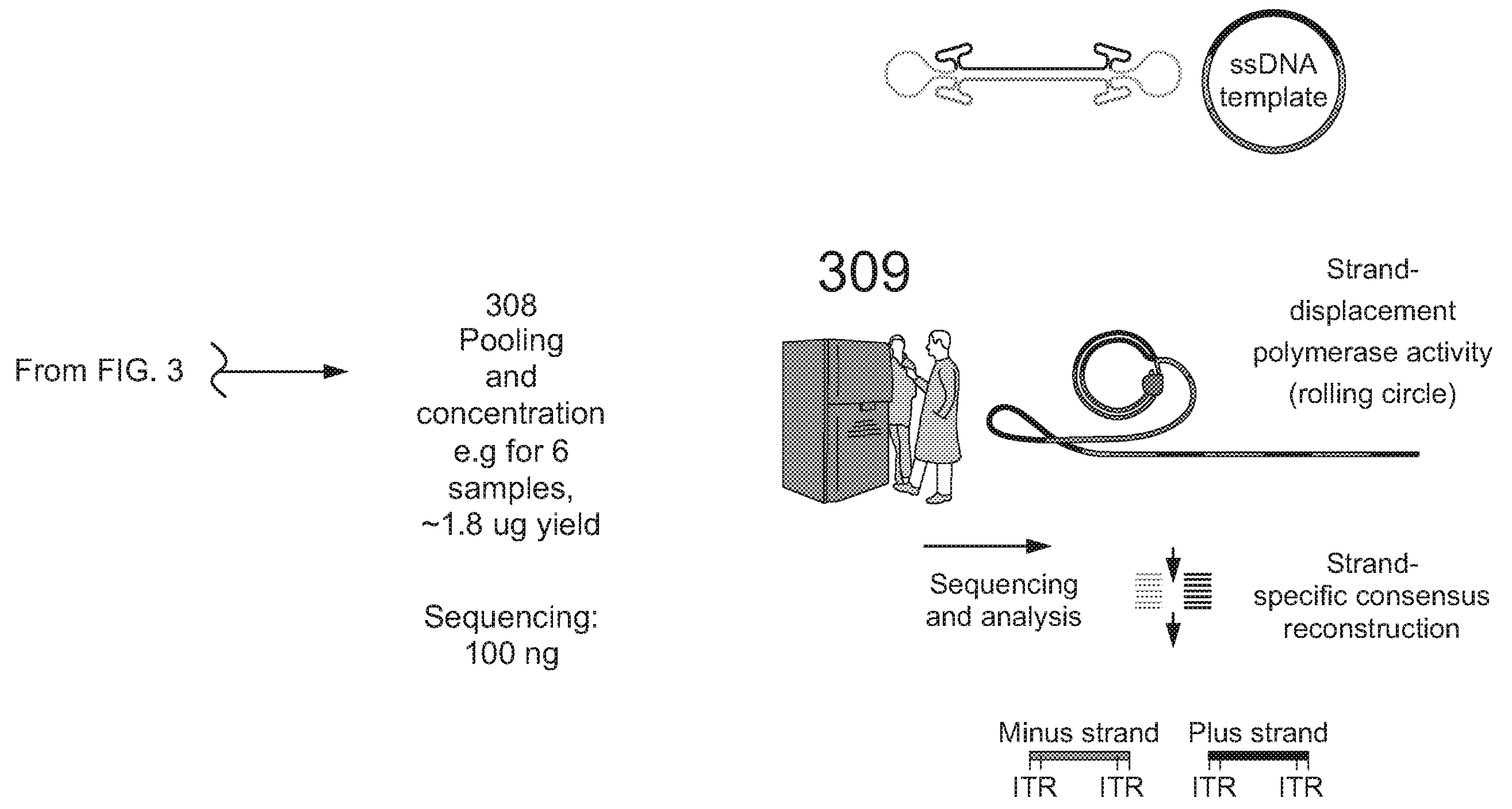

NGS quality control techniques may be performed to identify ITR sequence variations in AAV-ITR packaging plasmid and/or recombinant AAV samples. FIG. 3 provides an overview of sample preparation prior to next generation sequencing. In brief, sample preparation is conducted as described below.

For samples containing AAV-ITR packaging plasmids (not shown), the plasmid is first linearized by digesting with a restriction endonuclease that does not recognize cleavage sites within the ITR-genetic payload-ITR region of the packaging plasmid. The linearized, double-stranded packaging plasmid DNA sample is then purified using commercially-available methods, such as column purification. In some embodiments, 1 microgram of AAV-ITR packaging plasmid is linearized as described above.

For recombinant AAV samples, the AAV sample is first treated with DNase to remove unencapsidated DNA contaminants at step 301. Next, the AAV sample is treated with Proteinase K to release viral genomic sequences at step 302. The viral genomic sequences, which include both + and − strands, are then purified using commercially-available methods, such as column purification. The purified + and − viral genomic strands are then annealed to produce a sample of double-stranded DNA molecules that includes the ITR-genetic payload-ITR region of the recombinant AAV genome at step 303. In some embodiments, an AAV sample containing about $1\times10^{12}$ viral genomes serves as the starting material for the steps described above.

Double-stranded DNA samples prepared from AAV-ITR packaging plasmids or recombinant AAV samples (as described above) are then used to create PacBio® sequencing libraries using SMRTbell™ adapters, according to the manufacturer's instructions. In some embodiments, 800 nanograms of double-stranded DNA sample serves as the starting material for sequencing library generation at step 304, but other quantities are contemplated. In brief, the double-stranded DNA sample is first subjected to end repair at step 305 (for example, using the PacBio® Template Prep Kit) in preparation for ligation with SMRTbell™ adapters at step 306, and purified prior to ligation (for example, using AMPure® PB bead purification). Blunt-ended SMRTbell™ adapters are then attached to the repaired ends of the double-stranded DNA sample using blunt-end ligation, according to the manufacturer's instructions. Single-stranded exonuclease treatment is then performed at step 307 to remove any failed ligation products, and the sample is purified (for example, using AMPure® PB bead purification). Samples are then pooled and concentrated at step 308 prior to next generation PacBio® sequencing at step 309. In some embodiments, 100 nanograms of pooled, concentrated sample is used for next generation PacBio® sequencing.

D. Methods of Identifying ITRs

In some aspects, it can be challenging to accurately genotype the ITR regions with existing genotyping technologies for several reasons: high GC content; secondary structure (hairpin); and reverse complementary sequences of the left and right ITRs (L-ITRs and R-ITRs, respectively). High GC content can be a hindrance for library prep workflows that require a PCR reaction, as high GC content DNA is harder to 'unzip' for PCR amplification. High GC content DNA is also a hindrance for some sequencing approaches. In some aspects, the secondary structure (e.g., hairpin) can be an issue because for sequence-by-synthesis methodologies the polymerase might not be able to sequence through ITR sequences. Lastly, the reverse complementary nature of the L-ITR and R-ITR can pose problems during alignment of both WT reads and reads carrying the variants. Short read sequencing cannot distinguish the L-ITR from the R-ITR, because alignment software are written for double-stranded DNA and expect both left and right ITR sequences to map to the same locus. Additionally, several different variants could lead to the same DNA motif that short read sequencing was unable to correctly map to the left or the right locus.

Some problems with genotyping technologies are not locus-specific, for instance, long-read sequencing generally produces noisy reads, which might lead to inaccurate variant calling. Even when reads are both long and accurate, conventional analysis tools are largely written for noisy reads, which can be problematic.

In some aspects, not just sequencing but also bioinformatics difficulties can cause problems in genotyping ITRs. Even with long and accurate reads, conventional variant calling tools are unable to call ITR variants accurately. Two types of variants are particularly problematic—ITR insertions at the end of reference genomes and overlapping deletions (by reference coordinates) in different molecules. For ITR insertions, conventional alignment software 'soft-clips' the excess ITR insertion, and the downstream variant caller software ignore it. For overlapping deletions, the alignment seems accurate, but the variant callers homogenize the signal as opposed to calling multiple deletions. Therefore, many variants are missed.

Because of these challenges, technological improvements in genotyping of ITRs are necessary. These new methods disclosed herein comprise solutions to overcome the previous sequencing and bioinformatics problems discussed above. The conventional alignment plus variant calling approach was circumvented at least by extracting relevant sequences using fixed flanking sequence markers directly from the raw sequencer data. The conventional alignment plus variant calling approach was circumvented at least by sorting the obtained sequences by abundance, thus clustering them by identity. The conventional alignment plus variant calling approach was circumvented at least by using local alignment to characterize the obtained sequence. In some aspects, the methods disclosed herein differ from, and hereby improve, the previously known approaches because there is no risk of homogenizing the signal coming from multiple molecules, as they all exist in separate 'clusters', and variants are called in each cluster independently, as explained in greater detail herein.

In some aspects, disclosed are systems, devices, methods of identifying the ITRs in the plasmids used to produce AAV or adenoviral vectors and methods of identifying the ITRs in the viral genomes of the AAV or adenoviral vectors produced. In some aspects, the disclosed methods can be performed on sequencing data associated with any viral vectors comprising ITRs in their genome, including but not limited to AAV vectors and adenovirus vectors. The methods described herein are directed to AAV vectors and their ITRs but the same methods can be used to identify ITRs in adenoviral vectors (or plasmids used to produce adenoviral vectors).

1. ITRs in Plasmids

Figure 18:
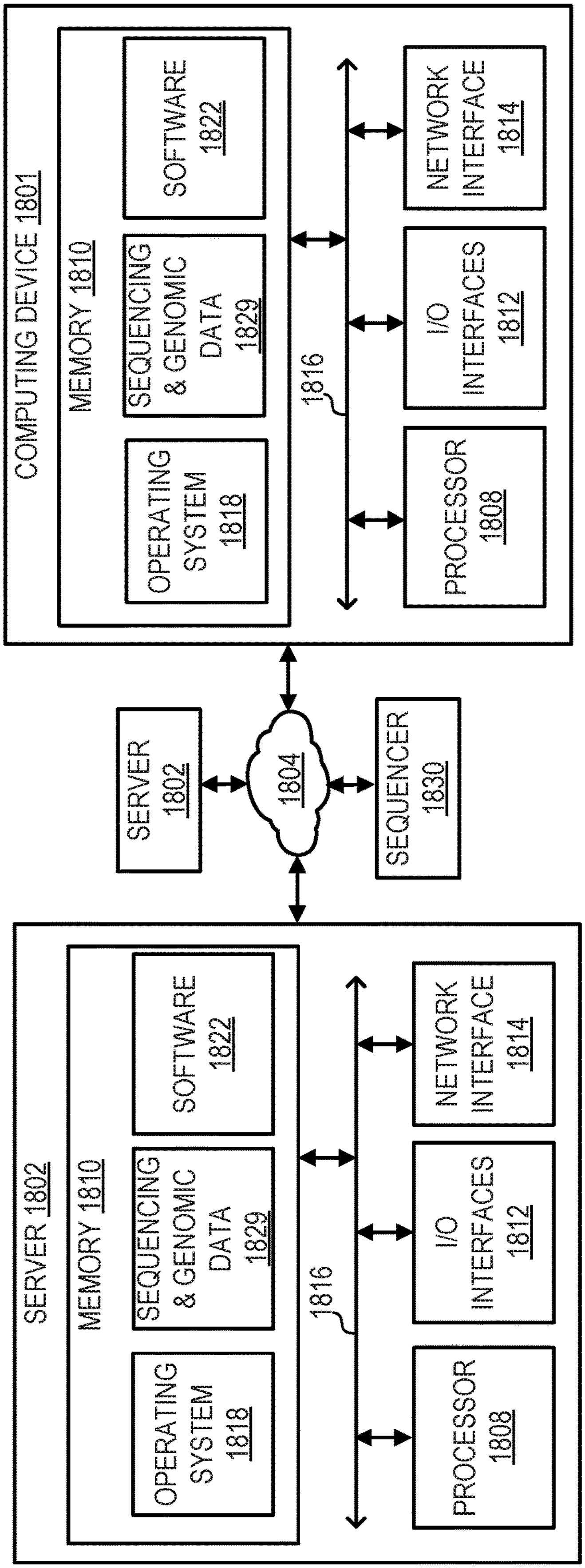
FIG. 18 shows an example operating environment.

Aspects of the methods disclosed herein can be performed at least in part by the system 1800 of FIG. 18.

Disclosed are methods comprising sequencing (e.g., by the sequencer 1830 and/or other sequencing apparatus(es) communicably coupled to the device 1801 and/or the server 1802) genomes of a plurality of plasmids to obtain a plurality of plasmid genome sequences; receiving (e.g., by the processor 1808) a specification of a fixed flanking sequence marker; extracting (e.g., by the processor 1808), from each plasmid genome sequence, based on the presence of the fixed flanking sequence markers in that plasmid genome sequence, a plurality of sequence regions, wherein each sequence region is within the fixed flanking sequence markers and comprises a candidate ITR sequence; clustering (e.g., by the processor 1808), based on perfect sequence identity, two or more sequence regions of the plurality of sequence regions to generate a plurality of clusters; merging (e.g., by the processor 1808), based on an alignment between their corresponding sequence regions, two or more clusters of the plurality of clusters; and deeming the plurality of plasmids unsuitable for production of recombinant vector genomes, after the merging, if two or more clusters remain.

Disclosed are methods comprising sequencing (e.g., by the sequencer 1830 and/or other sequencing apparatus(es) communicably coupled to the device 1801 and/or the server 1802) genomes of a plurality of plasmids to obtain a plurality of plasmid genome sequences; receiving (e.g., by the processor 1808) a specification of a fixed flanking sequence marker; extracting (e.g., by the processor 1808), from each plasmid genome sequence, based on the presence of the fixed flanking sequence markers in the plasmid genome sequence, a plurality of sequence regions, wherein each sequence region is within the fixed flanking sequence markers and comprises a candidate ITR sequence; clustering (e.g., by the processor 1808), based on perfect sequence identity, the two or more sequence regions of the plurality of sequence regions to generate a plurality of clusters; merging (e.g., by the processor 1808), based on an alignment between their corresponding sequence regions, two or more clusters of the plurality of clusters; and when a single cluster remains, after said merging identifying, based on a local alignment, a genotype of a candidate ITR sequence of the representative sequence.

In some aspects, a plurality of plasmids from different batches of plasmid can be tested to determine the genotype/identity of the ITRs in the plasmid genome. In the end, each batch can be determined to be accepted or rejected for continued use of producing AAV vectors.

Disclosed are methods comprising sequencing (e.g., by the sequencer 1830 and/or other sequencing apparatus(es) communicably coupled to the device 1801 and/or the server 1802) genomes of a plurality of plasmids, from two or more batches of plasmids, to obtain a plurality of plasmid genome sequences from each batch of plasmids; receiving (e.g., by the processor 1808) a specification of a fixed flanking sequence marker; extracting (e.g., by the processor 1808), from each plasmid genome sequence, based on the presence of the fixed flanking sequence markers in the plasmid sequence, a plurality of sequence regions, wherein each sequence region is within the fixed flanking sequence markers and comprises a candidate ITR sequence; clustering (e.g., by the processor 1808), based on perfect sequence identity, two or more sequence regions of the plurality of sequence regions to generate a plurality of clusters; merging (e.g., by the processor 1808), based on an alignment between their corresponding sequence regions, two or more clusters of the plurality of clusters; wherein if two or more clusters remain after merging for at least one batch of plasmids, rejecting that batch of plasmids for further use in producing AAV vectors, wherein if a single cluster remains for at least one batch of plasmids, identifying, based on a local alignment, a genotype of a candidate ITR sequence of the representative sequence, wherein if the candidate ITR is identical (or in some embodiments, substantially identical) to a reference AAV ITR (e.g., wild type AAV ITR and/or an engineered AAV ITR) then accept the use of that batch of plasmids to produce AAV vectors.

Figure 4:
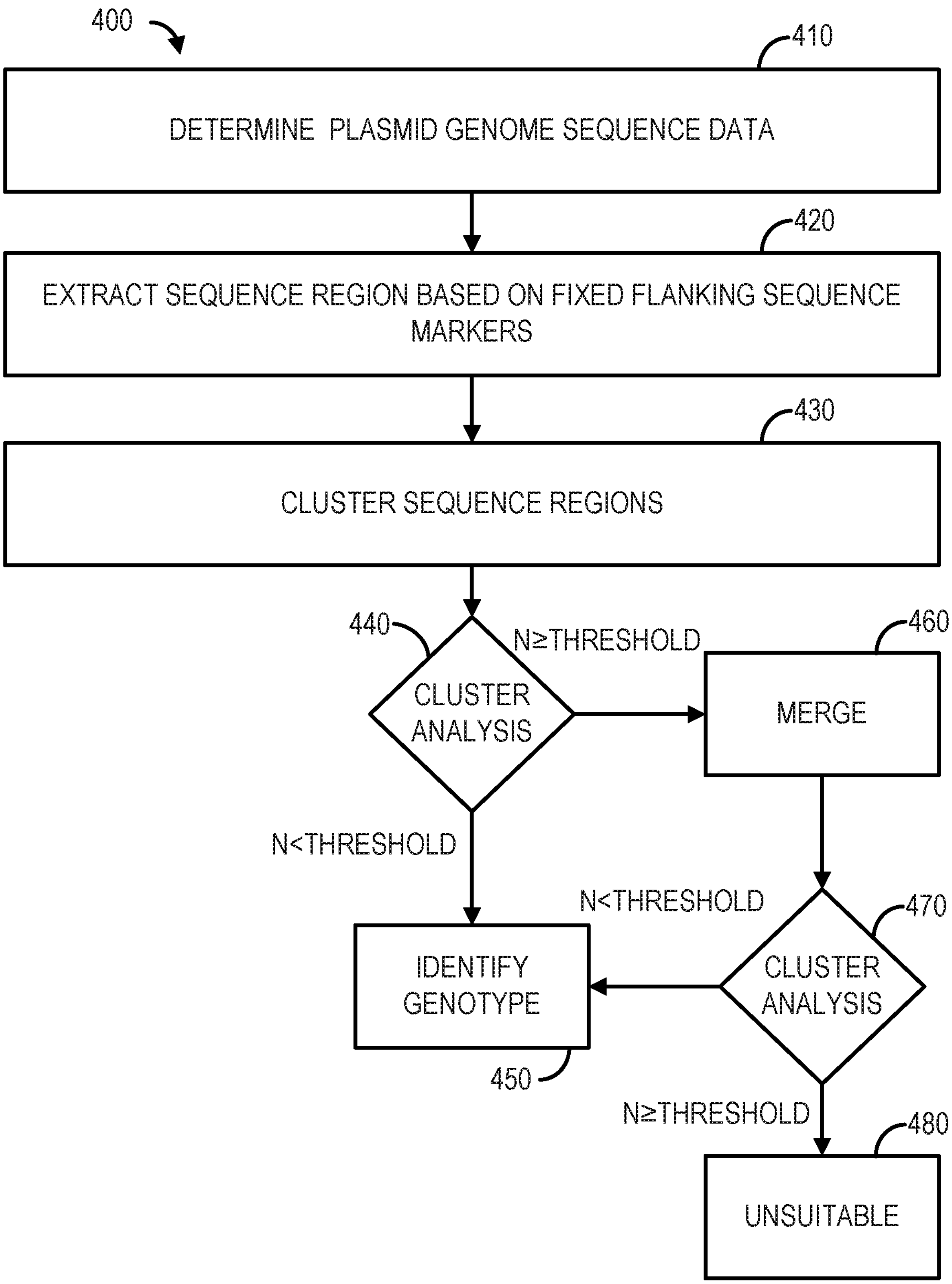
FIG. 4 shows an example method of ITR genotyping.

As shown in FIG. 4, provided are methods, devices (e.g., the device 1801 in FIG. 18), and systems (e.g., the system 1800 in FIG. 18) for identifying genotypes of inverted terminal repeats (ITRs) in plasmids used to produce AAV vectors.

Disclosed is a method 400 comprising determining, at step 410, plasmid genome sequence data. The plasmid genome sequence data may comprise a plurality of plasmid genome sequences. The plurality of plasmid genome sequences may be sequences from a plurality of plasmids. Determining plasmid genome sequence data may comprise sequencing (e.g., by the sequencer 1830 and/or other sequencing apparatus(es) communicably coupled to the device 1801 and/or the server 1802) genomes of a plurality of plasmids to obtain a plurality of plasmid genome sequences. Determining plasmid genome sequence data may comprise receiving the plasmid genome sequence data.

In some aspects, the sequencing comprises sequencing genomes of a plurality of plasmids to obtain a plurality of plasmid genome sequences. In some aspects, the sequencing comprises sequencing AAV vector genomes, from a plurality of AAV vectors, to obtain a plurality of AAV vector genome sequences.

Disclosed are methods for sequencing plasmid genomes and AAV vector genomes. Plasmid genomes and/or AAV vector genomes can be sequenced and analyzed as a part of the AAV vector production quality control process.

In some aspects, plasmids and/or AAV vectors can first be purified or isolated before sequencing the genomes. In some aspects, AAV capsids can be purified and nucleotides outside the AAV capsids can be eliminated, leaving only nucleotides inside the AAV capsids. The AAV capsids can be denatured to obtain the nucleotides within the AAV capsids. The plasmid genomes or AAV vector genomes can be subjected to one or more DNA sequencing techniques. Sequencing methods executable by the sequencer 1830 can include, for example, long read sequencing and/or circular consensus sequencing (CCS). Other sequencing methods or commercially available formats that are optionally utilized include, for example, Sanger sequencing, high-throughput sequencing, bisulfite sequencing, pyrosequencing, sequencing-by-synthesis, single-molecule sequencing, nanopore-based sequencing, semiconductor sequencing, sequencing-by-ligation, sequencing-by-hybridization, RNA-Seq (Illumina), Digital Gene Expression (Helicos), next generation sequencing (NGS), Single Molecule Sequencing by Synthesis (SMSS) (Helicos), massively-parallel sequencing, Clonal Single Molecule Array (Solexa), shotgun sequencing, Ion Torrent, Oxford Nanopore, Roche Genia, Maxim-Gilbert sequencing, primer walking, sequencing using PacBio, SOLiD, Ion Torrent, or nanopore platforms. Sequencing reactions can be performed in a variety of sample processing units, which may include multiple lanes, multiple channels, multiple wells, or other means of processing multiple sample sets substantially simultaneously. Sample processing units can also include multiple sample chambers to enable the processing of multiple runs simultaneously.

In some aspects, sequencing the plurality of AAV genomes comprises sequencing via long read sequencing. In some aspects, long read sequencing generates sequences 1 kb, 2 kb, 3 kb, 4 kb, 5 kb, 6 kb, 7 kb, 8 kb, 9 kb, 10 kb or greater in length.

In some aspects, the methods can further comprise, after the sequencing step, a step of receiving (e.g., by the processor 1808) a specification of a fixed flanking sequence marker.

The method 400 may comprise extracting one or more sequence regions from the plasmid genome sequence data at step 420. Extracting one or more sequence regions from the plasmid genome sequence data may comprise extracting a plurality of sequence regions from each plasmid genome sequence in the plasmid genome sequence data. A sequence region may comprise a candidate ITR sequence. Extracting the one or more sequence regions (or the plurality of sequence regions) from the plasmid genome sequence data may be based on a fixed flanking sequence marker. Extracting the one or more sequence regions from the plasmid genome sequence data may comprise receiving a specification of the fixed flanking sequence marker. Extracting one or more sequence regions from the plasmid genome sequence data may comprise extracting, from each plasmid genome sequence, based on the presence of the fixed flanking sequence markers in that plasmid sequence, a plurality of sequence regions, wherein each sequence region is within the fixed flanking sequence markers and comprises a candidate ITR sequence.

Figure 5A:
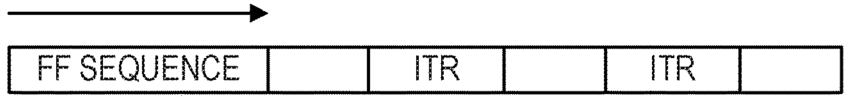
FIGS. 5A-5D show example fixed flanking sequence marker methods.
Figure 5B:
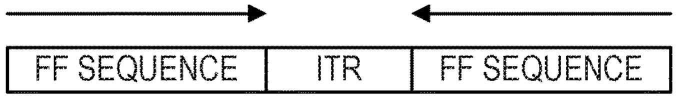
Figure 5C:

As illustrated in FIG. 5A, the extraction may be accomplished, for example, by analyzing and/or locating positions of the fixed flanking sequence markers in the plasmid genome sequence data and extracting some or all positions from the fixed flanking sequence markers to an end of the plasmid genome sequence. As illustrated in FIG. 5B and FIG. 5C, the extraction may be accomplished, for example, by analyzing positions of the fixed flanking sequence markers in the plasmid genome sequence data and extracting some or all positions in between fixed flanking sequence markers. The result of the extraction may be a sequence region that may be stored as a string or other data structure.

In some aspects, plasmid genome sequences comprise fixed flanking sequence markers which are present on both ends of a candidate ITR sequence. In some aspects, fixed flanking sequence markers may comprise sequences of the plasmid genome that are known and flank the candidate ITR sequence. In some aspects, multiple regions having the fixed flanking sequence marker can be indicative that the sequence region comprising the fixed flanking sequence has a mutation (e.g., concatemerized) and therefore a different fixed flanking sequence marker can be used or that sequence region can be discarded from subsequent analysis. The fixed flanking sequence marker may comprise a sequence of at least 10 nucleotides.

Because plasmid genomes are circular, every sequence region within the plasmid genome, including the sequence region comprising a candidate ITR, is flanked with sequences on either side. Thus, in some aspects, extracting a sequence region (e.g. a candidate ITR sequence) from a plasmid comprises extracting the sequence region between two fixed flanking sequence markers.

In some aspects, the plasmid genomes, which are used for producing AAV vectors, comprise a sequence having a first ITR, a transgene (or gene of interest), and a second ITR. In some aspects, this sequence comprising a first ITR, a transgene (or gene of interest), and a second ITR can be referred to as the viral genome sequence region because this is the region that can get packaged as the viral genome upon production of an AAV vector. The remaining portion of the plasmid genome is referred to as the plasmid backbone, which is a known sequence.

In some aspects, because the transgene is known, a portion of the transgene sequence can be used as a fixed flanking sequence marker. For example, the 5' end of the transgene, which is adjacent to the 3' end of the first ITR, can be used as a fixed flanking sequence marker. A portion of the plasmid backbone, which is adjacent to the 5' end of the first ITR, can also be used as a fixed flanking sequence marker. Similarly, for the second ITR, the 3' end of the transgene, which is adjacent to the 5' end of the second ITR, can be used as a fixed flanking sequence marker and a portion of the plasmid backbone, which is adjacent to the 3' end of the second ITR, can also be used as a fixed flanking sequence marker. Thus, there can be a fixed flanking sequence marker on the 5' and 3' ends of each ITR. In some aspects, the fixed flanking sequence markers can be known sequences in the plasmid backbone and/or known sequences in the transgene.

In some aspects, the fixed flanking sequence markers can be predetermined. For example, the plasmid genome can be created (or picked) based on specific markers in the plasmid backbone or a specific transgene to be present in the plasmid genome that can be used as a fixed flanking sequence marker. Thus, in some aspects, even before sequencing, the fixed flanking sequence markers that will be used for extracting are known and can be provided as input to the device 1801.

In some aspects, because the plasmid genome is circular, each candidate ITR is flanked on either end by fixed flanking sequence markers and the sequence in between the fixed flanking sequence markers can be extracted.

In some aspects, extracting allows for determining a length of the sequence region. In some aspects, the method comprises discarding the sequence region if the length is above a first threshold or below a second threshold. In some aspects, the first threshold is about 300 base pairs long and the second threshold is zero, about 3 base pairs, about 10 base pairs, about 50 base pairs, about 100 base pairs, about 150 base pairs long or more. In some aspects, the method comprises discarding the sequence region if the length is outside of the range of about 80 bp to about 250 bp. In some aspects, the sequence region can be between 100 bp and 130 bp. For example, in some aspects, the sequence region comprises a candidate ITR which can be about 101 bp (e.g., both hairpin structures of the ITR are deleted), thus, if the length of the sequence region is not at least 101 bp it can be discarded. In some aspects, discarding the sequence region based on length can mean that no further steps after the extracting step need to be performed. In some aspects, if the length is 300 bp or greater then this could be indicative that there are duplicate ITRs present and the sequence region should be discarded. In some aspects, a sequence region having a length outside of the described ranges is further analyzed using the claimed method. In some aspects, the sequence regions having a length outside of the range can provide meaningful information such as, for example, on problems with the manufacturing process. In some aspects, the step of determining the length of the sequence region can be performed immediately after sequencing and before extracting.

The step of extracting may be different depending on whether the extracting is from plasmid genome sequencing or AAV vector genome sequencing.

Returning to FIG. 4, the one or more extracted sequence regions may be clustered at step 430. Clustering the one or more sequence regions may comprise aligning the sequence regions comprising the candidate ITRs. Clustering may be based on sequence identity. In an aspect, the sequence regions may be clustered based on perfect sequence identity. In some aspects, perfect identity means 99% sequence identity or higher such as, for example, at least 99.5% sequence identity. For example, sequence regions that share 100% sequence identity may be clustered together. One or more clusters may be generated. In some aspects, a single cluster can be formed, wherein all extracted sequence regions are identical. In some aspects, a plurality of clusters can be formed.

If all of the extracted sequence regions have the same identity, then only one cluster (or group) will be formed. However, for as many sequence identities as there are, there will be an equivalent number of clusters. For example, if there are 100 sequence regions extracted and 70 sequence regions have perfect identity, then those 70 extracted sequence regions can be clustered together. If another 20 sequence regions have a different sequence identity to those 70 but are identical to each other, those 20 sequence regions can be clustered together. If the remaining 10 sequence regions have a different sequence identity to the 70 clustered together and to the 20 clustered together, but are identical to each other, those 10 sequence regions can be clustered together. Thus, in this example, there are 3 sequence identities and therefore, 3 clusters (one for each identity).

In some aspects, a cluster can comprise 1, 10, 50, 100, 500, 1000 or more extracted sequence regions. In some aspects, a cluster can comprise a single sequence region. For example, if all of the extracted sequence regions had perfect identity to at least one other sequence region except one extracted sequence region did not match any other sequence regions, that sequence region would form a cluster by itself.

The method 400 may then perform a cluster analysis at step 440. At step 440, the number of clusters may be compared to a threshold. If the number of clusters does not satisfy the threshold, then the sequence represented by the cluster may be compared to a reference sequence to identify the genotype of the candidate ITR at step 450. For example, the threshold may be 2. Accordingly, in some aspects, if only a single cluster is formed (because all of the sequences had perfect identity), the candidate ITR sequence representative of the single cluster can be compared to a reference sequence. The reference sequence may be a reference ITR sequence. The reference ITR sequence may be, for example, a wild type ITR sequence, an engineered ITR sequence, or any other biologically functional ITR sequence. If the candidate ITR sequence and the reference sequence are identical (or in some embodiments, substantially identical), the candidate ITR is a match and thus can be used to produce AAV vectors comprising a viral genome comprising the reference sequence (e.g., the wild type ITR sequence and/or the engineered ITR sequence). In some aspects, identifying the genotype of the candidate ITR can be based on an alignment, for example a local alignment.

Figure 6:
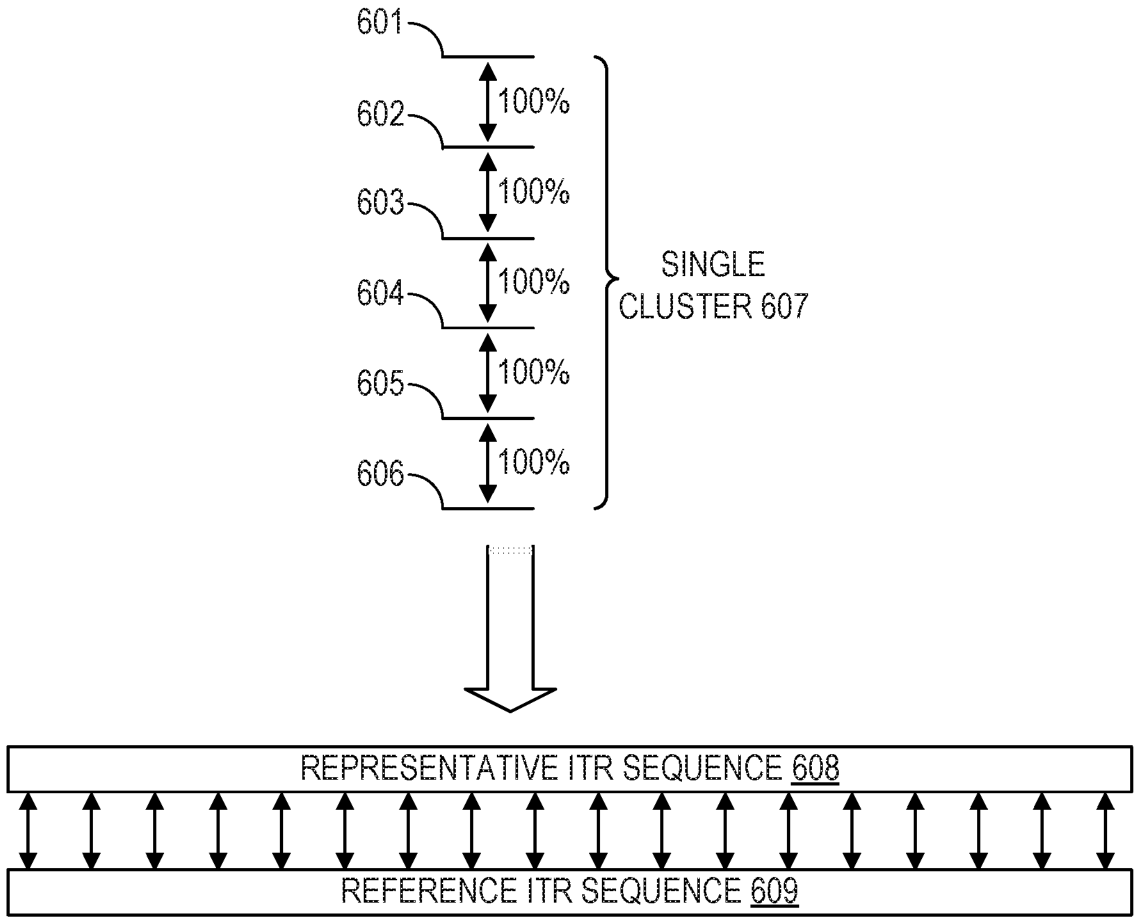
FIG. 6 shows an example method of clustering sequence regions for comparison of a candidate sequence region to a reference sequence.

As shown in FIG. 6, each of the sequence regions 601, 602, 603, 604, 605, and 606 have been determined to have 100% sequence identity to one another, thus forming a single cluster 607. As there is only the single cluster 607, a representative ITR sequence 608 from the single cluster 607 may be compared (e.g., aligned, mapped, etc.) against a reference ITR sequence 609. The reference ITR sequence 609 may be, for example, a wild type ITR sequence, an engineered ITR sequence, or any other biologically functional ITR sequence. If the representative ITR sequence 608 matches the reference ITR sequence 609, then the plasmids may be genotyped as the reference ITR sequence 609. In some aspects, at step 450, the candidate ITR genotype may be identified by aligning (e.g., mapping) the candidate ITR sequence representing the cluster to the reference ITR sequence 609 using one or more sequence alignment methods. The method 400 may leverage a variety of sequence alignment methods. Examples of such methods include BLAST, which quickly locates regions of local similarity, and Clustal, which is beneficial for simultaneous multiple sequence alignments. The Smith-Waterman algorithm offers high precision for short sequences through rigorous local alignment, while the Needleman-Wunsch algorithm is suitable for global sequence alignment and can pinpoint regions of perfect sequence identity for clustering. Additionally, the MUSCLE (Multiple Sequence Comparison by Log-Expectation) algorithm may be employed, known for its speed and effectiveness in handling large datasets, making it particularly useful for high-throughput sequencing data.

Thus, in some aspects, the genotype of the candidate ITR sequence is identical (or in some embodiments, substantially identical) to a reference ITR sequence (e.g., a wild type ITR sequence and/or an engineered ITR sequence). The method 400 may then accept the plasmids. Accepting the plasmids means deeming the plurality of plasmids suitable for production of recombinant vector genomes.

If at step 440, the cluster analysis indicates that the number of clusters satisfies a threshold, the method 400 may proceed to a merging step 460. The number of clusters may satisfy the threshold by, for example, equaling or exceeding the threshold.

The method 400 may merge two or more clusters at step 460. In some aspects, merging two or more clusters can be based on sequence alignment. In some aspects, the two or more clusters have at least a single variant between their sequences. In some aspects, the methods comprise merging, based on an alignment between their corresponding sequence regions, two or more clusters of the plurality of clusters. In some aspects, merging may generate a modified plurality of clusters or a modified cluster.

Figure 7:
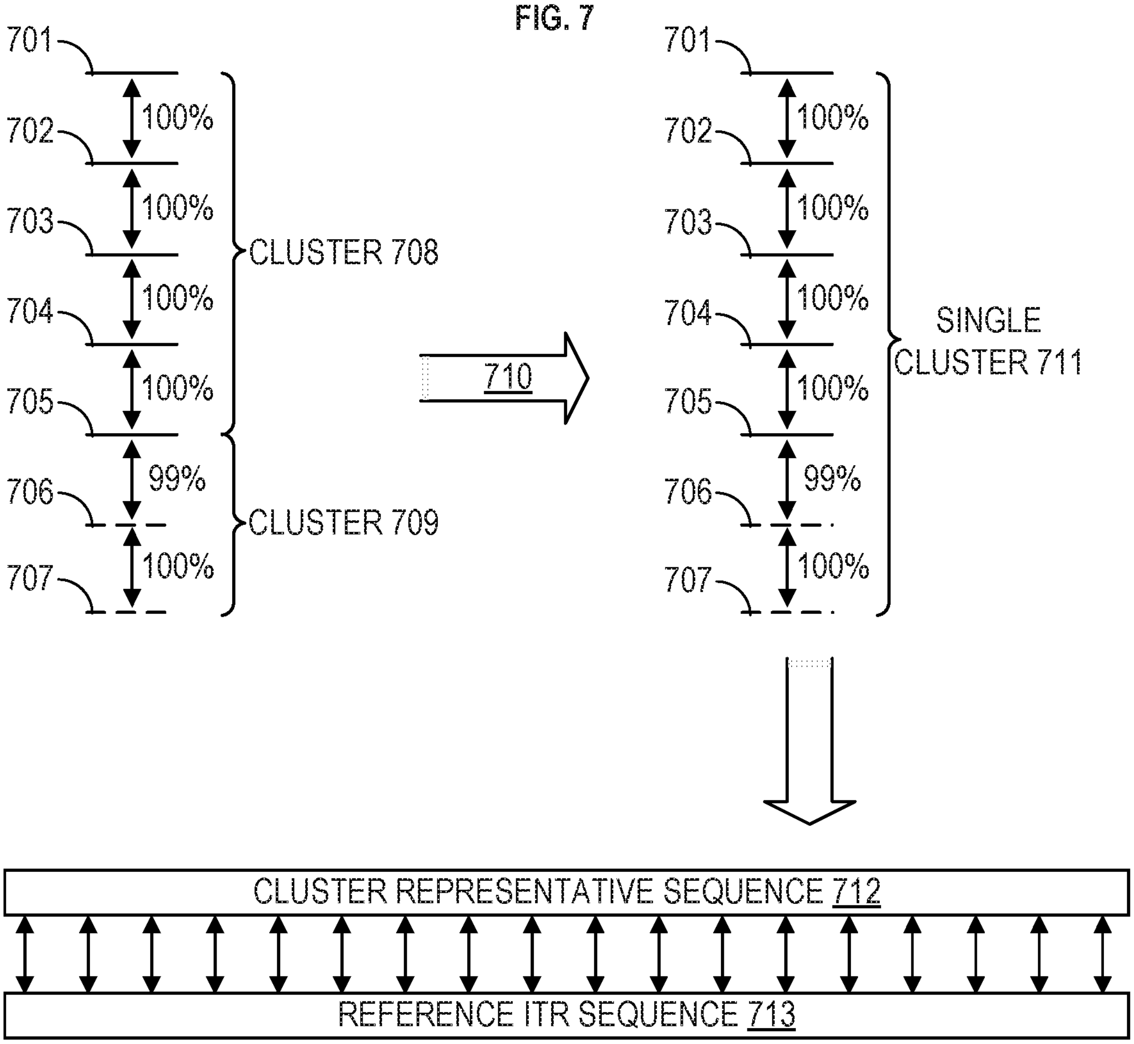
FIG. 7 shows an example method of clustering and merging clusters of sequence regions for comparison of a candidate sequence region to a reference sequence.

As shown in FIG. 7, each of the sequence regions 701, 702, 703, 704, and 705, have been determined to have 100% sequence identity to one another, thus forming a cluster 708 and each of the sequence regions 706 and 707 have been determined to have 100% sequence identity to one another, thus forming a cluster 709. Sequence regions 701, 702, 703, 704, and 705 are not clustered with sequence regions 706 and 707 as the two clusters do not have 100% sequence identity between them. As there are two clusters, the threshold is satisfied and a merge operation is performed to relax the sequence identity requirement to 99% at 710, resulting in each of the sequence regions 701, 702, 703, 704, 705, 706 and 707 having at least 99% sequence identity to one another, thus forming a single cluster 711. As there is only the single cluster 711, a representative ITR sequence 712 from the single cluster 711 may be compared (e.g., aligned, mapped, etc.) against a reference ITR sequence 713. The reference ITR sequence 713 may be, for example, a wild type ITR sequence, an engineered ITR sequence, or any other biologically functional ITR sequence. If the representative ITR sequence 712 matches the reference ITR sequence 713, then the plasmids may be genotyped as the reference ITR sequence 713.

In some aspects, a representative sequence region from each cluster can be aligned with a representative sequence region from each of the other clusters. In some aspects, a representative sequence region for any given cluster, and particularly for clusters generated based on less than 100% sequence identity, can be generally selected by any suitable approach such as, for example, ordering sequence regions within a cluster based on number and/or position of variants, and selecting the middle sequence region in the order as a representative sequence region.

In some aspects, if there is only a single variant between the two aligned clusters, the two clusters can be merged, or combined, into a single cluster. In some aspects, the single variant can be a single deletion, addition, or substitution. In some aspects, 1, 2, 3, 4, 5, 6, 7, 8, 9, or 10 variants can be present in the sequence region and the clusters can be merged. In some aspects, less than 5, 4, 3, or 2 variants can be present in the sequence region and the clusters can be merged. In some aspects, as long as there is at least 99% identity in the aligned sequence regions, then the clusters can be merged.

In some aspects, merging may be performed iteratively by the processor 1808. A first merge operation may be performed, thereby reducing three or more groups into two or more groups. A second merge operation may be performed, thereby reducing the two or more groups into one group. Any number of groups may be merged in a merge operation. Sequence identity constraints may vary per merge operation. For example, a first merge operation may be performed on an initial set of clusters requiring 99-100% identity (e.g., 99.8%), a second merge operation may be performed on remaining clusters requiring 99-100% identity (e.g., 99.5%) between the remaining clusters, a third operation may be performed on remaining clusters requiring 99-100% identity (e.g., 99%), and so on. The amount of variation in identity may vary between merge operations, for example, identity may be varied by 0.1%, 0.2%, 0.3%, 0.4%, 0.5%, 0.6%, 0.7%, 0.8%, 0.9%, 1%, 1.1%, and the like, between merge operations. Any number of merge operations may be performed in order to reduce a number of clusters to any reduced number of clusters.

In some aspects, merging two or more clusters of the plurality of clusters may generate a modified plurality of clusters or a modified cluster. In some aspects, merging two or more clusters of the plurality of clusters may comprise iteratively merging two or more clusters of the plurality of clusters. Each iterative merging of two or more clusters of the plurality of clusters may be based on a different sequence identity. Iteratively merging two or more clusters of the plurality of clusters may be performed until a predetermined number of the plurality of clusters is generated (e.g., 1 cluster). At step 470, the method 400 may perform another cluster analysis based on the merged cluster(s). At step 470, the number of merged clusters may be compared to the threshold. If the number of merged clusters does not satisfy the threshold, then the sequence represented by the merged cluster may be compared to the reference sequence to identify the genotype of the candidate ITR represented by the merged cluster at step 450. For example, the threshold may be 2. Accordingly, in some aspects, if only a single merged cluster is formed (because all of the sequences had perfect identity), the sequence can be compared to the reference sequence and if the sequences are identical (or in some embodiments, substantially identical), the candidate ITR is a match for the reference sequence and thus can be used to produce AAV vectors comprising a viral genome comprising the reference sequence (e.g., a wild type ITR sequence and/or an engineered ITR sequence). In some aspects, the identifying can be based on a local alignment. Thus, in some aspects, the genotype of the candidate ITR sequence is identical (or in some embodiments, substantially identical) to a the reference sequence (e.g., a wild type ITR sequence and/or an engineered ITR sequence). The method 400 may then accept the plasmids. Accepting the plasmids means deeming the plurality of plasmids suitable for production of recombinant vector genomes.

If at step 470, the cluster analysis indicates that the number of merged clusters satisfies the threshold, the method 400 may proceed to step 480 and reject the plurality of plasmids. In some aspects, the method 400 comprises rejecting the plurality of plasmids, after the merging, if two or more clusters remain. In some aspects, rejecting means deeming the plurality of plasmids unsuitable for production of recombinant vector genomes.

In some aspects, a plurality of plasmids from different batches of plasmid can be tested to determine the genotype/identity of the ITRs in the plasmid genome. In the end, each batch can be determined to be accepted or rejected for continued use of producing AAV vectors.

In some aspects, if plasmids have been deemed acceptable per the approaches described herein, the method can further comprise manufacturing recombinant AAV vectors using the plasmids comprising the candidate ITR sequence identical (or in some embodiments, substantially identical) to a reference ITR sequence (e.g., a wild type ITR sequence and/or an engineered ITR sequence).

In some aspects, only those plasmids that are identified as having a genotype of a candidate ITR sequence identical (or in some embodiments, substantially identical) to a reference ITR sequence (e.g., a wild type ITR sequence and/or an engineered ITR sequence) can be used for manufacturing AAV vectors for further use.

In some aspects, if the plasmid has been rejected, the method can further comprise discontinuing manufacturing of AAV vectors produced using the rejected plasmid.

In some aspects, if the plasmid has been accepted, the method can further comprise a step of administering a therapeutically effective amount of an AAV vector, produced from an accepted plasmid, to a subject. Thus, in some aspects, the AAV vector, produced from an accepted plasmid, can comprise a candidate ITR sequence identical (or in some embodiments, substantially identical) to a reference ITR sequence (e.g., a wildtype ITR sequence and/or an engineered ITR sequence).

In some aspects, if the plasmid has been accepted and used to manufacture AAV vectors comprising the candidate ITR sequence identical (or in some embodiments, substantially identical) to a reference ITR sequence (e.g., a wildtype ITR sequence and/or an engineered ITR sequence), then the methods can further comprise packaging the AAV vectors for distribution.

ITRs in AAV Vectors

Aspects of the methods disclosed herein can be performed at least in part by the system 1800 of FIG. 18.

Disclosed are methods comprising sequencing (e.g., by the sequencer 1830 and/or other sequencing apparatus(es) communicably coupled to the computing device 1801 and/or the server 1802) AAV vector genomes, from a plurality of AAV vectors, to obtain a plurality of AAV vector genome sequences; receiving (e.g., by the processor 1808) a specification of a fixed flanking sequence marker; extracting (e.g., by the processor 1808), from each AAV vector genome sequence of the plurality of AAV vectors, based on the presence of the fixed flanking sequence markers in the AAV vector genome sequences, a sequence region immediately to the left or immediately to the right of a flanking sequence marker, wherein the sequence region comprises a candidate ITR sequence; clustering (e.g., by the processor 1808), based on perfect sequence identity, two or more sequence regions of the plurality of sequence regions to generate a plurality of clusters; merging (e.g., by the processor 1808), based on an alignment between their corresponding sequence regions, two or more clusters of the plurality of clusters; and deeming, the plurality of AAV vectors unsuitable for production of recombinant vector genomes, after the merging, if two or more clusters remain.

Disclosed are methods comprising sequencing (e.g., by the sequencer 1830 and/or other sequencing apparatus(es) communicably coupled to the computing device 1801 and/or the server 1802) AAV vector genomes, from a plurality of AAV vectors, to obtain a plurality of AAV vector genome sequences; receiving (e.g., by the processor 1808) a specification of a fixed flanking sequence marker; extracting (e.g., by the processor 1808), from each AAV vector genome sequence of the plurality of AAV vectors, based on the presence of the fixed flanking sequence markers in the AAV vector genome sequences, a sequence region immediately to the left or immediately to the right of a flanking sequence marker, wherein the sequence region comprises a candidate ITR sequence; clustering (e.g., by the processor 1808), based on perfect sequence identity, two or more sequence regions of the plurality of sequence regions to generate a plurality of clusters; merging (e.g., by the processor 1808), based on an alignment between their corresponding sequence regions, two or more clusters of the plurality of clusters; and when a single cluster remains after merging, identifying, based on a local alignment, a genotype of a candidate ITR sequence of the representative sequence.

In some aspects, a plurality of AAV vectors from different batches of AAV vectors can be tested to determine the genotype/identity of the ITRs in the AAV vector genome. In the end, each batch can be determined to be accepted or rejected for continued use.

Disclosed are methods comprising sequencing (e.g., by the sequencer 1830 and/or other sequencing apparatus(es) communicably coupled to the computing device 1801 and/or the server 1802) AAV vector genomes from a plurality of AAV vectors, wherein the plurality of AAV vectors come from two or more batches of AAV vectors, to obtain a plurality of AAV vector genome sequences from each batch of AAV vectors; receiving (e.g., by the processor 1808) a specification of a fixed flanking sequence marker; extracting (e.g., by the processor 1808), from each AAV vector genome sequence of the plurality of AAV vectors, based on the presence of the fixed flanking sequence markers in the AAV vector genome sequences, a sequence region immediately to the left or immediately to the right of a flanking sequence marker, wherein the sequence region comprises a candidate ITR sequence; clustering (e.g., by the processor 1808), based on perfect sequence identity, the two or more sequence regions of the plurality of sequence regions to generate a plurality of clusters; merging (e.g., by the processor 1808), based on an alignment between their corresponding sequence regions, two or more clusters of the plurality of clusters; wherein if two or more clusters remain after merging for at least one batch of AAV vectors, rejecting that batch of AAV vectors for further use, wherein if a single cluster remains for at least one batch of AAV vectors, identifying, based on a local alignment, a genotype of a candidate ITR sequence of the representative sequence, wherein if the candidate ITR is identical (or in some embodiments, substantially identical) to reference ITR sequence (e.g., a wild type AAV ITR sequence and/or an engineered AAV ITR sequence) then accept the use of that batch of AAV vectors.

Figure 8:
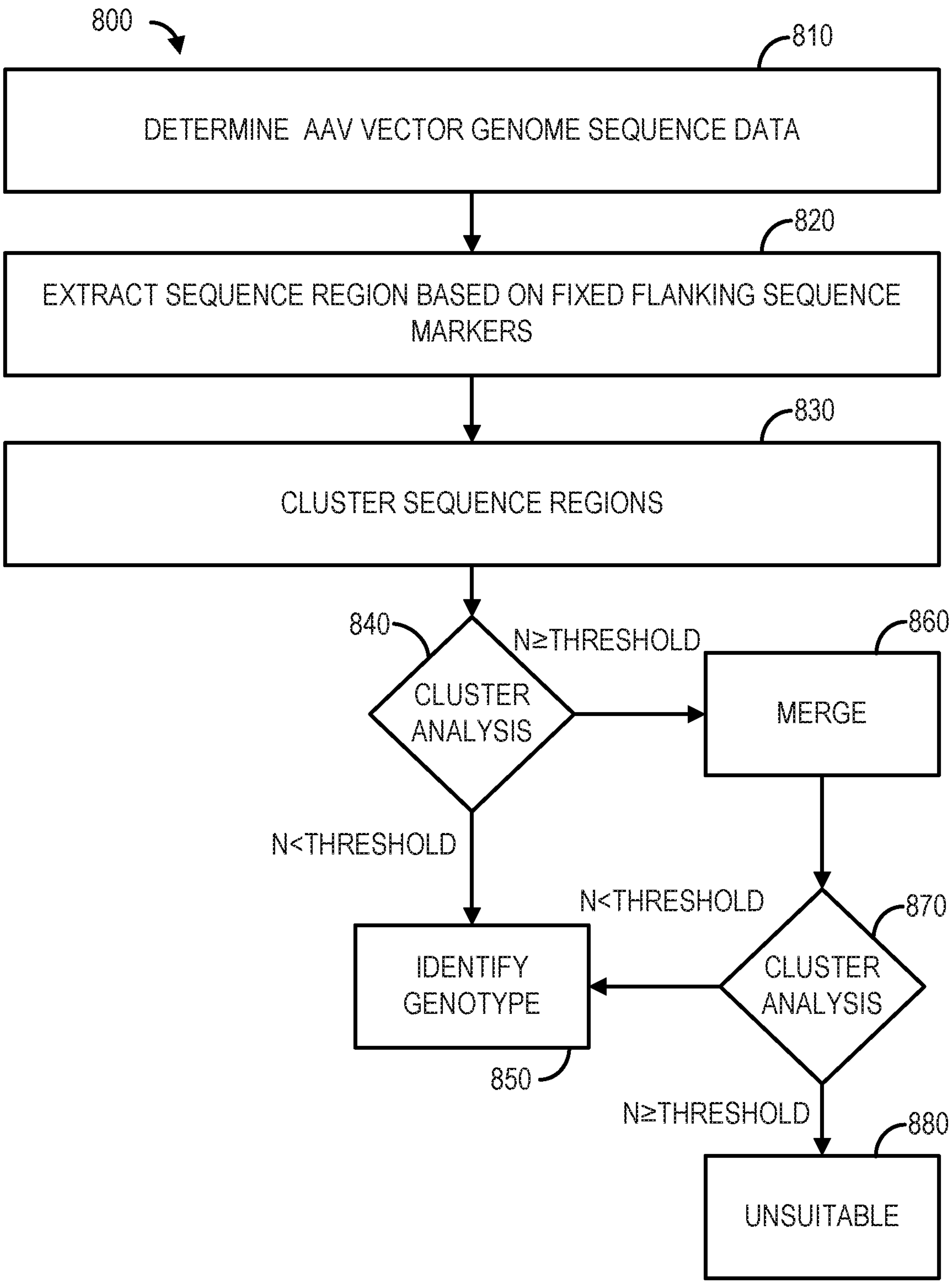
FIG. 8 shows an example method of ITR genotyping.

As shown in FIG. 8, provided are methods, devices (e.g., the device 1801 in FIG. 18), and systems (e.g., the system 1800 in FIG. 18) for identifying genotypes of inverted terminal repeats (ITRs) in AAV vectors.

Disclosed is a method 800 comprising determining, at step 810, AAV vector genome sequence data. The AAV vector genome sequence data may comprise a plurality of AAV vector genome sequences. The plurality of AAV vector genome sequences may be sequences from a plurality of AAV vectors. Determining AAV vector genome sequence data may comprise sequencing (e.g., by the sequencer 1830 and/or other sequencing apparatus(es) communicably coupled to the device 1801 and/or the server 1802) genomes of a plurality of AAV vectors to obtain a plurality of AAV vector genome sequences. Determining AAV vector genome sequence data may comprise receiving the AAV vector genome sequence data.

In some aspects, the sequencing comprises sequencing genomes of a plurality of AAV vectors to obtain a plurality of AAV vector genome sequences. In some aspects, the sequencing comprises sequencing AAV vector genomes, from a plurality of AAV vectors, to obtain a plurality of AAV vector genome sequences.

Disclosed are methods for sequencing plasmid genomes and AAV vector genomes. Plasmid genomes and/or AAV vector genomes can be sequenced and analyzed as a part of the AAV vector production quality control process.

In some aspects, plasmids and/or AAV vectors can first be purified or isolated before sequencing the genomes. In some aspects, AAV capsids can be purified and nucleotides outside the AAV capsids can be eliminated, leaving only nucleotides inside the AAV capsids. The AAV capsids can be denatured to obtain the nucleotides within the AAV capsids. The plasmid genomes or AAV vector genomes can be subjected to one or more DNA sequencing techniques. Sequencing methods executable by the sequencer 1830 can include, for example, long read sequencing and/or circular consensus sequencing (CCS). Other sequencing methods or commercially available formats that are optionally utilized include, for example, Sanger sequencing, high-throughput sequencing, bisulfite sequencing, pyrosequencing, sequencing-by-synthesis, single-molecule sequencing, nanopore-based sequencing, semiconductor sequencing, sequencing-by-ligation, sequencing-by-hybridization, RNA-Seq (Illumina), Digital Gene Expression (Helicos), next generation sequencing (NGS), Single Molecule Sequencing by Synthesis (SMSS) (Helicos), massively-parallel sequencing, Clonal Single Molecule Array (Solexa), shotgun sequencing, Ion Torrent, Oxford Nanopore, Roche Genia, Maxim-Gilbert sequencing, primer walking, sequencing using PacBio, SOLiD, Ion Torrent, or nanopore platforms. Sequencing reactions can be performed in a variety of sample processing units, which may include multiple lanes, multiple channels, multiple wells, or other means of processing multiple sample sets substantially simultaneously. Sample processing units can also include multiple sample chambers to enable the processing of multiple runs simultaneously.

In some aspects, sequencing the plurality of AAV genomes comprises sequencing via long read sequencing. In some aspects, long read sequencing generates sequences 1 kb, 2 kb, 3 kb, 4 kb, 5 kb, 6 kb, 7 kb, 8 kb, 9 kb, 10 kb or greater in length.

In some aspects, the methods can further comprise, after the sequencing step, a step of receiving (e.g., by the processor 1808) a specification of a fixed flanking sequence marker.

The method 800 may comprise extracting one or more sequence regions from the AAV vector genome sequence data at step 820. Extracting one or more sequence regions from the AAV vector genome sequence data may comprise extracting one or more sequence regions from each AAV vector genome sequence of the plurality of AAV vectors in the AAV vector genome sequence data. A sequence region may comprise a candidate ITR sequence. Extracting the one or more sequence regions (or a plurality of sequence regions) from the AAV vector genome sequence data may be based on a fixed flanking sequence marker. Extracting the one or more sequence regions from the p AAV vector genome sequence data may comprise receiving a specification of the fixed flanking sequence marker. Extracting one or more sequence regions from the AAV vector genome sequence data may comprise extracting, from each AAV vector genome sequence, based on the presence of the fixed flanking sequence markers in the AAV vector genome sequence, a sequence region immediately to the left or immediately to the right of a fixed flanking sequence marker, wherein the sequence region comprises a candidate ITR sequence. The extraction may be accomplished by analyzing (e.g., executable by the processor 1808) the positions of the fixed flanking sequence markers in AAV vector genome sequence data and extracting some or all positions from the fixed flanking sequence markers to an end of the AAV vector genome sequence and/or extracting some or all positions in between fixed flanking sequence markers. The result of the extraction may be a sequence region that may be stored as a string or other data structure.

In some aspects, AAV vector genome sequences may comprise fixed flanking sequence markers which are present on only one end of a candidate ITR sequence. In some aspects, fixed flanking sequence markers may comprise sequences of the AAV vector genome that are known and flank one end of a candidate ITR sequence. In some aspects, multiple regions having the fixed flanking sequence marker may be indicative that the sequence region comprising the fixed flanking sequence has a mutation (e.g., concatemerized) and therefore a different fixed flanking sequence marker can be used or that sequence region can be discarded from subsequent analysis.

Figure 5D:
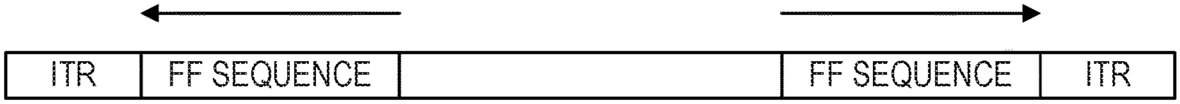

As shown in FIG. 5D, because AAV vector genomes are linear with an ITR at either end of the genome, each sequence region comprising a candidate ITR is flanked with a fixed flanking sequence marker on only one side. Thus, in some aspects, extracting a sequence region (e.g., a candidate ITR sequence) from an AAV vector genome may comprise extracting the sequence region immediately to the left or immediately to the right of a fixed flanking sequence marker.

In some aspects, the AAV vector genomes comprise a sequence having a first ITR, a transgene (or gene of interest), and a second ITR.

In some aspects, because the transgene is known, a portion of the transgene sequence can be specified as a fixed flanking sequence marker. For example, the 5' end of the transgene, which is adjacent to the 3' end of the first ITR, can be used as a fixed flanking sequence marker. Similarly, for the second ITR, the 3' end of the transgene, which is adjacent to the 5' end of the second ITR, can be used as a fixed flanking sequence marker. Thus, there can be a single fixed flanking sequence marker for each ITR. In some aspects, the fixed flanking sequence markers can be known sequences in the transgene.

In some aspects, the fixed flanking sequence markers can be predetermined. For example, the AAV vector genome can be created based on a specific transgene to be present in the AAV vector genome that can be used as a fixed flanking sequence marker. Thus, in some aspects, even before sequencing, the fixed flanking sequence markers that will be used for extracting are known.

In some aspects, because the AAV vector genome is linear, each candidate ITR is flanked on one side by a fixed flanking sequence marker and the sequence from the fixed flanking sequence marker to the end of the AAV vector genome (e.g. end of the ITR) can be extracted.

In some aspects, extracting allows for determining a length of the sequence region. In some aspects, the method comprises discarding the sequence region if the length is above a first threshold or below a second threshold. In some aspects, the first threshold is about 300 base pairs long and the second threshold is zero, about 3 base pairs, about 10 base pairs, about 50 base pairs, about 100 base pairs, about 150 base pairs long or more. In some aspects, the method comprises discarding the sequence region if the length is outside of the range of about 80 bp to about 250 bp. In some aspects, the sequence region can be between 100 bp and 130 bp. For example, in some aspects, the sequence region comprises a candidate ITR which can be about 101 bp (e.g., both hairpin structures of the ITR are deleted), thus, if the length of the sequence region is not at least 101 bp it can be discarded. In some aspects, discarding the sequence region based on length can mean that no further steps after the extracting step need to be performed. In some aspects, if the length is 300 bp or greater then this could be indicative that there are duplicate ITRs present and the sequence region should be discarded. In some aspects, a sequence region having a length outside of the described ranges is further analyzed using the claimed method. In some aspects, the sequence regions having a length outside of the range can provide meaningful information such as, for example, on problems with the manufacturing process. In some aspects, the step of determining the length of the sequence region can be performed immediately after sequencing and before extracting.

Returning to FIG. 8, the one or more extracted sequence regions may be clustered at step 830. Clustering the one or more sequence regions may comprise aligning the sequence regions comprising the candidate ITRs. Clustering may be based on sequence identity. In an aspect, the sequence regions may be clustered based on perfect sequence identity. In some aspects, perfect identity means 99% sequence identity or higher such as, for example, at least 99.5% sequence identity. For example, sequence regions that share 100% sequence identity may be clustered together. One or more clusters may be generated. In some aspects, a single cluster can be formed, wherein all extracted sequence regions are identical. In some aspects, a plurality of clusters can be formed.

If all of the extracted sequence regions have the same identity, then only one cluster (or group) will be formed. However, for as many sequence identities as there are, there will be an equivalent number of clusters. For example, if there are 100 sequence regions extracted and 70 sequence regions have perfect identity, then those 70 extracted sequence regions can be clustered together. If another 20 sequence regions have a different sequence identity to those 70 but are identical to each other, those 20 sequence regions can be clustered together. If the remaining 10 sequence regions have a different sequence identity to the 70 clustered together and to the 20 clustered together, but are identical to each other, those 10 sequence regions can be clustered together. Thus, in this example, there are 3 sequence identities and therefore, 3 clusters (one for each identity).

In some aspects, a cluster can comprise 1, 10, 50, 100, 500, 1000 or more extracted sequence regions. In some aspects, a cluster can comprise a single sequence region. For example, if all of the extracted sequence regions had perfect identity to at least one other sequence region except one extracted sequence region did not match any other sequence regions, that sequence region would form a cluster by itself.

The method 800 may then perform a cluster analysis at step 840. At step 840, the number of clusters may be compared to a threshold. If the number of clusters does not satisfy the threshold, then the sequence represented by the cluster may be compared to a reference sequence to identify the genotype of the candidate ITR at step 850. For example, the threshold may be 2. Accordingly, in some aspects, if only a single cluster is formed (because all of the sequences had perfect identity), the candidate ITR sequence representative of the single cluster can be compared to reference sequence. The reference sequence may be a reference ITR sequence. The reference ITR sequence may be, for example, a wild type ITR sequence, an engineered ITR sequence, or any other biologically functional ITR sequence. If the sequences are identical (or in some embodiments, substantially identical), the candidate ITR is a match for the reference sequence and thus can be used to produce AAV vectors comprising a viral genome comprising the reference sequence (e.g., the wild type ITR sequence and/or the engineered ITR sequence). In some aspects, the identifying can be based on a local alignment, for example a local alignment. An example of clustering and genotyping is shown in FIG. 6 and described previously herein. In some aspects, identifying the genotype of the candidate ITR can be based on an alignment. In some aspects, at step 850, the candidate ITR genotype may be identified by aligning (e.g., mapping) the candidate ITR sequence representing the cluster to the reference sequence using one or more sequence alignment methods. The method 800 may leverage a variety of sequence alignment methods. Examples of such methods include BLAST, which quickly locates regions of local similarity, and Clustal, which is beneficial for simultaneous multiple sequence alignments. The Smith-Waterman algorithm offers high precision for short sequences through rigorous local alignment, while the Needleman-Wunsch algorithm is suitable for global sequence alignment and can pinpoint regions of perfect sequence identity for clustering. Additionally, the MUSCLE (Multiple Sequence Comparison by Log-Expectation) algorithm may be employed, known for its speed and effectiveness in handling large datasets, making it particularly useful for high-throughput sequencing data.

Thus, in some aspects, the genotype of the candidate ITR sequence is identical (or in some embodiments, substantially identical) to the reference sequence (e.g., the wild type ITR sequence and/or the engineered ITR sequence). The method 800 may then accept the AAV vectors. Accepting the AAV vectors means deeming the plurality of AAV vectors suitable for production, distribution, and/or administration.

If at step 840, the cluster analysis indicates that the number of clusters satisfies a threshold, the method 800 may proceed to a merging step 860. The number of clusters may satisfy the threshold by, for example, equaling or exceeding the threshold.

The method 800 may merge two or more clusters at step 860. In some aspects, merging two or more clusters can be based on sequence alignment. In some aspects, the two or more clusters have at least a single variant between their sequences. In some aspects, the methods comprise merging, based on an alignment between their corresponding sequence regions, two or more clusters of the plurality of clusters. In some aspects, the methods comprise merging, based on an alignment between their corresponding sequence regions, two or more clusters of the plurality of clusters to generate a modified plurality of clusters or a modified cluster.

An example of clustering, merging, and genotyping is shown in FIG. 7 and described previously herein. In some aspects, a representative sequence region from each cluster can be aligned with a representative sequence region from each of the other clusters. In some aspects, a representative sequence region for any given cluster, and particularly for clusters generated based on less than 100% sequence identity, can be generally selected by any suitable approach such as, for example, ordering sequence regions within a cluster based on number and/or position of variants, and selecting the middle sequence region in the order as a representative sequence region.

In some aspects, if there is only a single variant between the two aligned clusters, the two clusters can be merged, or combined, into a single cluster. In some aspects, the single variant can be a single deletion, addition, or substitution. In some aspects, 1, 2, 3, 4, 5, 6, 7, 8, 9, or 10 variants can be present in the sequence region and the clusters can be merged. In some aspects, less than 5, 4, 3, or 2 variants can be present in the sequence region and the clusters can be merged. In some aspects, as long as there is at least 99% identity in the aligned sequence regions, then the clusters can be merged.

In some aspects, merging may be performed iteratively by the processor 1808. A first merge operation may be performed, thereby reducing three or more groups into two or more groups. A second merge operation may be performed, thereby reducing the two or more groups into one group. Any number of groups may be merged in a merge operation. Sequence identity constraints may vary per merge operation. For example, a first merge operation may be performed on an initial set of clusters requiring 99-100% identity (e.g., 99.8%), a second merge operation may be performed on remaining clusters requiring 99-100% identity (e.g., 99.5%) between the remaining clusters, a third operation may be performed on remaining clusters requiring 99-100% identity (e.g., 99%), and so on. The amount of variation in identity may vary between merge operations, for example, identity may be varied by 0.1%, 0.2%, 0.3%, 0.4%, 0.5%, 0.6%, 0.7%, 0.8%, 0.9%, 1%, 1.1%, and the like, between merge operations. Any number of merge operations may be performed in order to reduce a number of clusters to any reduced number of clusters.

In some aspects, merging two or more clusters of the plurality of clusters may generate a modified plurality of clusters or a modified cluster. n some aspects, merging two or more clusters of the plurality of clusters may comprise iteratively merging two or more clusters of the plurality of clusters. Each iterative merging of two or more clusters of the plurality of clusters may be based on a different sequence identity. Iteratively merging two or more clusters of the plurality of clusters may be performed until a predetermined number of the plurality of clusters is generated (e.g., 1 cluster).

At step 870, the method 800 may perform another cluster analysis based on the merged clusters. At step 870, the number of merged clusters may be compared to the threshold. If the number of merged clusters does not satisfy the threshold, then the sequence represented by the merged cluster may be compared to the reference sequence to identify the genotype of the candidate ITR represented by the merged cluster at step 850. For example, the threshold may be 2. Accordingly, in some aspects, if only a single merged cluster is formed (because all of the sequences had perfect identity), the sequence can be compared to the reference sequence and if the sequences are identical (or in some embodiments, substantially identical), the candidate ITR is a match for the reference sequence and thus can be used to produce AAV vectors comprising a viral genome comprising the reference sequence (e.g., the wild type ITR sequence and/or the engineered ITR sequence). In some aspects, the identifying can be based on a local alignment. Thus, in some aspects, the genotype of the candidate ITR sequence is identical (or in some embodiments, substantially identical) to the reference sequence (e.g., the wild type ITR sequence and/or the engineered ITR sequence). The method 800 may then accept the AAV vectors. Accepting the AAV vectors means deeming the plurality of AAV vectors suitable for production, distribution, and/or administration.

If at step 870, the cluster analysis indicates that the number of merged clusters satisfies the threshold, the method 800 may proceed to step 880 and reject the plurality of AAV vectors. In some aspects, the method 800 comprises rejecting the plurality of AAV vectors, after the merging, if two or more clusters remain. In some aspects, rejecting means deeming the plurality of AAV vectors unsuitable for production, distribution, and/or administration.

In some aspects, a plurality of AAV vectors from different batches of AAV vectors can be tested to determine the genotype/identity of the ITRs in the AAV vector genomes. In the end, each batch can be determined to be accepted or rejected for continued use for production, distribution, and/or administration.

In some aspects, if AAV vectors have been deemed acceptable per the approaches described herein, the method can further comprise continued manufacturing of the recombinant AAV vectors using the same plasmids comprising the candidate ITR sequence identical (or in some embodiments, substantially identical) to a reference ITR sequence (e.g., a wild type AAV ITR sequence and/or an engineered AAV ITR sequence).

In some aspects, only those plasmids associated with the AAV vectors that are identified as having a genotype of a candidate ITR sequence identical (or in some embodiments, substantially identical) to a reference ITR sequence (e.g., a wild type AAV ITR sequence and/or an engineered AAV ITR sequence) can be used for manufacturing AAV vectors for further use.

In some aspects, if the AAV vector has been rejected, the method can further comprise discontinuing manufacturing of said AAV vectors produced with the plasmid(s) used to produce the rejected AAV vectors.

In some aspects, if the AAV vector has been accepted, the method can further comprise a step of administering a therapeutically effective amount of the AAV vector to a subject. Thus, in some aspects, the AAV vector can comprise a candidate ITR sequence identical (or in some embodiments, substantially identical) to a reference ITR sequence (e.g., a wild type AAV ITR sequence and/or an engineered AAV ITR sequence).

In some aspects, if the AAV vectors have been accepted, then the methods can further comprise packaging the AAV vectors for distribution.

In some aspects, the methods described herein can be used to generate a database of ITR genotypes. For example, in some aspects, the methods can further comprise generating, based on sequence regions associated with clusters comprising two or more sequence regions, a database of ITR genotypes. Thus, in some aspects, each cluster generated that has two or more sequence regions in the cluster, can be placed into a database of known sequence regions (e.g., ITR genotypes).

In some aspects, an ITR that matches a known ITR in the database can provide information on errors during production. For example, in some aspects, ITRs in the database can be associated with production at the wrong temperature or a buffer that may have the wrong pH.

E. Methods of Treating

Disclosed are methods of treating a subject with an AAV vector confirmed to have ITR sequences identical (or in some embodiments, substantially identical) to a reference ITR sequence (e.g., a wild type AAV ITR sequence and/or an engineered AAV ITR sequence) by the method(s) outlined herein.

Disclosed are methods of treating a subject in need thereof comprising administering to the subject a therapeutically effective amount of an AAV vector, wherein the AAV vector genome comprises at least two AAV ITRs, a nucleic acid sequence encoding a therapeutic, and a polyadenylation signal sequence, wherein a genotype of the at least two AAV ITRs are identical (or in some embodiments, substantially identical) to a reference ITR (e.g., a wild type AAV ITR and/or an engineered AAV ITR) determined based on one or more of the methods disclosed herein.

In some aspects, the AAV vector genome can be encapsulated by an AAV capsid.

In some aspects, the subject in need thereof can have any known disease or disorder treated using gene therapy. Thus, in some aspects, the therapeutic can be any gene known to treat the disease or disorder the subject has.

In some aspects, administering a therapeutically effective amount of an AAV vector to a subject results in cells within the subject being transduced by the AAV vector and expression of the therapeutic in the cells.

Methods and uses of the invention include treatment methods, which result in any therapeutic or beneficial effect. In various invention methods and uses, further included are inhibiting, decreasing or reducing one or more adverse (e.g., physical) symptoms, disorders, illnesses, diseases or complications caused by or associated with the disease.

A therapeutic or beneficial effect of treatment is therefore any objective or subjective measurable or detectable improvement or benefit provided to a particular subject. A therapeutic or beneficial effect can but need not be complete ablation of all or any particular adverse symptom, disorder, illness, or complication of a disease. Thus, a satisfactory clinical endpoint is achieved when there is an incremental improvement or a partial reduction in an adverse symptom, disorder, illness, or complication caused by or associated with a disease, or an inhibition, decrease, reduction, suppression, prevention, limit or control of worsening or progression of one or more adverse symptoms, disorders, illnesses, or complications caused by or associated with the disease, over a short or long duration (hours, days, weeks, months, etc.).

Compositions, such as nucleic acids, vectors, recombinant vectors (e.g., rAAV), vector genomes, and recombinant virus particles including vector genomes, and methods and uses of the invention, can be administered in a sufficient or effective amount to a subject in need thereof. An "effective amount" or "sufficient amount" refers to an amount that provides, in single or multiple doses, alone or in combination, with one or more other compositions (therapeutic agents such as a drug), treatments, protocols, or therapeutic regimens agents, a detectable response of any duration of time (long or short term), an expected or desired outcome in or a benefit to a subject of any measurable or detectable degree or for any duration of time (e.g., for minutes, hours, days, months, years, or cured).

One skilled in the art can determine whether administration of a single AAV vector dose is sufficient or whether are to administer multiple doses of AAV vector. For example, if protein levels decreases below a pre-determined level (e.g., less than the minimum that provides a therapeutic benefit), one skilled in the art can determine if appropriate to administer additional doses of AAV vector.

The dose to achieve a therapeutic effect, e.g., the dose in vector genomes/per kilogram of body weight (vg/kg), will vary based on several factors including, but not limited to: route of administration, the level of heterologous polynucleotide expression required to achieve a therapeutic effect, the specific disease treated, any host immune response to the viral vector, a host immune response to the heterologous polynucleotide or expression product (protein), and the stability of the protein expressed. One skilled in the art can determine a AAV vector genome dose range to treat a patient having a particular disease or disorder based on the aforementioned factors, as well as other factors. Generally, doses will range from at least $1\times10^{8}$, or more, for example, $1\times10^{9}$, $1\times10^{10}$, $1\times10^{11}$, $1\times10^{12}$, $1\times10^{13}$ or $1\times10^{14}$, or more, vector genomes per kilogram (vg/kg) of the weight of the subject, to achieve a therapeutic effect.

In certain embodiments, a therapeutically effective dose of an AAV vector is one that is sufficient, when administered to a subject, to achieve therapeutic activity that is about 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, or 50%, or more of normal therapeutic activity. In other embodiments, a therapeutically effective dose is one that achieves 1% or greater therapeutic activity in a subject otherwise lacking such activity, for example, from 1.5-10%, 10-15%, 15-20%, 20-25%, 25-30% or greater therapeutic activity in a subject.

in some aspects, a therapeutically effective dose of an AAV vector may be at least $1\times10^{10}$ vector genomes (vg) per kilogram (vg/kg) of the weight of the subject, or between about $1\times10^{10}$ to $1\times10^{11}$ vg/kg of the weight of the subject, or between about $1\times10^{11}$ to $1\times10^{12}$ vg/kg (e.g., about $1\times10^{11}$ to $2\times10^{11}$ vg/kg or about $2\times10^{11}$ to $3\times10^{11}$ vg/kg or about $3\times10^{11}$ to $4\times10^{11}$ vg/kg or about $4\times10^{11}$ to $5\times10^{11}$ vg/kg or about $5\times10^{11}$ to $6\times10^{11}$ vg/kg or about $6\times10^{11}$ to $7\times10^{11}$ vg/kg or about $7\times10^{11}$ to $8\times10^{11}$ vg/kg or about $8\times10^{11}$ to $9\times10^{11}$ vg/kg or about $9\times10^{11}$ to $1\times10^{12}$ vg/kg) of the weight of the subject, or between about $1\times10^{12}$ to $1\times10^{13}$ vg/kg of the weight of the subject, to achieve a desired therapeutic effect. Additional doses can be in a range of about $5\times10^{10}$ to $1\times10^{10}$ vector genomes (vg) per kilogram (vg/kg) of the weight of the subject, or in a range of about $1\times10^{10}$ to $5\times10^{11}$ vg/kg of the weight of the subject, or in a range of about $5\times10^{11}$ to $1\times10^{12}$ vg/kg of the weight of the subject, or in a range of about $1\times10^{12}$ to $5\times10^{13}$ vg/kg of the weight of the subject, to achieve a desired therapeutic effect. In other embodiments, a therapeutically effective dose of an AAV vector is about $2.0\times10^{11}$ vg/kg, $2.1\times10^{11}$ vg/kg, $2.2\times10^{11}$ vg/kg, $2.3\times10^{11}$ vg/kg, $2.4\times10^{11}$ vg/kg, $2.5\times10^{11}$ vg/kg, $2.6\times10^{11}$ vg/kg, $2.7\times10^{11}$ vg/kg, $2.8\times10^{11}$ vg/kg, $2.9\times10^{11}$ vg/kg, $3.0\times10^{11}$ vg/kg, $3.1\times10^{11}$ vg/kg, $3.2\times10^{11}$ vg/kg, $3.3\times10^{11}$ vg/kg, $3.4\times10^{11}$ vg/kg, $3.5\times10^{11}$ vg/kg, $3.6\times10^{11}$ vg/kg, $3.7\times10^{11}$ vg/kg, $3.8\times10^{11}$ vg/kg, $3.9\times10^{11}$ vg/kg, $4.0\times10^{11}$ vg/kg, $4.1\times10^{11}$ vg/kg, $4.2\times10^{11}$ vg/kg, $4.3\times10^{11}$ vg/kg, $4.4\times10^{11}$ vg/kg, $4.5\times10^{11}$ vg/kg, $4.6\times10^{11}$ vg/kg, $4.7\times10^{11}$ vg/kg, $4.8\times10^{11}$ vg/kg, $4.9\times10^{11}$ vg/kg, $5.0\times10^{11}$ vg/kg, $5.1\times10^{11}$ vg/kg, $5.2\times10^{11}$ vg/kg, $5.3\times10^{11}$ vg/kg, $5.4\times10^{11}$ vg/kg, $5.5\times10^{11}$ vg/kg, $5.6\times10^{11}$ vg/kg, $5.7\times10^{11}$ vg/kg, $5.8\times10^{11}$ vg/kg, $5.9\times10^{11}$ vg/kg, $6.0\times10^{11}$ vg/kg, $6.1\times10^{11}$ vg/kg, $6.2\times10^{11}$ vg/kg, $6.3\times10^{11}$ vg/kg, $6.4\times10^{11}$ vg/kg, $6.5\times10^{11}$ vg/kg, $6.6\times10^{11}$ vg/kg, $6.7\times10^{11}$ vg/kg, $6.8\times10^{11}$ vg/kg, $6.9\times10^{11}$ vg/kg, $7.0\times10^{11}$ vg/kg, $7.1\times10^{11}$ vg/kg, $7.2\times10^{11}$ vg/kg, $7.3\times10^{11}$ vg/kg, $7.4\times10^{11}$ vg/kg, $7.5\times10^{11}$ vg/kg, $7.6\times10^{11}$ vg/kg, $7.7\times10^{11}$ vg/kg, $7.8\times10^{11}$ vg/kg, $7.9\times10^{11}$ vg/kg, or $8.0\times10^{11}$ vg/kg, or some other dose.

The doses of an "effective amount" or "sufficient amount" for treatment (e.g., to ameliorate or to provide a therapeutic benefit or improvement) typically are effective to provide a response to one, multiple or all adverse symptoms, consequences or complications of the disease, one or more adverse symptoms, disorders, illnesses, pathologies, or complications, for example, caused by or associated with the disease, to a measurable extent, although decreasing, reducing, inhibiting, suppressing, limiting or controlling progression or worsening of the disease is a satisfactory outcome.

An effective amount or a sufficient amount can but need not be provided in a single administration, may require multiple administrations, and, can but need not be, administered alone or in combination with another composition (e.g., agent), treatment, protocol or therapeutic regimen. For example, the amount may be proportionally increased as indicated by the need of the subject, type, status and severity of the disease treated or side effects (if any) of treatment. In addition, an effective amount or a sufficient amount need not be effective or sufficient if given in single or multiple doses without a second composition (e.g., another drug or agent), treatment, protocol or therapeutic regimen, since additional doses, amounts or duration above and beyond such doses, or additional compositions (e.g., drugs or agents), treatments, protocols or therapeutic regimens may be included in order to be considered effective or sufficient in a given subject. Amounts considered effective also include amounts that result in a reduction of the use of another treatment, therapeutic regimen or protocol.

An effective amount or a sufficient amount need not be effective in each and every subject treated, nor a majority of treated subjects in a given group or population. An effective amount or a sufficient amount means effectiveness or sufficiency in a particular subject, not a group or the general population. As is typical for such methods, some subjects will exhibit a greater response, or less or no response to a given treatment method or use.

The term "ameliorate" means a detectable or measurable improvement in a subject's disease or symptom thereof, or an underlying cellular response. A detectable or measurable improvement includes a subjective or objective decrease, reduction, inhibition, suppression, limit or control in the occurrence, frequency, severity, progression, or duration of the disease, or complication caused by or associated with the disease, or an improvement in a symptom or an underlying cause or a consequence of the disease, or a reversal of the disease.

Thus, a successful treatment outcome can lead to a "therapeutic effect," or "benefit" of decreasing, reducing, inhibiting, suppressing, limiting, controlling or preventing the occurrence, frequency, severity, progression, or duration of a disease, or one or more adverse symptoms or underlying causes or consequences of the disease in a subject. Treatment methods and uses affecting one or more underlying causes of the disease or adverse symptoms are therefore considered to be beneficial. A decrease or reduction in worsening, such as stabilizing the disease, or an adverse symptom thereof, is also a successful treatment outcome.

A therapeutic benefit or improvement therefore need not be complete ablation of the disease, or any one, most or all adverse symptoms, complications, consequences or underlying causes associated with the disease. Thus, a satisfactory endpoint is achieved when there is an incremental improvement in a subject's disease, or a partial decrease, reduction, inhibition, suppression, limit, control or prevention in the occurrence, frequency, severity, progression, or duration, or inhibition or reversal of the disease (e.g., stabilizing one or more symptoms or complications), over a short or long duration of time (hours, days, weeks, months, etc.). Effectiveness of a method or use, such as a treatment that provides a potential therapeutic benefit or improvement of a disease, can be ascertained by various methods, such as measuring changes in body temperature, etc.

According to some embodiments, a therapeutically effective dose of an AAV vector is one that is sufficient, when administered to a human subject with a given indication, to result in therapeutic activity above a certain level for a sustained period of time. In some of these embodiments, an effective dose of an AAV vector results in at least 1% normal therapeutic activity in human subjects with that indication for a sustained period of at least 3 months, 4 months, 5 months, 6 months, 7 months, 8 months, 9 months, 10 months, 11 months, 12 months, 13 months, 14 months, 15 months, 16 months, 17 months, 1.5 years, 2 years, 2.5 years, 3 years, 3.5 years, 4 years, 4.5 years, 5 years, 5.5 years, 6 years, 6.5 years, 7 years, 7.5 years, 8 years, 8.5 years, 9 years, 9.5 years, 10 years, or more. In other embodiments, an effective dose of an AAV vector results in at least 5% normal therapeutic activity for a sustained period of at least 3, 4, 5, 6, 7, 8, 9, 10, 11, 12, 13, 14, 15, 16, or 17 months, or at least 1.5, 2, 2.5, 3, 3.5, 4, 4.5, 5, 5.5, 6, 6.5, 7, 7.5, 8, 8.5, 9, 9.5, 10 years, or more. In other embodiments, an effective dose of an AAV vector results in at least 10% normal therapeutic activity for a sustained period of at least 3, 4, 5, 6, 7, 8, 9, 10, 11, 12, 13, 14, 15, 16, or 17 months, or at least 1.5, 2, 2.5, 3, 3.5, 4, 4.5, 5, 5.5, 6, 6.5, 7, 7.5, 8, 8.5, 9, 9.5, 10 years, or more. In other embodiments, an effective dose of an AAV vector results in at least 15% normal therapeutic activity for a sustained period of at least 3, 4, 5, 6, 7, 8, 9, 10, 11, 12, 13, 14, 15, 16, or 17 months, or at least 1.5, 2, 2.5, 3, 3.5, 4, 4.5, 5, 5.5, 6, 6.5, 7, 7.5, 8, 8.5, 9, 9.5, 10 years, or more. In other embodiments, an effective dose of an AAV vector results in at least 20% normal therapeutic activity for a sustained period of at least 3, 4, 5, 6, 7, 8, 9, 10, 11, 12, 13, 14, 15, 16, or 17 months, or at least 1.5, 2, 2.5, 3, 3.5, 4, 4.5, 5, 5.5, 6, 6.5, 7, 7.5, 8, 8.5, 9, 9.5, 10 years, or more. In other embodiments, an effective dose of an AAV vector results in at least 25% normal therapeutic activity for a sustained period of at least 3, 4, 5, 6, 7, 8, 9, 10, 11, 12, 13, 14, 15, 16, or 17 months, or at least 1.5, 2, 2.5, 3, 3.5, 4, 4.5, 5, 5.5, 6, 6.5, 7, 7.5, 8, 8.5, 9, 9.5, 10 years, or more. In other embodiments, an effective dose of an AAV vector results in at least 30% normal therapeutic activity for a sustained period of at least 3, 4, 5, 6, 7, 8, 9, 10, 11, 12, 13, 14, 15, 16, or 17 months, or at least 1.5, 2, 2.5, 3, 3.5, 4, 4.5, 5, 5.5, 6, 6.5, 7, 7.5, 8, 8.5, 9, 9.5, 10 years, or more. In other embodiments, an effective dose of an AAV vector results in at least 35% normal therapeutic activity for a sustained period of at least 3, 4, 5, 6, 7, 8, 9, 10, 11, 12, 13, 14, 15, 16, or 17 months, or at least 1.5, 2, 2.5, 3, 3.5, 4, 4.5, 5, 5.5, 6, 6.5, 7, 7.5, 8, 8.5, 9, 9.5, 10 years, or more. In other embodiments, an effective dose of an AAV vector results in at least 40% normal therapeutic activity for a sustained period of at least 3, 4, 5, 6, 7, 8, 9, 10, 11, 12, 13, 14, 15, 16, or 17 months, or at least 1.5, 2, 2.5, 3, 3.5, 4, 4.5, 5, 5.5, 6, 6.5, 7, 7.5, 8, 8.5, 9, 9.5, 10 years, or more. In other embodiments, an effective dose of an AAV vector results in at least 45% normal therapeutic activity for a sustained period of at least 3, 4, 5, 6, 7, 8, 9, 10, 11, 12, 13, 14, 15, 16, or 17 months, or at least 1.5, 2, 2.5, 3, 3.5, 4, 4.5, 5, 5.5, 6, 6.5, 7, 7.5, 8, 8.5, 9, 9.5, 10 years, or more.

According to other embodiments, a therapeutically effective dose of an AAV vector is one that is sufficient, when administered to a human subject with a given indication, to result in therapeutic activity that is at least 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, or 45%, of normal for a sustained period of at least 6 months.

It may be seen that in some human subjects that have received a therapeutically effective dose of an AAV vector, that therapeutic activity attributable to the vector declines over an extended period of time (e.g., months or years) to a level that is no longer deemed sufficient. In such circumstances, the subject can be dosed again with the same type of AAV vector as in the initial treatment. In other embodiments, particularly if the subject has developed an immune reaction to the initial vector, the patient may be dosed with an AAV vector designed to express a therapeutic in target cells, but having a capsid of a different or variant serotype that is less immunoreactive compared to the first AAV vector.

According to certain embodiments, a therapeutically effective dose of an AAV vector is one that is sufficient, when administered to a human subject with a given indication, to reduce or even eliminate the subject's need for recombinant gene replacement therapy to maintain adequate hemostasis. Thus, in some embodiments, a therapeutically effective dose of an AAV vector can reduce the frequency with which an average human subject having that indication needs gene replacement therapy to maintain adequate hemostasis by about 5%, 10%, 15%, 20%, 25%, 30%, 35%, 40%, 45%, 50%, 55%, 60%, 65%, 70%, 75%, 80%, 85%, 90%, 95%, or 100%. In related embodiments, a therapeutically effective dose of an AAV vector can reduce the dose of recombinant human gene that an average human subject having that indication needs to maintain adequate hemostasis by about 5%, 10%, 15%, 20%, 25%, 30%, 35%, 40%, 45%, 50%, 55%, 60%, 65%, 70%, 75%, 80%, 85%, 90%, 95%, or 100%. In any of these embodiments, the AAV vector can be administered to a subject in a pharmaceutically acceptable composition.

In other embodiments, a therapeutically effective dose of an AAV vector is one that is sufficient, when administered to a human subject with a given indication, to reduce or even eliminate a symptom associated with that indication. Thus, in some embodiments, a therapeutically effective dose of an AAV vector can reduce the frequency and/or extent of that symptom by about 5%, 10%, 15%, 20%, 25%, 30%, 35%, 40%, 45%, 50%, 55%, 60%, 65%, 70%, 75%, 80%, 85%, 90%, 95%, or 100%, compared to the average untreated human subject with the same indication. In any of these embodiments, the AAV vector can be administered to a subject in a pharmaceutically acceptable composition alone.

In certain embodiments, the immune response can be an innate immune response, a humoral immune response, or a cellular immune response, or even all three types of immune response. In some embodiments, the immune response can be against the capsid, vector genome, and/or the therapeutic protein produced from transduced cells.

According to certain embodiments, a therapeutically effective dose of an AAV vector results in therapeutic activity adequate to maintain hemostasis in a subject with a given indication, while producing no or minimal humoral (i.e., antibody) immune response against the capsid, genome and/or a therapeutic protein produced from transduced cells. The antibody response to a virus, or virus-like particles such as AAV vectors, can be determined by measuring antibody titer in a subject's serum or plasma using techniques familiar to those of skill in the field of immunology. Antibody titer to any component of an AAV vector, such as the capsid proteins, or a gene product encoded by the vector genome and produced in transduced cells, can be measured using such techniques. Antibody titers are typically expressed as a ratio indicating the dilution before which antibody signal is no longer detectable in the particular assay being used to detect the presence of the antibody. Different dilution factors can be used, for example, 2-fold, 5-fold, 10-fold, or some other dilution factor. Any suitable assay for the presence of an antibody can be used, for example and without limitation, ELISA, FACS, or a reporter gene assay, such as described in WO 2015/006743. Use of other assays is also possible according to the knowledge of those skilled in the art. Antibody titers can be measured at different times after initial administration of an AAV vector.

In certain embodiments, a therapeutically effective dose of an AAV vector results in at least 1%, 5%, 10%, 15%, 20%, 25%, 30%, 35%, 40%, or more therapeutic activity in subjects with a given indication, while producing an antibody titer against the capsid, genome and/or a therapeutic protein produced from transduced cells that is not greater than 1:2, 1:3, 1:4, 1:5, 1:6, 1:7, 1:8, 1:9, 1:10, 1:11, 1:12, 1:13, 1:14, 1:15, 1:20, 1:30, 1:40, 1:50, 1:60, 1:70, 1:80, 1:90, 1:100, 1:200, 1:300, 1:400, 1:500, or more, when determined at 1 week, 2 weeks, 3 weeks, 4 weeks, 5 weeks, 6 weeks, 7 weeks, 8 weeks, 3 months, 4 months, 5 months, 6 months, 7 months, 8 months, 9 months, 10 months, 11 months, 12 months, 18 months, 2 years, 3 years, 4 years, 5 years, or a longer period after the subjects were administered the AAV vector. According to one exemplary non-limiting embodiment, an AAV vector results in at least 20% therapeutic activity in a subject with a given indication while inducing an antibody titer against the capsid and/or a therapeutic produced by transduced cells that is not greater than 1:2, 1:3 or 1:4, both at 6 months after the AAV vector was administered. In any of these embodiments, the AAV vector can be administered to a subject in a pharmaceutically acceptable composition alone.

In certain embodiments, a therapeutically effective dose of an AAV vector results in therapeutic activity adequate to maintain hemostasis in a subject with a given indication, while producing no or minimal cellular immune response against the capsid and/or a therapeutic protein produced from transduced cells. A cellular immune response can be determined at least by assaying for T cell activity specific for capsid proteins or therapeutic.

In some embodiments, cellular immune response is determined by assaying for T cell activity specific for capsid proteins and/or the therapeutic protein produced by the transduced cells. Different assays for T cell response are known in the art. In one exemplary, non-limiting embodiment, T cell response is determined by collecting peripheral blood mononuclear cells (PBMC) from a subject that was previously treated with an AAV vector for treating a given indication. The cells are then incubated with peptides derived from the VP1 capsid protein used in the vector, and/or the therapeutic protein produced by the transduced liver cells. T cells that specifically recognize the capsid protein or a therapeutic protein will be stimulated to release cytokines, such as interferon gamma or another cytokine, which can then be detected and quantified using the ELISPOT assay, or another assay familiar to those of skill in the art. (See, e.g., Manno, et al., Nat Med 2006; 12(3):342-347). T cell response can be monitored before and at different times after a subject has received a dose of an AAV vector for treating that indication, for example, weekly, monthly, or some other interval. Thus, according to certain embodiments, a therapeutically effective dose of an AAV vector results in therapeutic activity adequate to maintain hemostasis in a subject with that indication (for example, therapeutic activity of at least 1%, 5%, 10%, 20%, 30%, or more), while causing a T cell response as measured using ELISPOT that is not greater than 10, 20, 30, 40, 50, 100, 200, 300, 400, 500, 600, 700, 800, 900, 1000, 1500, 2000, or more, spot-forming units per 1 million PBMCs assayed when measured weekly, monthly, or some other interval after the AAV vector is administered, or at 2 weeks, 1 month, 2 months, 3 months, 6 months, 9 months, 1 year, 2 years, or some different time after the AAV vector is administered. In some of these embodiments, the ELISPOT assay is designed to detect interferon gamma (or some other cytokine) production stimulated by peptides from the AAV vector capsid protein or a therapeutic protein produced by transduced liver cells. In any of these embodiments, the AAV vector can be administered to a subject in a pharmaceutically acceptable composition alone.

As a proxy for the cellular immune response against transduced cells, the presence of greater-than-normal cellular enzymes can be assayed using standard methods. While not wishing to be bound by theory, it is believed that T cells specific for certain AAV vectors, such as those used in prior clinical trials, can attack and kill transduced cells, which transiently releases enzymes into the circulation. A normal level of these enzymes in the circulation is typically defined as a range that has an upper level, above which the enzyme level is considered elevated, and therefore indicative of liver damage. A normal range depends in part on the standards used by the clinical laboratory conducting the assay. In certain embodiments, a therapeutically effective dose of an AAV vector results in therapeutic activity adequate to maintain hemostasis in a subject with that indication (for example, therapeutic activity of at least 1%, 5%, 10%, 20%, 30%, or more), while causing an elevated circulating enzyme level, such as that of ALT, AST, or LDH, which is not greater than 0%, 10%, 20%, 30%, 40%, 50%, 60%, 70%, 80%, 90%, 100%, 200%, 300%, 400%, 500%, 600%, 700%, 800%, 900%, 1000%, 1500%, 2000% of the upper limit of normal (ULN) value of their respective ranges, on average, or at the highest level measured in multiple samples drawn from the same subject under treatment at different times (e.g., at weekly or monthly intervals) after administration of the AAV vector.

In prior clinical trials using AAV vectors, the investigators needed to co-administer an immunosuppressant drug, such as a steroid, to prevent the subjects receiving treatment from mounting an immune response that would eliminate the transduced cells producing the therapeutic protein. Due to the attenuated immune response seen in subjects undergoing experimental treatment with certain AAV vectors, however, co-administration of immunosuppressing drugs may not be necessary. Thus, in certain embodiments, a therapeutically effective dose of an AAV vector is one that is sufficient to maintain adequate hemostasis in a subject with a given indication, without need for co-administration (before, contemporaneously, or after) of an immunosuppressant drug (such as a steroid or other immunosuppressant). Because an immune response is not predictable in all subjects, however, the methods herein of treatment include AAV vectors that are co-administered with an immunosuppressant drug. Co-administration of an immunosuppressant drug can occur before, contemporaneously with, or after AAV vectors are administered to a subject having that indication. In some embodiments, an immunosuppressant drug is administered to a subject for a period of days, weeks, or months after being administered an AAV vector for treating that indication. Exemplary immunosuppressing drugs include steroids (e.g., without limitation, prednisone or prednisolone) and non-steroidal immunosuppressants, such as cyclosporin, rapamycin, and others. What drug doses and time course of treatment are required to effect sufficient immunosuppression will depend on factors unique to each subject undergoing treatment, but determining dose and treatment time are within the skill of those ordinarily skilled in the art. In some embodiments, an immunosuppressant may need to be administered more than one time.

According to certain embodiments, a therapeutically effective dose of an AAV vector results in a consistent elevation of therapeutic activity when administered to a population of human subjects with a given indication. Consistency can be determined by calculating variability of response in a population of human subjects using statistical methods such the mean and standard deviation (SD), or another statistical technique familiar to those of skill in the art. In some embodiments, a therapeutically effective dose of an AAV vector, when administered to a population of human subjects with that indication results, at 3 months, 6 months, 9 months, 12 months, 15 months, 18 months, 21 months, or 21 months after administration, in a mean therapeutic activity of 1-5% with a SD of less than 15, 14, 13, 12, 11, 10, 9, 8, 7, 6, 5, 4, 3, 2, or 1; a mean therapeutic activity of 2.5-7.5% with a SD of less than 15, 14, 13, 12, 11, 10, 9, 8, 7, 6, 5, 4, 3, 2, or 1; a mean therapeutic activity of 5-10% with a SD of less than 15, 14, 13, 12, 11, 10, 9, 8, 7, 6, 5, 4, 3, 2, or 1; a mean therapeutic activity of 7.5-12.5% with a SD of less than 15, 14, 13, 12, 11, 10, 9, 8, 7, 6, 5, 4, 3, 2, or 1; a mean therapeutic activity of 10-15% with a SD of less than 15, 14, 13, 12, 11, 10, 9, 8, 7, 6, 5, 4, 3, 2, or 1; a mean therapeutic activity of 12.5-17.5% with a SD of less than 15, 14, 13, 12, 11, 10, 9, 8, 7, 6, 5, 4, 3, 2, or 1; a mean therapeutic activity of 15-20% with a SD of less than 15, 14, 13, 12, 11, 10, 9, 8, 7, 6, 5, 4, 3, 2, or 1; a mean therapeutic activity of 17.5-22.5% with a SD of less than 15, 14, 13, 12, 11, 10, 9, 8, 7, 6, 5, 4, 3, 2, or 1; a mean therapeutic activity of 20-25% with a SD of less than 15, 14, 13, 12, 11, 10, 9, 8, 7, 6, 5, 4, 3, 2, or 1; a mean therapeutic activity of 22.5-27.5% with a SD of less than 15, 14, 13, 12, 11, 10, 9, 8, 7, 6, 5, 4, 3, 2, or 1; a mean therapeutic activity of 25-30% with a SD of less than 15, 14, 13, 12, 11, 10, 9, 8, 7, 6, 5, 4, 3, 2, or 1; a mean therapeutic activity of 27.5-32.5% with a SD of less than 15, 14, 13, 12, 11, 10, 9, 8, 7, 6, 5, 4, 3, 2, or 1; a mean therapeutic activity of 30-35% with a SD of less than 15, 14, 13, 12, 11, 10, 9, 8, 7, 6, 5, 4, 3, 2, or 1; a mean therapeutic activity of 32.5-37.5% with a SD of less than 15, 14, 13, 12, 11, 10, 9, 8, 7, 6, 5, 4, 3, 2, or 1; a mean therapeutic activity of 35-40% with a SD of less than 15, 14, 13, 12, 11, 10, 9, 8, 7, 6, 5, 4, 3, 2, or 1; a mean therapeutic activity of 37.5-42.5% with a SD of less than 15, 14, 13, 12, 11, 10, 9, 8, 7, 6, 5, 4, 3, 2, or 1; a mean therapeutic activity of 40-45% with a SD of less than 15, 14, 13, 12, 11, 10, 9, 8, 7, 6, 5, 4, 3, 2, or 1; a mean therapeutic activity of 42.5-47.5% with a SD of less than 15, 14, 13, 12, 11, 10, 9, 8, 7, 6, 5, 4, 3, 2, or 1; or a mean therapeutic activity of 45-50% with a SD of less than 15, 14, 13, 12, 11, 10, 9, 8, 7, 6, 5, 4, 3, 2, or 1. In any of these embodiments, the AAV vector can be administered to a subject in a pharmaceutically acceptable composition alone.

Invention methods and uses can be combined with any compound, agent, drug, treatment or other therapeutic regimen or protocol having a desired therapeutic, beneficial, additive, synergistic or complementary activity or effect. Exemplary combination compositions and treatments include second actives, such as, biologics (proteins), agents and drugs. Such biologics (proteins), agents, drugs, treatments and therapies can be administered or performed prior to, substantially contemporaneously with or following any other method or use of the invention.

The compound, agent, drug, treatment or other therapeutic regimen or protocol can be administered as a combination composition, or administered separately, such as concurrently or in series or sequentially (prior to or following) delivery or administration of a nucleic acid, vector, recombinant vector (e.g., rAAV), vector genome, or recombinant virus particle. The invention therefore provides combinations in which a method or use of the invention is in a combination with any compound, agent, drug, therapeutic regimen, treatment protocol, process, remedy or composition, set forth herein or known to one of skill in the art. The compound, agent, drug, therapeutic regimen, treatment protocol, process, remedy or composition can be administered or performed prior to, substantially contemporaneously with or following administration of a nucleic acid, vector, recombinant vector (e.g., rAAV), vector genome, or recombinant virus particle of the invention, to a subject.

In certain embodiments, a combination composition includes one or more immunosuppressive agents. In certain embodiments a method includes administering or delivering one or more immunosuppressive agents to the mammal. In certain embodiments, a combination composition includes AAV-therapeutic particles and one or more immunosuppressive agents. In certain embodiments, a method includes administering or delivering AAV-therapeutic particles to a mammal and administering an immunosuppressive agent to the mammal. The skilled artisan can determine appropriate need or timing of such a combination composition with one or more immunosuppressive agents and administering the immunosuppressive agent to the mammal.

Methods and uses of the invention also include, among other things, methods and uses that result in a reduced need or use of another compound, agent, drug, therapeutic regimen, treatment protocol, process, or remedy. Thus, in accordance with the invention, methods and uses of reducing need or use of another treatment or therapy are provided.

The invention is useful in animals including human and veterinary medical applications. Suitable subjects therefore include mammals, such as humans, as well as non-human mammals. The term "subject" refers to an animal, typically a mammal, such as humans, non-human primates (apes, gibbons, gorillas, chimpanzees, orangutans, macaques), a domestic animal (dogs and cats), a farm animal (poultry such as chickens and ducks, horses, cows, goats, sheep, pigs), and experimental animals (mouse, rat, rabbit, guinea pig). Human subjects include fetal, neonatal, infant, juvenile and adult subjects. Subjects include animal disease models, for example, mouse and other animal models of blood clotting diseases and others known to those of skill in the art.

Subjects appropriate for treatment include those having or at risk of producing an insufficient amount or having a deficiency in a functional gene product (protein), or produce an aberrant, partially functional or non-functional gene product (protein), which can lead to disease. Subjects appropriate for treatment in accordance with the invention also include those having or at risk of producing an aberrant, or defective (mutant) gene product (protein) that leads to a disease such that reducing amounts, expression or function of the aberrant, or defective (mutant) gene product (protein) would lead to treatment of the disease, or reduce one or more symptoms or ameliorate the disease.

Subjects appropriate for treatment in accordance with the invention further include those previously or currently treated with supplemental protein. Subjects appropriate for treatment in accordance with the invention moreover include those that have not developed a substantial or detectable immune response against the therapeutic protein, or amounts of inhibitory antibodies against the therapeutic protein that would interfere with or block the therapeutic based gene therapy.

In other embodiments, human pediatric subjects that are determined to have a given indication (e.g., by genotyping), but have not yet exhibited any of the symptoms of that indication, can be treated prophylactically with an AAV vector to prevent any such symptoms from occurring in the first place or, in other embodiments, from being as severe as they otherwise would have been in the absence of treatment. In some embodiments, human subjects treated prophylactically in this way are at least 3, 4, 5, 6, 7, 8, 9, 10, 11, 12, 13, 14, 15, 16, 17, 18 months old, or older, when they are administered an AAV vector to produce and maintain therapeutic activity adequate to maintain hemostasis, and thus prevent or reduce the severity of one or more symptoms of that indication. In any of these embodiments, the AAV vector can be administered to a subject in a pharmaceutically acceptable composition alone.

Administration or in vivo delivery to a subject can be performed prior to development of an adverse symptom, condition, complication, etc. caused by or associated with the disease. For example, a screen (e.g., genetic) can be used to identify such subjects as candidates for invention compositions, methods and uses. Such subjects therefore include those screened positive for an insufficient amount or a deficiency in a functional gene product (protein), or that produce an aberrant, partially functional or non-functional gene product (protein).

Methods and uses of the invention include delivery and administration systemically, regionally or locally, or by any route, for example, by injection or infusion. Such delivery and administration include parenterally, e.g. intravascularly, intravenously, intramuscularly, intraperitoneally, intradermally, subcutaneously, or transmucosal. Exemplary administration and delivery routes include intravenous (i.v.), intraperitoneal (i.p.), intrarterial, subcutaneous, intra-pleural, intubation, intrapulmonary, intracavity, iontophoretic, intraorgan, intralymphatic.

Doses can vary and depend upon whether the type, onset, progression, severity, frequency, duration, or probability of the disease to which treatment is directed, the clinical endpoint desired, previous or simultaneous treatments, the general health, age, gender, race or immunological competency of the subject and other factors that will be appreciated by the skilled artisan. The dose amount, number, frequency or duration may be proportionally increased or reduced, as indicated by any adverse side effects, complications or other risk factors of the treatment or therapy and the status of the subject. The skilled artisan will appreciate the factors that may influence the dosage and timing required to provide an amount sufficient for providing a therapeutic or prophylactic benefit.

Methods and uses of the invention as disclosed herein can be practiced within 1-2, 2-4, 4-12, 12-24 or 24-72 hours after a subject has been identified as having the disease targeted for treatment, has one or more symptoms of the disease, or has been screened and is identified as positive as set forth herein even though the subject does not have one or more symptoms of the disease. Of course, methods and uses of the invention can be practiced 1-7, 7-14, 14-21, 21-48 or more days, months or years after a subject has been identified as having the disease targeted for treatment, has one or more symptoms of the disease, or has been screened and is identified as positive as set forth herein.

Invention nucleic acids, vectors, recombinant vectors (e.g., rAAV), vector genomes, and recombinant virus particles and other compositions, agents, drugs, biologics (proteins) can be incorporated into pharmaceutical compositions, e.g., a pharmaceutically acceptable carrier or excipient. Such pharmaceutical compositions are useful for, among other things, administration and delivery to a subject in vivo or ex vivo.

As used herein the term "pharmaceutically acceptable" and "physiologically acceptable" mean a biologically acceptable formulation, gaseous, liquid or solid, or mixture thereof, which is suitable for one or more routes of administration, in vivo delivery or contact. A "pharmaceutically acceptable" or "physiologically acceptable" composition is a material that is not biologically or otherwise undesirable, e.g., the material may be administered to a subject without causing substantial undesirable biological effects. Thus, such a pharmaceutical composition may be used, for example in administering a viral vector or viral particle to a subject.

Such compositions include solvents (aqueous or non-aqueous), solutions (aqueous or non-aqueous), emulsions (e.g., oil-in-water or water-in-oil), suspensions, syrups, elixirs, dispersion and suspension media, coatings, isotonic and absorption promoting or delaying agents, compatible with pharmaceutical administration or in vivo contact or delivery. Aqueous and non-aqueous solvents, solutions and suspensions may include suspending agents and thickening agents. Such pharmaceutically acceptable carriers include tablets (coated or uncoated), capsules (hard or soft), microbeads, powder, granules and crystals. Supplementary active compounds (e.g., preservatives, antibacterial, antiviral and antifungal agents) can also be incorporated into the compositions.

Pharmaceutical compositions can be formulated to be compatible with a particular route of administration or delivery, as set forth herein or known to one of skill in the art. Thus, pharmaceutical compositions include carriers, diluents, or excipients suitable for administration by various routes.

Compositions suitable for parenteral administration comprise aqueous and non-aqueous solutions, suspensions or emulsions of the active compound, which preparations are typically sterile and can be isotonic with the blood of the intended recipient. Non-limiting illustrative examples include water, saline, dextrose, fructose, ethanol, animal, vegetable or synthetic oils.

Cosolvents and adjuvants may be added to the formulation. Non-limiting examples of cosolvents contain hydroxyl groups or other polar groups, for example, alcohols, such as isopropyl alcohol; glycols, such as propylene glycol, polyethyleneglycol, polypropylene glycol, glycol ether; glycerol; polyoxyethylene alcohols and polyoxyethylene fatty acid esters. Adjuvants include, for example, surfactants such as, soya lecithin and oleic acid; sorbitan esters such as sorbitan trioleate; and polyvinylpyrrolidone.

Pharmaceutical compositions and delivery systems appropriate for the compositions, methods and uses of the invention are known in the art (see, e.g., Remington: The Science and Practice of Pharmacy (2003) 20th ed., Mack Publishing Co., Easton, Pa.; Remington's Pharmaceutical Sciences (1990) 18th ed., Mack Publishing Co., Easton, Pa.; The Merck Index (1996) 12th ed., Merck Publishing Group, Whitehouse, N.J.; Pharmaceutical Principles of Solid Dosage Forms (1993), Technonic Publishing Co., Inc., Lancaster, Pa.; Ansel and Stoklosa, Pharmaceutical Calculations (2001) 11th ed., Lippincott Williams & Wilkins, Baltimore, Md.; and Poznansky et al., Drug Delivery Systems (1980), R. L. Juliano, ed., Oxford, N.Y., pp. 253-315).

A "unit dosage form" as used herein refers to physically discrete units suited as unitary dosages for the subject to be treated; each unit containing a predetermined quantity optionally in association with a pharmaceutical carrier (excipient, diluent, vehicle or filling agent) which, when administered in one or more doses, is calculated to produce a desired effect (e.g., prophylactic or therapeutic effect). Unit dosage forms may be within, for example, ampules and vials, which may include a liquid composition, or a composition in a freeze-dried or lyophilized state; a sterile liquid carrier, for example, can be added prior to administration or delivery in vivo. Individual unit dosage forms can be included in multi-dose kits or containers. Recombinant vector (e.g., rAAV) sequences, vector genomes, recombinant virus particles, and pharmaceutical compositions thereof can be packaged in single or multiple unit dosage form for ease of administration and uniformity of dosage.

F. Methods of Manufacturing

Disclosed are methods of manufacturing an AAV vector confirmed to have ITR sequences identical (or in some embodiments, substantially identical) to a reference ITR sequence (e.g., a wild type A AV ITR sequence and/or an engineered AAV ITR sequence).

Disclosed are method of manufacturing comprising sequencing (e.g., by the sequencer 1830 and/or other sequencing apparatus(es) communicably coupled to the computing device 1801 and/or the server 1802) genomes of a plurality of plasmids to obtain a plurality of plasmid genome sequences; receiving (e.g., by the processor 1808) a specification of a fixed flanking sequence marker; extracting (e.g., by the processor 1808), from each plasmid genome sequence, based on the presence of the fixed flanking sequence markers in that plasmid genome sequence, a plurality of sequence regions, wherein each sequence region is within the fixed flanking sequence markers and comprises a candidate inverted terminal repeat (ITR) sequence; clustering (e.g., by the processor 1808), based on perfect sequence identity, two or more sequence regions of the plurality of sequence regions to generate a plurality of clusters; merging (e.g., by the processor 1808), based on an alignment between their corresponding sequence regions, two or more clusters of the plurality of clusters; when a single cluster remains, identifying, based on a local alignment, a genotype of a candidate ITR sequence of the representative sequence region; manufacturing a plurality of AAV vectors using a plurality of the plasmids having the candidate ITR sequence of the representative sequence region (e.g. having an ITR identical or substantially identical to a reference ITR sequence (e.g., a wild type AAV ITR sequence and/or an engineered AAV ITR sequence).

G. Kits

Disclosed are kits for identifying genotypes of ITRs or kits for producing AAV vectors comprising ITRs identical (or in some embodiments, substantially identical) to reference ITRs (e.g., wild type ITRs and/or engineered ITRs).

The invention provides kits with packaging material and one or more components therein. A kit typically includes a label or packaging insert including a description of the components or instructions for use in vitro, in vivo, or ex vivo, of the components therein. A kit can contain a collection of such components, e.g., a nucleic acid, recombinant vector, virus (e.g., AAV) vector, vector genome or virus particle and optionally a second active, such as another compound, agent, drug or composition.

A kit refers to a physical structure housing one or more components of the kit. Packaging material can maintain the components sterilely, and can be made of material commonly used for such purposes (e.g., paper, corrugated fiber, glass, plastic, foil, ampules, vials, tubes, etc.).

Labels or inserts can include identifying information of one or more components therein, dose amounts, clinical pharmacology of the active ingredient(s) including mechanism of action, pharmacokinetics and pharmacodynamics. Labels or inserts can include information identifying manufacturer, lot numbers, manufacture location and date, expiration dates. Labels or inserts can include information identifying manufacturer information, lot numbers, manufacturer location and date. Labels or inserts can include information on a disease for which a kit component may be used. Labels or inserts can include instructions for the clinician or subject for using one or more of the kit components in a method, use, or treatment protocol or therapeutic regimen. Instructions can include dosage amounts, frequency or duration, and instructions for practicing any of the methods, uses, treatment protocols or prophylactic or therapeutic regimes described herein.

Labels or inserts can include information on any benefit that a component may provide, such as a prophylactic or therapeutic benefit. Labels or inserts can include information on potential adverse side effects, complications or reactions, such as warnings to the subject or clinician regarding situations where it would not be appropriate to use a particular composition. Adverse side effects or complications could also occur when the subject has, will be or is currently taking one or more other medications that may be incompatible with the composition, or the subject has, will be or is currently undergoing another treatment protocol or therapeutic regimen which would be incompatible with the composition and, therefore, instructions could include information regarding such incompatibilities.

Labels or inserts include "printed matter," e.g., paper or cardboard, or separate or affixed to a component, a kit or packing material (e.g., a box), or attached to an ampule, tube or vial containing a kit component. Labels or inserts can additionally include a computer readable medium, such as a bar-coded printed label, a disk, optical disk such as CD- or DVD-ROM/RAM, DVD, MP3, magnetic tape, or an electrical storage media such as RAM and ROM or hybrids of these such as magnetic/optical storage media, FLASH media or memory type cards.

The following examples illustrate the present methods and systems. The following Examples are not intended to be limiting thereof.

Example 1

Figure 9:
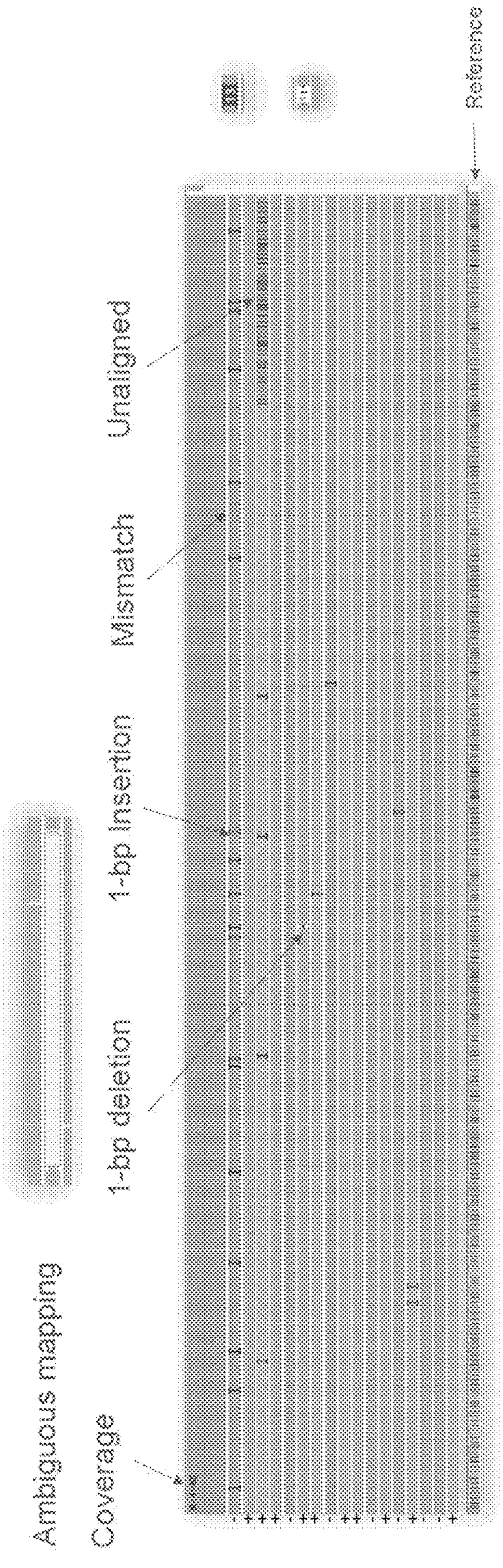
FIG. 9 shows an Integrative Genomics Viewer (IGV).

FIG. 9 shows an Integrative Genomics Viewer (IGV), where each row is a read, + indicates positive strand and − indicates a negative strand. The bottom row indicates a reference sequence.

Figure 10:
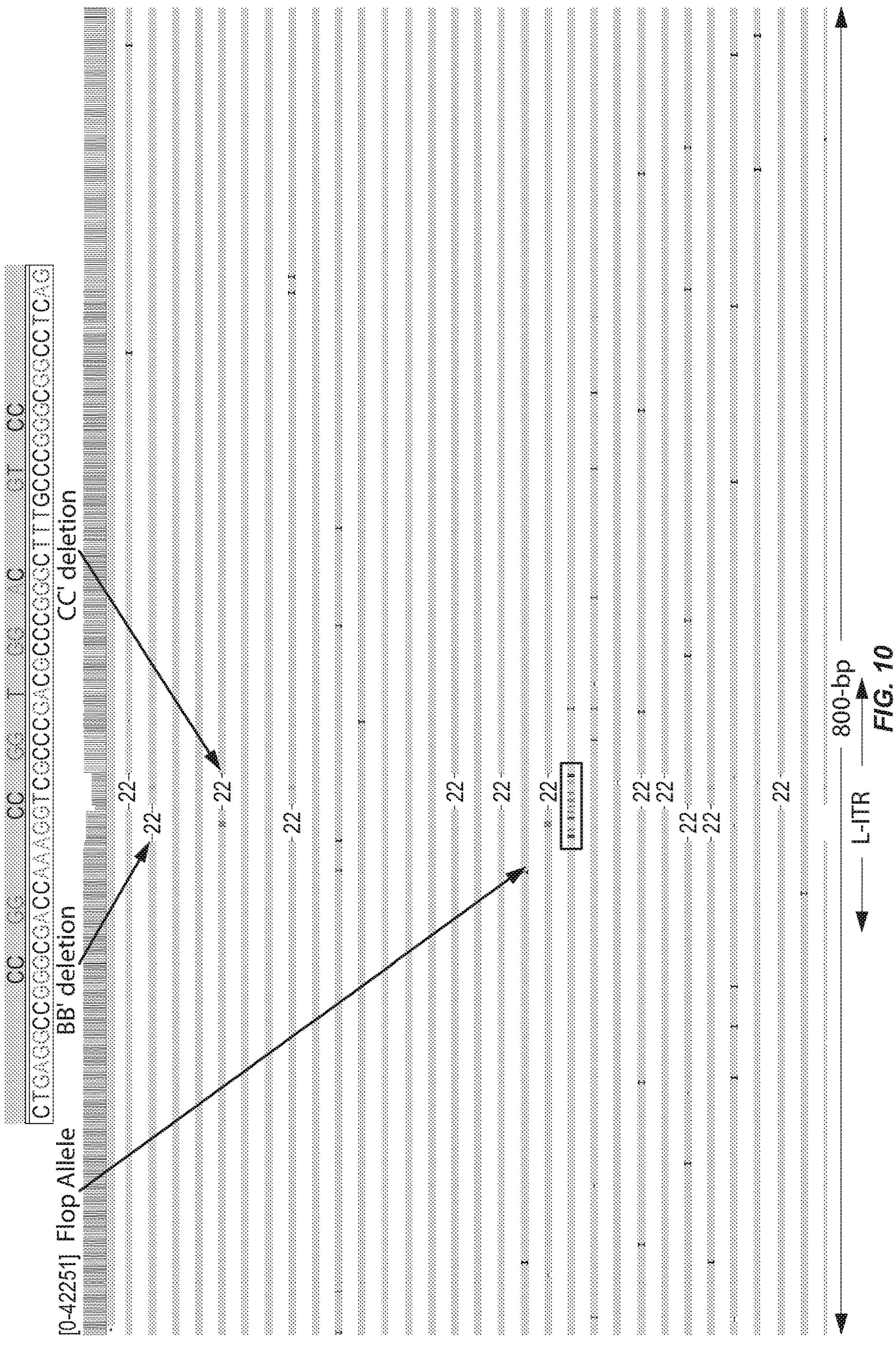
FIG. 10 shows a visualization of pINT alignment to a reference sequence using PacBio CCS (Circular Consensus Sequence) data. Flip (SEQ ID NO:1); Flop (SEQ ID NO:2); and portion of Flop allele is shown in SEQ ID NO:3.
Figure 10:
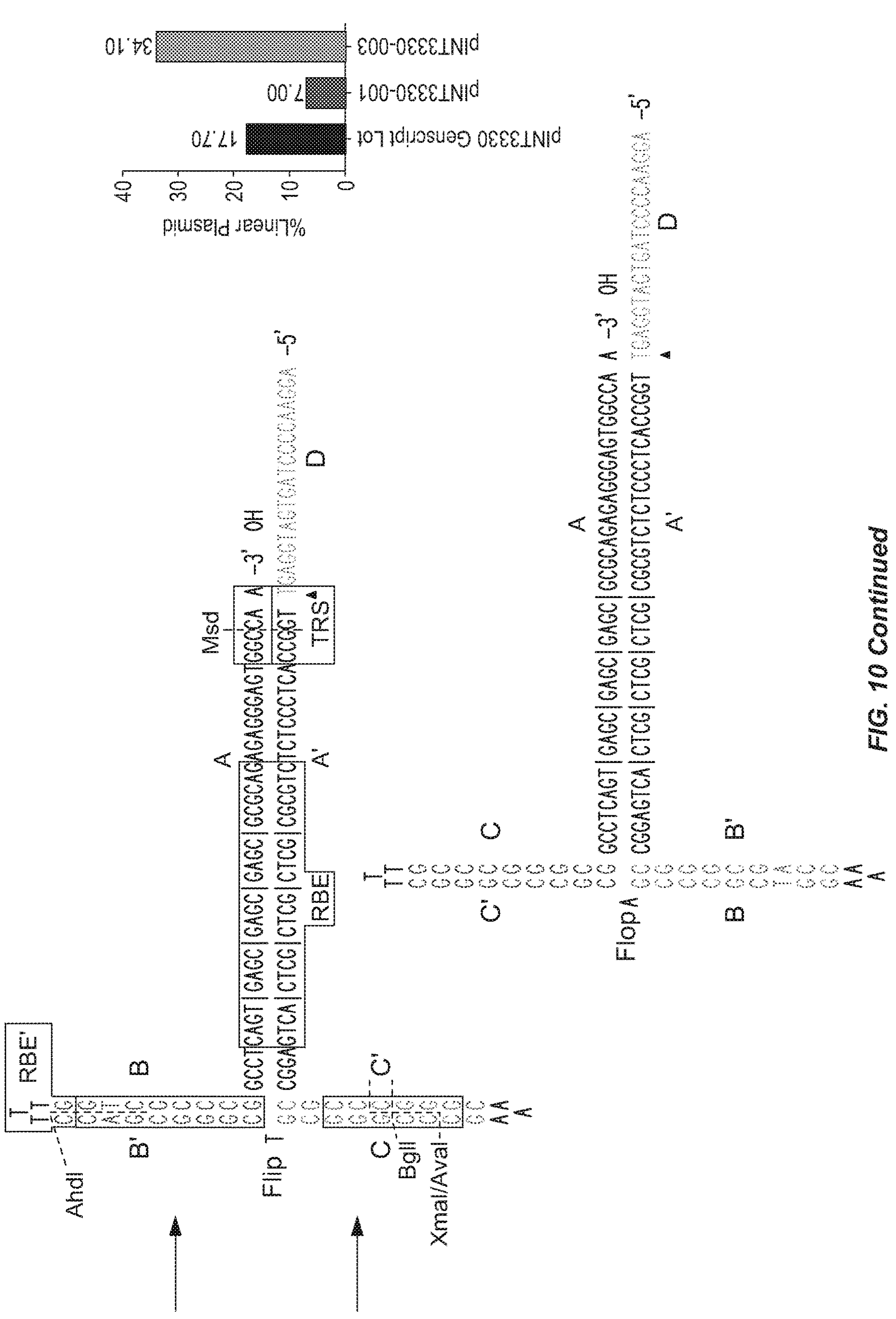

FIG. 10 shows a visualization of pINT3330 alignment to a reference sequence using PacBio CCS (Circular Consensus Sequence) data. The data show a high-quality sequence (0.2% error rate), and a single read covers the entire plasmid. Subsequent high-quality alignments lead to identification of all the different variants in the plasmid population. FIG. 10 shows an alignment of the pINT3330 plasmid in the left ITR region. Almost all dominant variants are shown—BB' deletion, CC' deletion, and the L-ITR flop allele.

Figure 11:
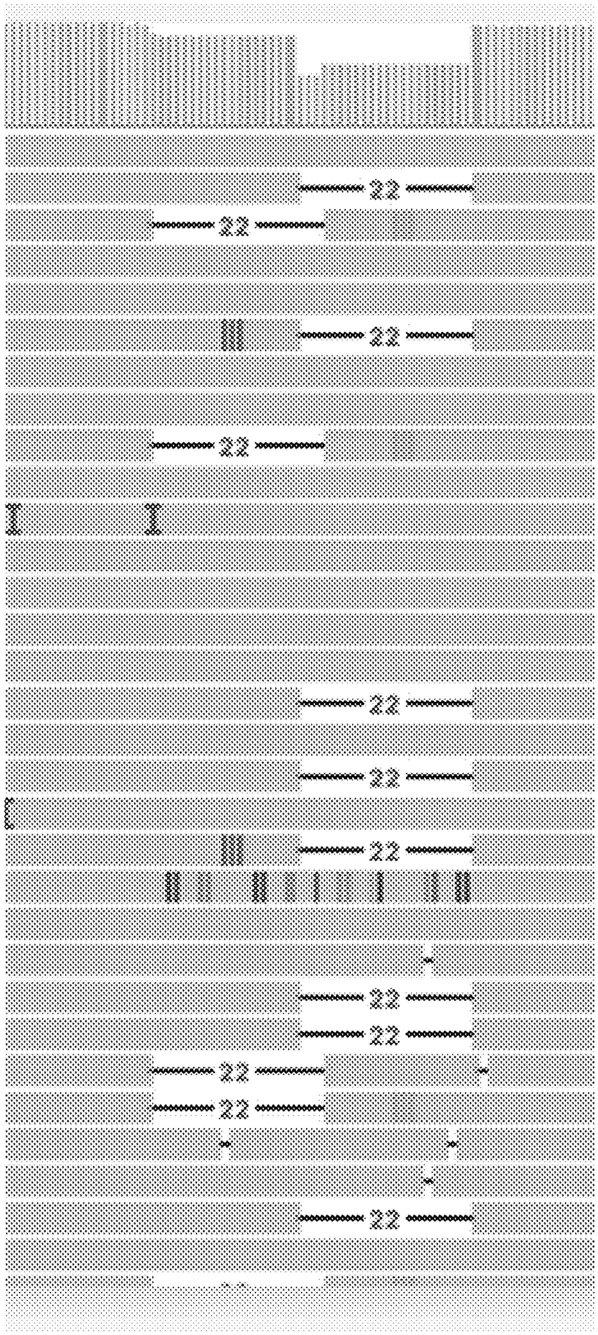
FIG. 11 shows a region of an IGV that illustrates that some deletions are associated with a triple SNP mutation whereas some are not.

FIG. 11 shows that some deletions are associated with a triple SNP mutation whereas some are not, which is an alignment visualization issue. The reads with the deletion and SNPs can be explained as flop alleles carrying a simple deletion. Both events lead to the same exact DNA sequence, but the latter may be considered more biologically plausible.

Figure 12:
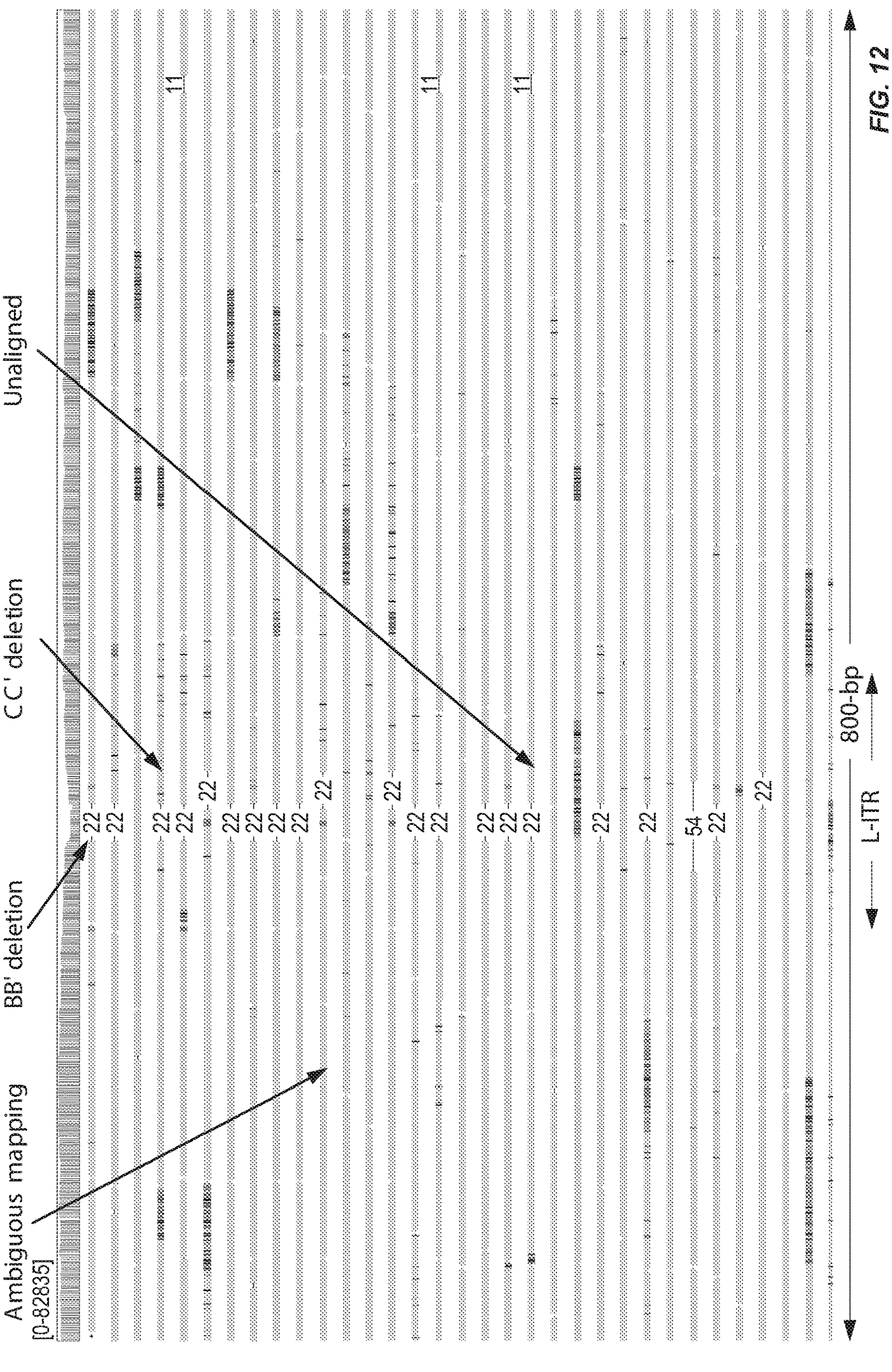
FIG. 12 shows another visualization of pINT alignment to a reference sequence using Illumina 150-bp data.
Figure 12:
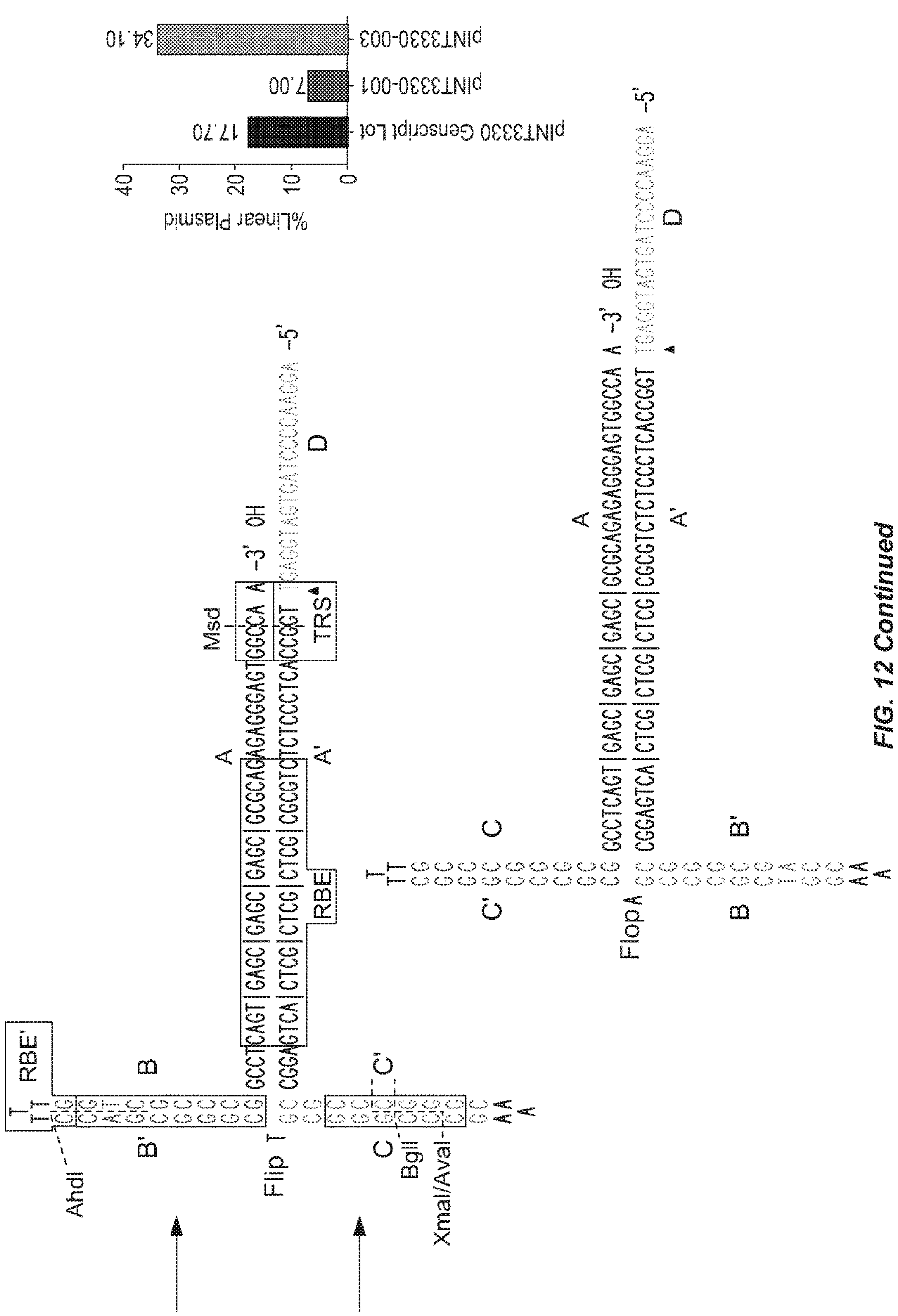

FIG. 12 shows another visualization of pINT3330 alignment to a reference sequence using Illumina 150-bp data. Short reads (150-bp) with low error rates (0.3%). Analysis pipelines miss the flip-to-flop change, but somewhat accurately quantify hairpin deletions.

Figure 13:
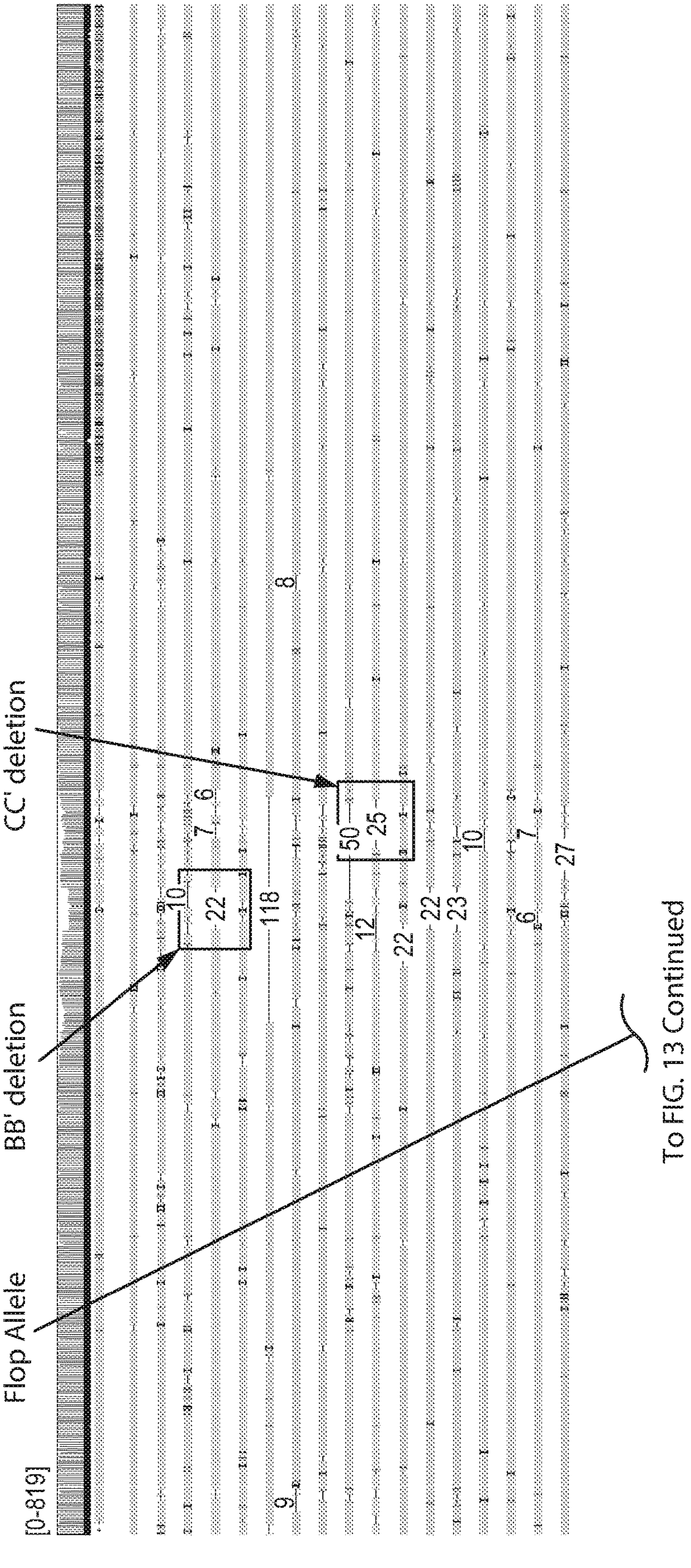
FIG. 13 shows another visualization of pINT alignment to a reference sequence using Oxford Nanopore External data source (Plasmidsaurus).
Figure 13:
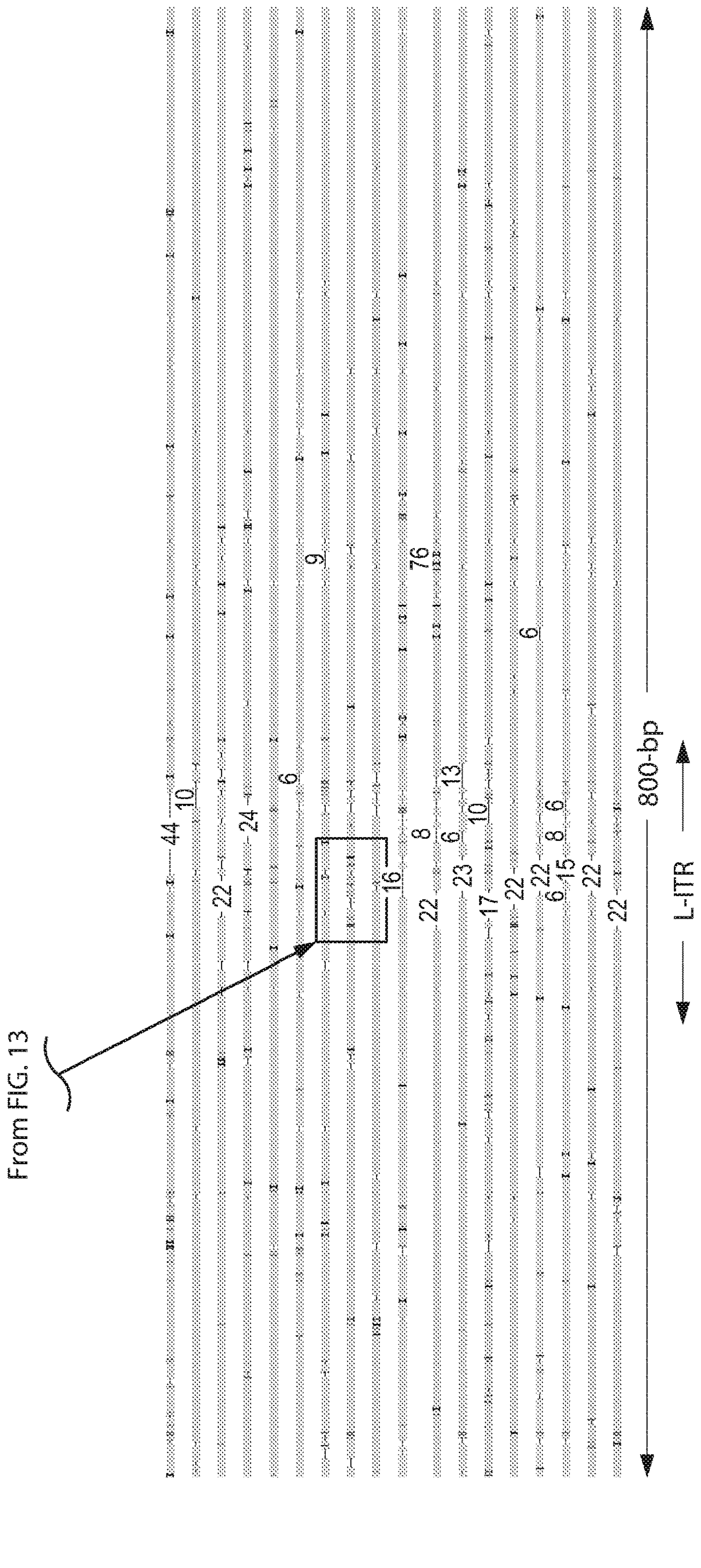
Figure 13:
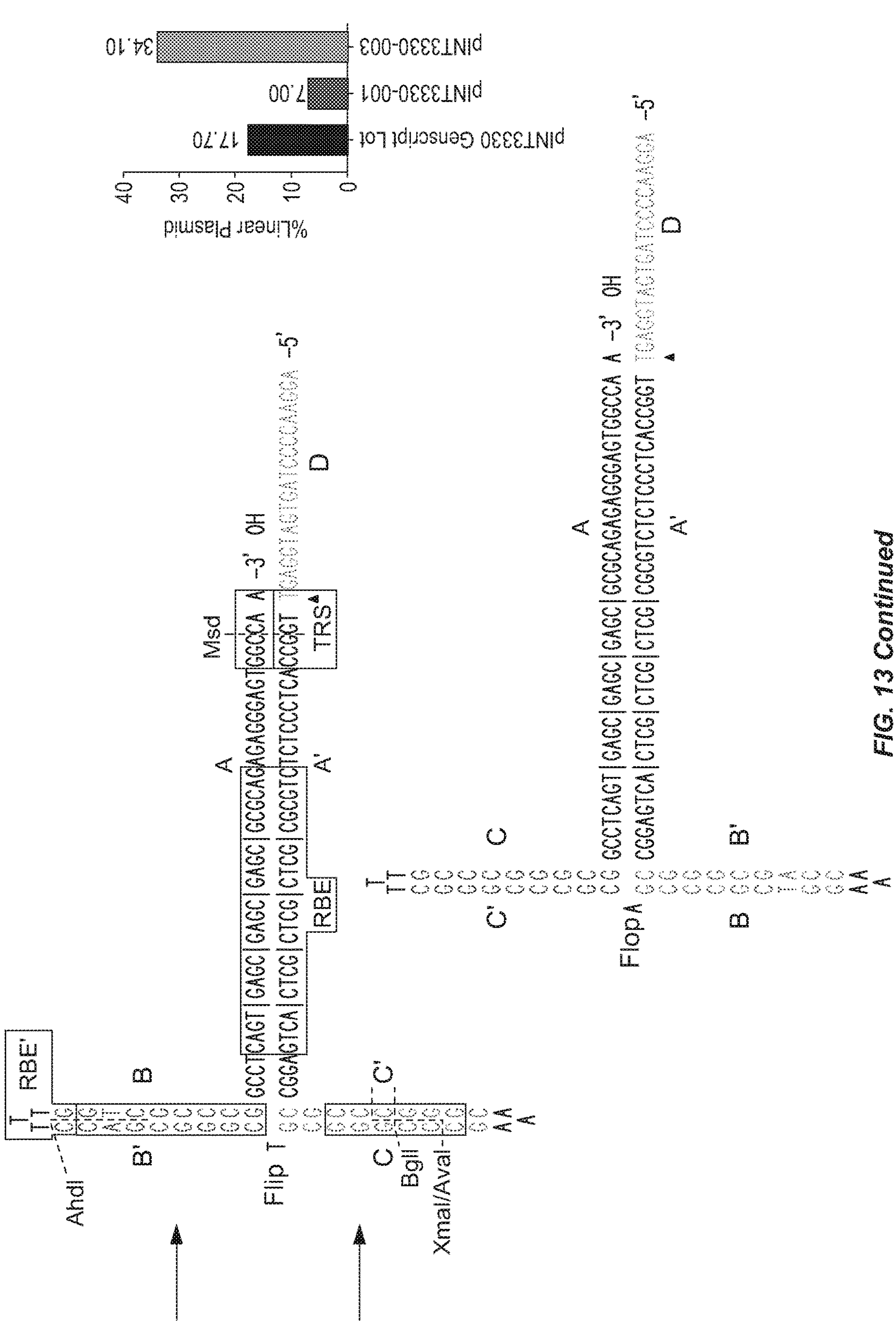

FIG. 13 shows another visualization of pINT3330 alignment to a reference sequence using Oxford Nanopore—External data source (Plasmidsaurus). The data shows a noisy, long-read data with high error rate (3.9%). The signal of the variants exist, is not suitable to accurate variant calling.

Figure 14:
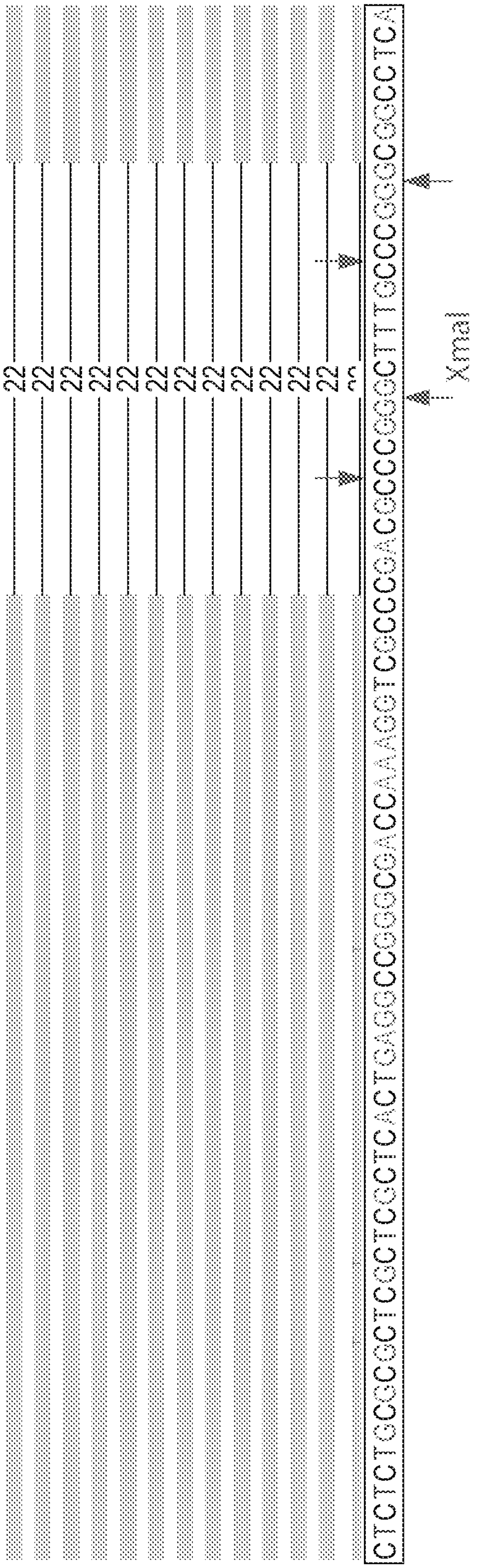
FIG. 14 shows how the L-ITR CC' deletion causes the linear isoform of FIX plasmid.
Figure 14:
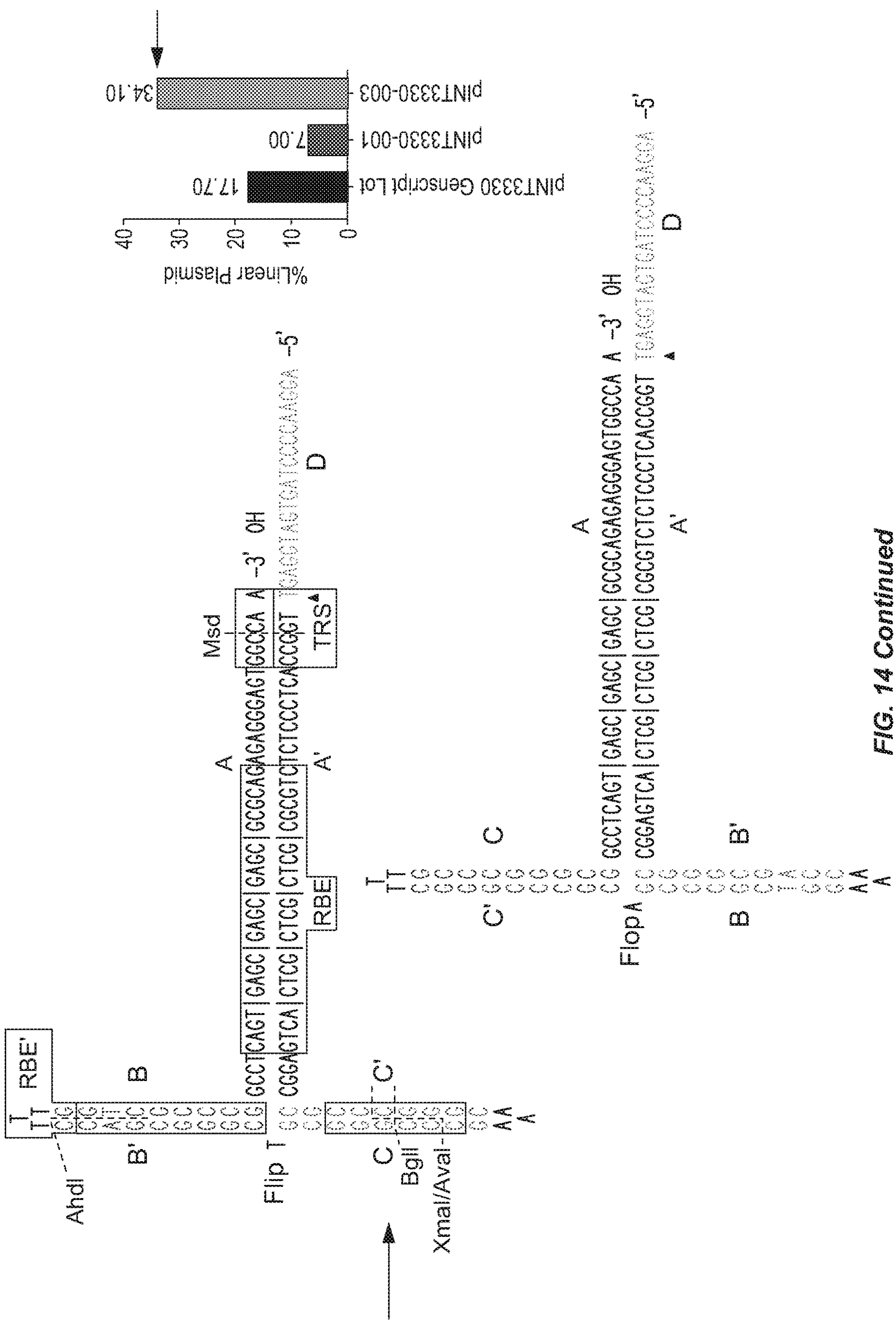

FIG. 14 shows L-ITR CC' deletion causes the linear isoform of FIX plasmid. ~99.5% of R-ITR sequences have no mutations. A change in this locus is detectable with a XmaI assay for ITRs, but the change can be challenging to characterize without sequencing. After deletion, L-ITR loses the XmaI restriction site, but R-ITR retains it leading to the linear isoform of the plasmid. Pacbio, Illumina and CE assay report similar abundance of the linear isoform.

| | Sequencing Type | | |
|---|---|---|---|
| Variant Type | PacBio | Illumina - 150 bp | CE assay |
| L-ITR CC' deletion | 39.7% | 32.7% | 34.1% |

Figure 15:
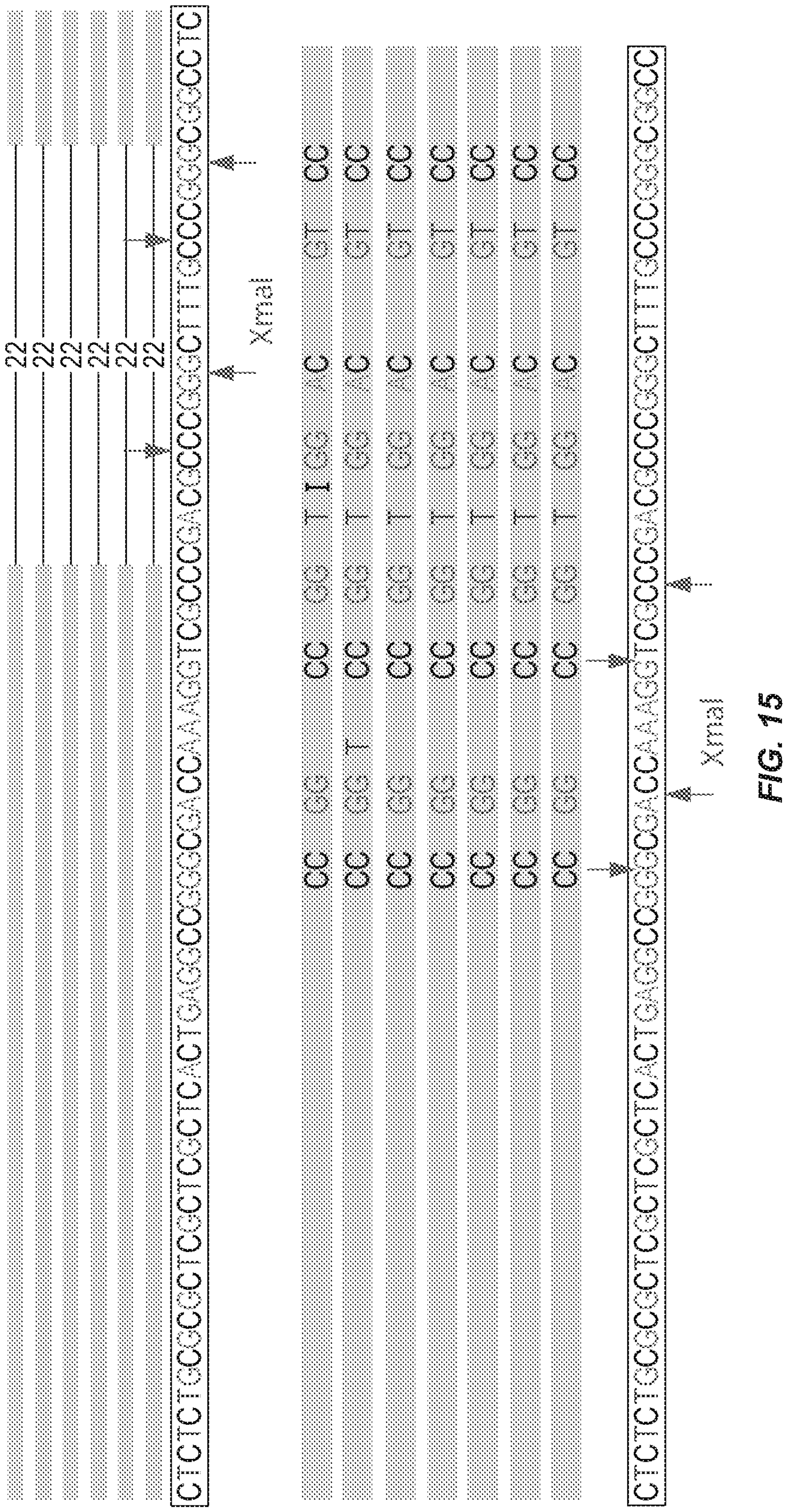
FIG. 15 shows a L-ITR BB' deletion.
Figure 15:
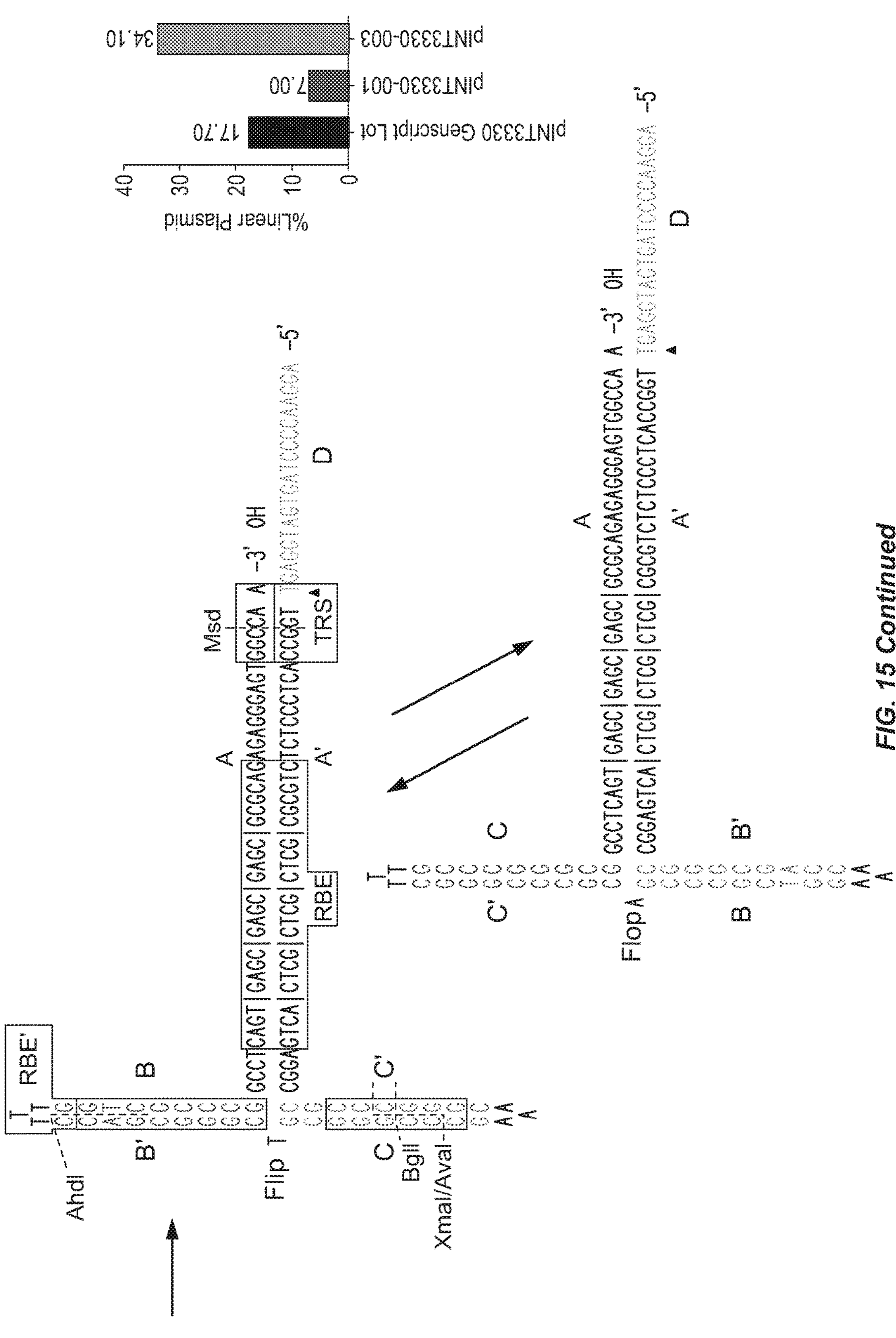

FIG. 15 shows a L-ITR BB' deletion that escapes the Xmal restriction enzyme based assay detection, because it leaves the restriction enzyme site intact. However, Pacio sequencing finds additional mutations in L-TR. Plasmids with these variants retain the Xma cut site in the L-ITR. BB' hairpin deletion. The process involves a flip to flop configuration change.

| | Sequencing Type | | |
|---|---|---|---|
| Variant Type | PacBio | Illumina - 150 bp | CE assay |
| BB' deletion | 11.4% | 5.4% | N/A |
| Flip to Flop | 7.2% | 7.8%* | N/A |

*requires manual analysis

Figure 16:
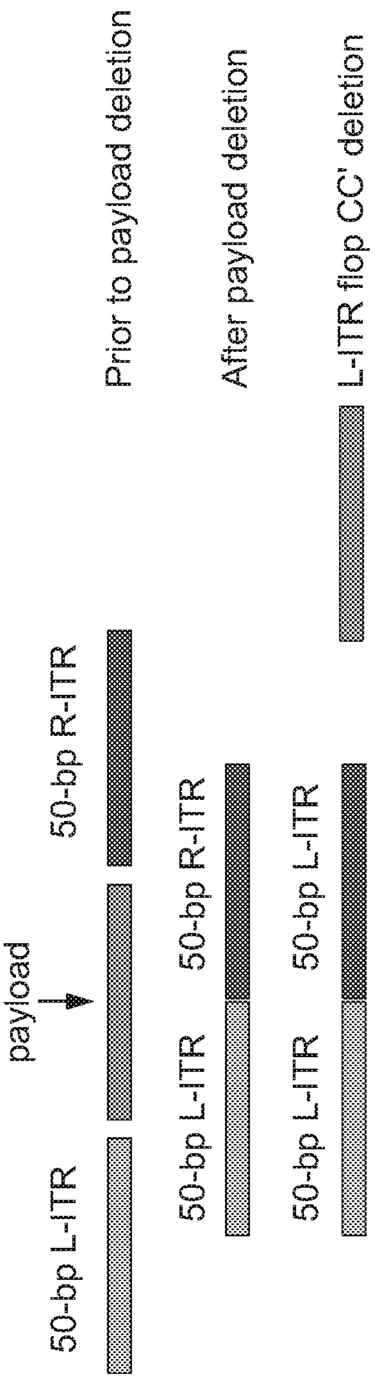
FIG. 16 shows how a payload deletion creates a 100-bp identical motif as the L-ITR CC' deletion.

FIG. 16 shows how payload deletion creates a 100-bp identical motif as the L-ITR CC' deletion, which can confuse some short-read pipelines into wrongly quantifying either mutations. Illumina over-estimates the allele frequency. Other plasmid deletions are wrongly counted as the payload deletion allele.

| | Sequencing Type | | |
|---|---|---|---|
| Variant Type | PacBio | Illumina - 150 bp | CE assay |
| Payload deletion | 0.1% | 5.6% | 0.5% |

Figure 17:
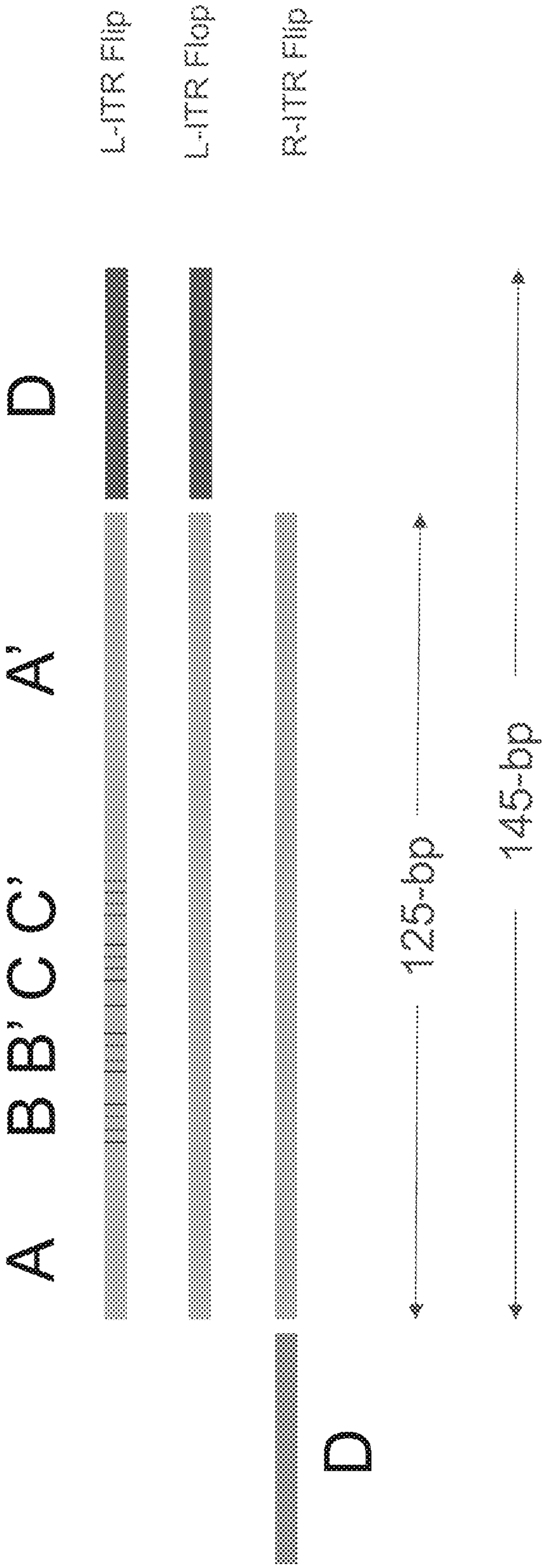
FIG. 17 shows a large region of homology (125-bp) between the L-ITR flop sequence and the R-ITR flip sequence.

FIG. 17 shows sequence homology between ITR sequences. FIG. 17 shows a large region of homology (125-bp) between the L-ITR flop sequence and the R-ITR flip sequence. This can also cause alignment issues with short-read sequences. Flop allele is detected in Illumina raw data, but is missed in analysis pipelines.

The present methods and systems may be computer-implemented. FIG. 18 shows a block diagram depicting a system/environment 1800 comprising non-limiting examples of a computing device 1801 and a server 1802 connected through a network 1804. In an aspect, some or all steps (e.g., receiving of sequence markers, extracting, clustering, merging, and/or the like) of any described method herein may be performed via a computing device(s) as described herein. The computing device 1801 may comprise one or multiple computers configured to generate and/or store sequencing (e.g., genomic) data 1829, software 1822 (e.g., alignment software, mapping software, and the like), and the like. The sequencing data 1829 may comprise, for example, any data related to, or comprising, any of the genomes, genotypes, sequences, sequence data, genomic data, a combination thereof, and/or the like as described herein. The server 1802 may comprise one or multiple computers configured to store the sequencing data 1829. Multiple servers 1802 may communicate with the computing device 1801 via the through the network 1804.

The computing device 1801 and the server 1802 may each be a computer that, in terms of hardware architecture, generally includes a processor 1808, system memory 1810, input/output (I/O) interfaces 1812, and network interfaces 1814. These components (1808, 1810, 1812, and 1814) are communicatively coupled via a local interface 1816. The local interface 1816 may be, for example, but not limited to, one or more buses or other wired or wireless connections, as is known in the art. The local interface 1816 may have additional elements, which are omitted for simplicity, such as controllers, buffers (caches), drivers, repeaters, and receivers, to enable communications. Further, the local interface may include address, control, and/or data connections to enable appropriate communications among the aforementioned components.

The processor 1808 may be a hardware device for executing software, particularly that stored in system memory 1810. The processor 1808 may be any custom made or commercially available processor, a central processing unit (CPU), an auxiliary processor among several processors associated with the computing device 1801 and the server 1802, a semiconductor-based microprocessor (in the form of a microchip or chip set), or generally any device for executing software instructions. When the computing device 1801 and/or the server 1802 is in operation, the processor 1808 may execute software stored within the system memory 1810, to communicate data to and from the system memory 1810, and to generally control operations of the computing device 1801 and the server 1802 pursuant to the software.

The I/O interfaces 1812 may be used to receive user input from, and/or for providing system output to, one or more devices or components. User input may be provided via, for example, a keyboard and/or a mouse. System output may be provided via a display device and a printer (not shown). I/O interfaces 1812 may include, for example, a serial port, a parallel port, a Small Computer System Interface (SCSI), an infrared (IR) interface, a radio frequency (RF) interface, and/or a universal serial bus (USB) interface.

The network interface 1814 may be used to transmit and receive from the computing device 1801 and/or the server 1802 on the network 1804. The network interface 1814 may include, for example, a 10BaseT Ethernet Adaptor, a 10BaseT Ethernet Adaptor, a LAN PHY Ethernet Adaptor, a Token Ring Adaptor, a wireless network adapter (e.g., WiFi, cellular, satellite), or any other suitable network interface device. The network interface 1814 may include address, control, and/or data connections to enable appropriate communications on the network 1804.

The system memory 1810 may include any one or combination of volatile memory elements (e.g., random access memory (RAM, such as DRAM, SRAM, SDRAM, etc.)) and nonvolatile memory elements (e.g., ROM, hard drive, tape, CDROM, DVDROM, etc.). Moreover, the system memory 1810 may incorporate electronic, magnetic, optical, and/or other types of storage media. Note that the system memory 1810 may have a distributed architecture, where various components are situated remote from one another, but may be accessed by the processor 1808.

The software in system memory 1810 may include one or more software programs, each of which comprises an ordered listing of executable instructions for implementing logical functions. In the example of FIG. 18, the software in the system memory 1810 of the computing device 1801 may comprise the sequencing data 1829, the software 1822, and a suitable operating system (O/S) 1818. In the example of FIG. 18, the software in the system memory 1810 of the server 1802 may comprise the sequencing data 1829 and a suitable operating system (O/S) 1818. The operating system 1818 essentially controls the execution of other computer programs and provides scheduling, input-output control, file and data management, memory management, and communication control and related services.

The computing device 1801 and the server 1802 may each be in communication (e.g., via the network 1804) with a sequencer 1830 as shown in FIG. 18. The sequencer 1830 may be configured to determine a sequence of a biomolecule, e.g., a nucleic acid such as DNA or RNA. The sequencer 1830 may employ any suitable sequencing method(s). In some embodiments, the sequencer 1830 may comprise, and/or perform the functionality of, a gene analyzer such as, for example, gene analyzers commercially available from Illumina or Applied Biosystems.

For purposes of illustration, application programs and other executable program components such as the operating system 1818 are shown herein as discrete blocks, although it is recognized that such programs and components may reside at various times in different storage components of the computing device 1801 and/or the server 1802. An implementation of the software 1822 may be stored on or transmitted across some form of computer readable media. Any of the disclosed methods may be performed by computer readable instructions embodied on computer readable media. Computer readable media may be any available media that may be accessed by a computer. By way of example and not meant to be limiting, computer readable media may comprise "computer storage media" and "communications media." "Computer storage media" may comprise volatile and non-volatile, removable and non-removable media implemented in any methods or technology for storage of information such as computer readable instructions, data structures, program modules, or other data. Exemplary computer storage media may comprise RAM, ROM, EEPROM, flash memory or other memory technology, CD-ROM, digital versatile disks (DVD) or other optical storage, magnetic cassettes, magnetic tape, magnetic disk storage or other magnetic storage devices, or any other medium which may be used to store the desired information and which may be accessed by a computer.

Figure 19:
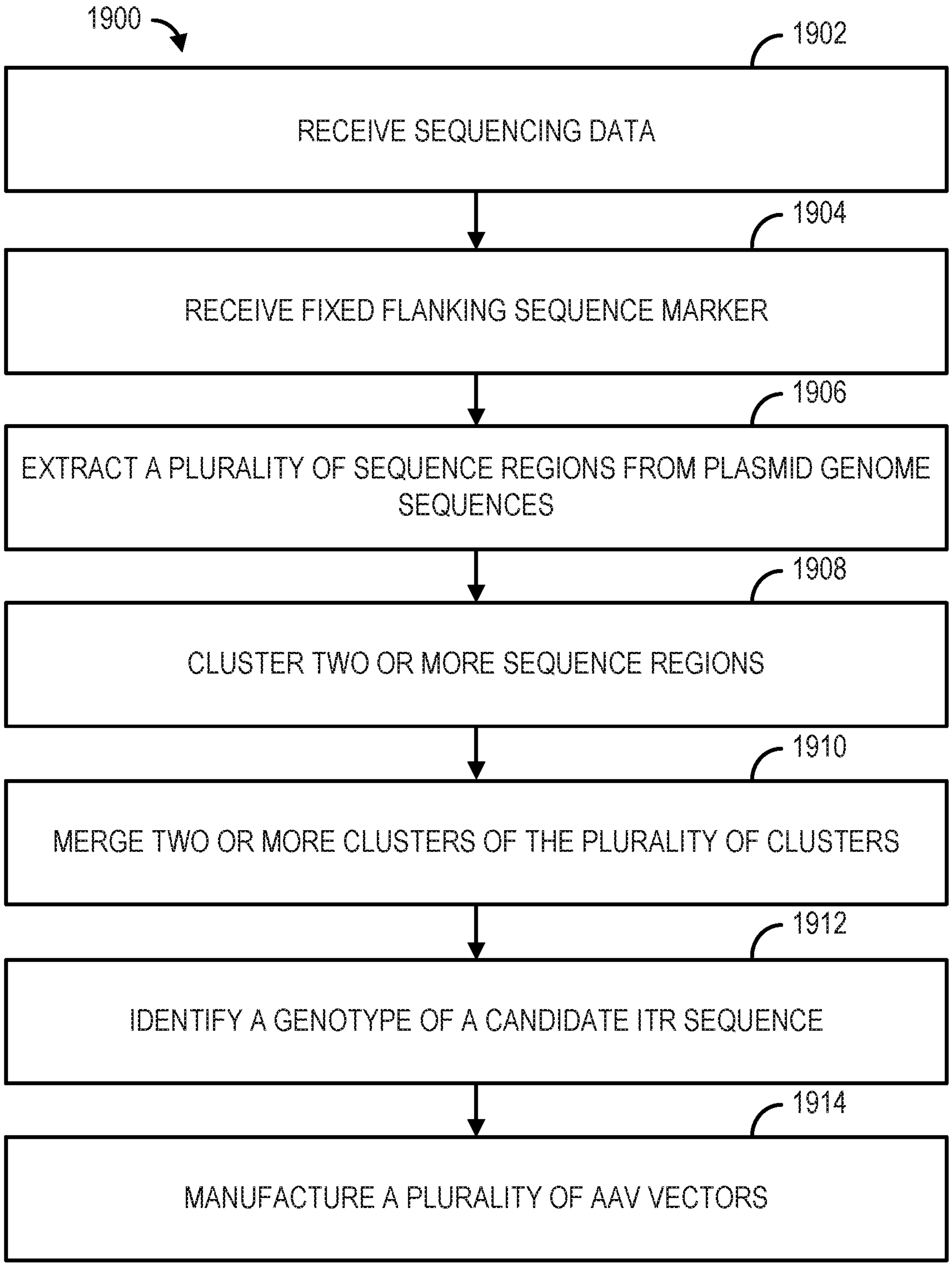
FIG. 19 shows an example method for assessing ITRs in plasmids.

In an embodiment, the software 1822 may be configured to perform a method 1900, shown in FIG. 19. The method 1900 may be performed in whole or in part by a single computing device, a plurality of electronic devices, and the like. The method 1900 may comprise receiving sequencing data at 1902. Sequencing data may comprise a plurality of plasmid genome sequences. Receiving sequencing data may comprise determining sequencing data. Receiving sequencing data may comprise sequencing genomes of a plurality of plasmids to obtain a plurality of plasmid genome sequences. For example, via sequencer 1830. Sequencing the plurality of plasmids may comprise sequencing via long read sequencing or circular consensus sequencing.

The method 1900 may comprise receiving a specification of a fixed flanking sequence marker at 1904. The specification may comprise any form of data structure, for example a string, a flat file, and the like. The fixed flanking sequence marker may comprise a sequence of at least 15 nucleotides. The fixed flanking sequence marker may comprises at least a portion of a transgene to be delivered by an AAV vector.

The method 1900 may comprise extracting a plurality of sequence regions from the plasmid genome sequences at 1906. Sequence regions may be extracted from each plasmid genome sequence. Sequence regions may be extracted based on the presence of the fixed flanking sequence markers in the plasmid genome sequence. Each sequence region may be within the fixed flanking sequence markers. Each sequence region may comprise a candidate inverted terminal repeat (ITR) sequence.

Extracting the plurality of sequence regions may comprise locating, in the plasmid genome sequence, the fixed flanking sequence marker and extracting the sequence region from the fixed flanking sequence marker in a 5' to 3' direction relative to the orientation of the fixed flanking sequence marker.

Extracting the plurality of sequence regions comprises locating, in the plasmid genome sequence, the fixed flanking sequence marker and extracting the sequence region from the fixed flanking sequence marker in a 3' to 5' direction relative to the orientation of the fixed flanking sequence marker.

Extracting the plurality of sequence regions comprises locating, in the plasmid genome sequence, a plurality of fixed flanking sequence markers and extracting the sequence region between the plurality of fixed flanking sequence markers.

The method 1900 may comprise clustering two or more sequence regions of the plurality of sequence regions to generate a plurality of clusters at 1908. Clustering may be based on sequence identity. The clustering may be based on perfect sequence identity. The clustering may be based on at least 99% sequence identity. The clustering may be based on at least 98% sequence identity.

The method 1900 may further comprise, for each sequence region of the plurality of sequence regions determining a length of that sequence region and excluding that sequence region from the clustering step if its length is above a first threshold or below a second threshold. The first threshold may be about 700 base pairs long and the second threshold may be about 150 base pairs long.

The method 1900 may comprise merging two or more clusters of the plurality of clusters at 1910. Merging two or more clusters of the plurality of clusters may be based on an alignment between their corresponding sequence regions. Merging two or more clusters of the plurality of clusters may comprise iteratively merging two or more clusters of the plurality of clusters into one or more modified clusters. Each iterative merging of two or more clusters of the plurality of clusters may be based on aligning a representative sequence region from each cluster using a different sequence identity for each iteration. Iteratively merging two or more clusters of the plurality of clusters is performed until a predetermined number clusters is generated. The predetermined number of clusters is 1.

The method 1900 may further comprise generating, based on sequence regions associated with clusters comprising two or more sequence regions, a database of ITR genotypes. The method 1900 may further comprise manufacturing recombinant AAV vectors based on the database of ITR genotypes.

The method 1900 may comprise identifying a genotype of a candidate ITR sequence at 1912. Identifying a genotype of a candidate ITR sequence may be performed when a single cluster remains. Identifying a genotype of a candidate ITR sequence may be based on a local alignment. Identifying a genotype of a candidate ITR sequence may be based on aligning the candidate ITR sequence to a reference sequence. The reference sequence may be a reference ITR sequence. The reference ITR sequence may be a wild type ITR sequence. The reference ITR sequence may be an engineered ITR sequence. The genotype of the candidate ITR sequence may be identical to a wild type ITR sequence or an engineered ITR sequence.

The method 1900 may comprise manufacturing a plurality of AAV vectors at 1914. Manufacturing a plurality of AAV vectors may be based on the genotype of the candidate ITR sequence. Manufacturing a plurality of AAV vectors may be based on the genotype of the candidate ITR sequence being identical to a wild type ITR sequence or an engineered ITR sequence. Manufacturing a plurality of AAV vectors may comprise manufacturing a plurality of AAV vectors using plasmids having ITR sequences with the genotype of the candidate ITR sequence.

The method 1900 may further comprise packaging, based on the genotype of the candidate ITR sequence being identical to a wild type ITR sequence or an engineered ITR sequence, the plurality of AAV vectors for distribution.

The method 1900 may further comprise administering to a human subject a therapeutically effective amount of the manufactured recombinant AAV vectors.

Figure 20:
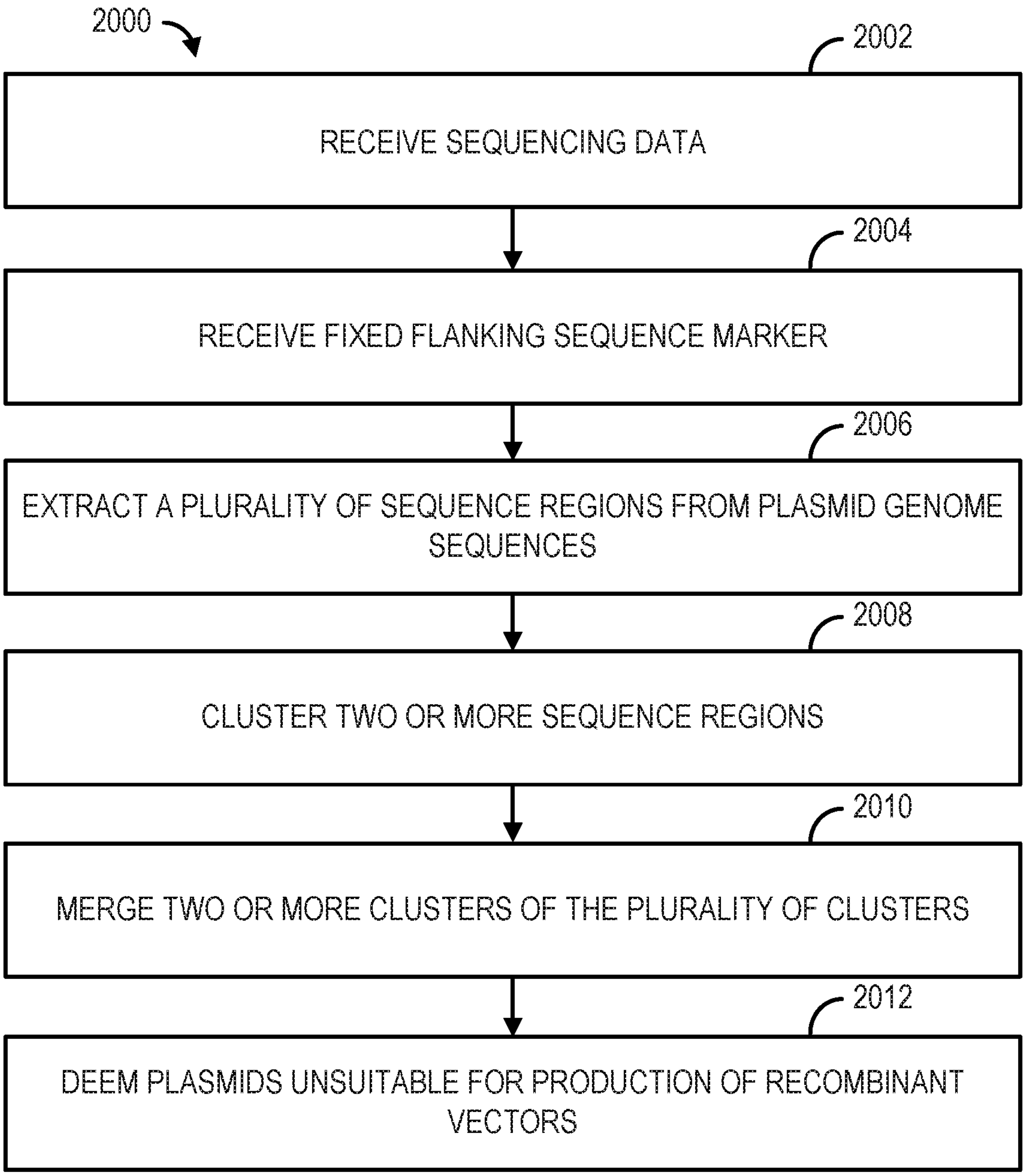
FIG. 20 shows an example method for assessing ITRs in plasmids.

In an embodiment, the software 1822 may be configured to perform a method 2000, shown in FIG. 20. The method 2000 may be performed in whole or in part by a single computing device, a plurality of electronic devices, and the like. The method 2000 may comprise receiving sequencing data at 2002. Sequencing data may comprise a plurality of plasmid genome sequences. Receiving sequencing data may comprise determining sequencing data. Receiving sequencing data may comprise sequencing genomes of a plurality of plasmids to obtain a plurality of plasmid genome sequences. For example, via sequencer 1830. Sequencing the plurality of plasmids may comprise sequencing via long read sequencing or circular consensus sequencing.

The method 2000 may comprise receiving a specification of a fixed flanking sequence marker at 2004. The specification may comprise any form of data structure, for example a string, a flat file, and the like. The fixed flanking sequence marker may comprise a sequence of at least 15 nucleotides. The fixed flanking sequence marker may comprises at least a portion of a transgene to be delivered by an AAV vector.

The method 2000 may comprise extracting a plurality of sequence regions from the plasmid genome sequences at 2006. Sequence regions may be extracted from each plasmid genome sequence. Sequence regions may be extracted based on the presence of the fixed flanking sequence markers in the plasmid genome sequence. Each sequence region may be within the fixed flanking sequence markers. Each sequence region may comprise a candidate inverted terminal repeat (ITR) sequence.

Extracting the plurality of sequence regions may comprise locating, in the plasmid genome sequence, the fixed flanking sequence marker and extracting the sequence region from the fixed flanking sequence marker in a 5' to 3' direction relative to the orientation of the fixed flanking sequence marker.

Extracting the plurality of sequence regions comprises locating, in the plasmid genome sequence, the fixed flanking sequence marker and extracting the sequence region from the fixed flanking sequence marker in a 3' to 5' direction relative to the orientation of the fixed flanking sequence marker.

Extracting the plurality of sequence regions comprises locating, in the plasmid genome sequence, a plurality of fixed flanking sequence markers and extracting the sequence region between the plurality of fixed flanking sequence markers.

The method 2000 may comprise clustering two or more sequence regions of the plurality of sequence regions to generate a plurality of clusters at 2008. Clustering may be based on sequence identity. The clustering may be based on perfect sequence identity. The clustering may be based on at least 99% sequence identity. The clustering may be based on at least 98% sequence identity.

The method 2000 may further comprise, for each sequence region of the plurality of sequence regions determining a length of that sequence region and excluding that sequence region from the clustering step if its length is above a first threshold or below a second threshold. The first threshold may be about 700 base pairs long and the second threshold may be about 150 base pairs long.

The method 2000 may comprise merging two or more clusters of the plurality of clusters at 2010. Merging two or more clusters of the plurality of clusters may be based on an alignment between their corresponding sequence regions. Merging two or more clusters of the plurality of clusters may comprise iteratively merging two or more clusters of the plurality of clusters into one or more modified clusters. Each iterative merging of two or more clusters of the plurality of clusters may be based on aligning a representative sequence region from each cluster using a different sequence identity for each iteration. Iteratively merging two or more clusters of the plurality of clusters is performed until a predetermined number clusters is generated. The predetermined number of clusters is 1.

The method 2000 may further comprise generating, based on sequence regions associated with clusters comprising two or more sequence regions, a database of ITR genotypes. The method 2000 may further comprise manufacturing recombinant AAV vectors based on the database of ITR genotypes.

The method 2000 may comprise deeming the plurality of plasmids unsuitable for production of recombinant vector genomes at 2012. Deeming the plurality of plasmids unsuitable for production of recombinant vector genomes may be based on based on two or more clusters remaining after the merging. The existence of two or more clusters after merging indicates that the plurality of plasmids contains variability within the ITRs that exceeds a threshold for manufacture of AAV vectors. The method 2000 may further comprise disposing of any plasmids related to the plurality of plasmids.

Figure 21:
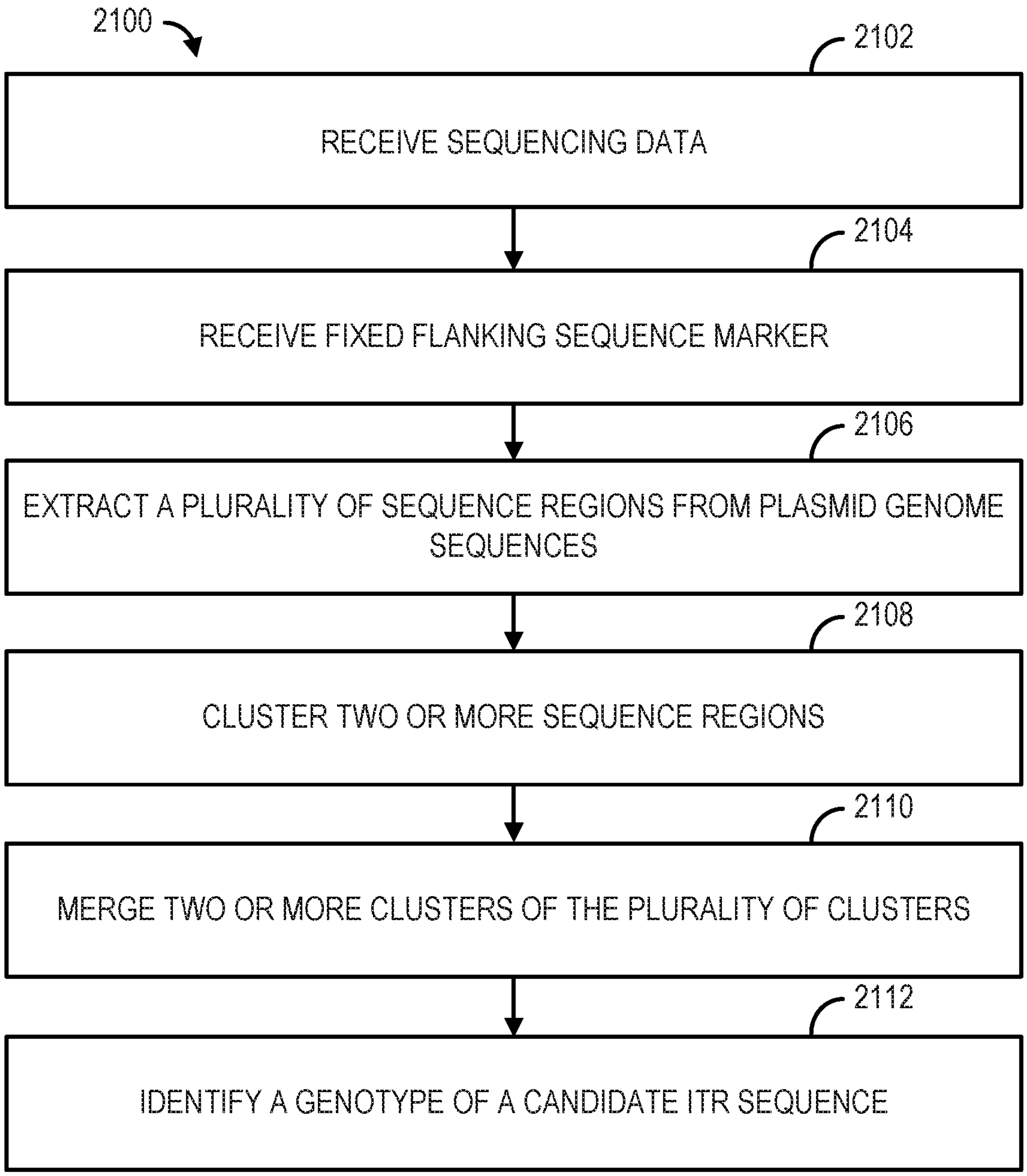
FIG. 21 shows another example method for assessing ITRs in plasmids.

In an embodiment, the software 1822 may be configured to perform a method 2100, shown in FIG. 21. The method 2100 may be performed in whole or in part by a single computing device, a plurality of electronic devices, and the like. The method 2100 may comprise receiving sequencing data at 2102. Sequencing data may comprise a plurality of plasmid genome sequences. Receiving sequencing data may comprise determining sequencing data. Receiving sequencing data may comprise sequencing genomes of a plurality of plasmids to obtain a plurality of plasmid genome sequences. For example, via sequencer 1830. Sequencing the plurality of plasmids may comprise sequencing via long read sequencing or circular consensus sequencing.

The method 2100 may comprise receiving a specification of a fixed flanking sequence marker at 2104. The specification may comprise any form of data structure, for example a string, a flat file, and the like. The fixed flanking sequence marker may comprise a sequence of at least 15 nucleotides. The fixed flanking sequence marker may comprises at least a portion of a transgene to be delivered by an AAV vector.

The method 2100 may comprise extracting a plurality of sequence regions from the plasmid genome sequences at 2106. Sequence regions may be extracted from each plasmid genome sequence. Sequence regions may be extracted based on the presence of the fixed flanking sequence markers in the plasmid genome sequence. Each sequence region may be within the fixed flanking sequence markers. Each sequence region may comprise a candidate inverted terminal repeat (ITR) sequence.

Extracting the plurality of sequence regions may comprise locating, in the plasmid genome sequence, the fixed flanking sequence marker and extracting the sequence region from the fixed flanking sequence marker in a 5' to 3' direction relative to the orientation of the fixed flanking sequence marker.

Extracting the plurality of sequence regions comprises locating, in the plasmid genome sequence, the fixed flanking sequence marker and extracting the sequence region from the fixed flanking sequence marker in a 3' to 5' direction relative to the orientation of the fixed flanking sequence marker.

Extracting the plurality of sequence regions comprises locating, in the plasmid genome sequence, a plurality of fixed flanking sequence markers and extracting the sequence region between the plurality of fixed flanking sequence markers.

The method 2100 may comprise clustering two or more sequence regions of the plurality of sequence regions to generate a plurality of clusters at 2108. Clustering may be based on sequence identity. The clustering may be based on perfect sequence identity. The clustering may be based on at least 99% sequence identity. The clustering may be based on at least 98% sequence identity.

The method 2100 may further comprise, for each sequence region of the plurality of sequence regions determining a length of that sequence region and excluding that sequence region from the clustering step if its length is above a first threshold or below a second threshold. The first threshold may be about 700 base pairs long and the second threshold may be about 150 base pairs long.

The method 2100 may comprise merging two or more clusters of the plurality of clusters at 2110. Merging two or more clusters of the plurality of clusters may be based on an alignment between their corresponding sequence regions. Merging two or more clusters of the plurality of clusters may comprise iteratively merging two or more clusters of the plurality of clusters into one or more modified clusters. Each iterative merging of two or more clusters of the plurality of clusters may be based on aligning a representative sequence region from each cluster using a different sequence identity for each iteration. Iteratively merging two or more clusters of the plurality of clusters is performed until a predetermined number clusters is generated. The predetermined number of clusters is 1.

The method 2100 may further comprise generating, based on sequence regions associated with clusters comprising two or more sequence regions, a database of ITR genotypes and manufacturing recombinant AAV vectors based on the database of ITR genotypes.

The method 2100 may comprise identifying a genotype of a candidate ITR sequence of a representative sequence region of a single remaining cluster at 2112. Identifying a genotype of a candidate ITR sequence of the representative sequence region may be performed when a single cluster remains after said merging at 2110. Identifying a genotype of a candidate ITR sequence may be based on a local alignment. Identifying a genotype of a candidate ITR sequence may be based on aligning the candidate ITR sequence to a reference sequence. The reference sequence may be a reference ITR sequence. The reference ITR sequence may be a wild type ITR sequence. The reference ITR sequence may be an engineered ITR sequence. The genotype of the candidate ITR sequence may be identical to a wild type ITR sequence or an engineered ITR sequence.

The method 2100 may further comprise manufacturing a plurality of AAV vectors. Manufacturing a plurality of AAV vectors may be based on the genotype of the candidate ITR sequence. Manufacturing a plurality of AAV vectors may be based on the genotype of the candidate ITR sequence being identical to a wild type ITR sequence or an engineered ITR sequence. Manufacturing a plurality of AAV vectors may comprise manufacturing a plurality of AAV vectors using plasmids having ITR sequences with the genotype of the candidate ITR sequence.

The method 2100 may further comprise packaging, based on the genotype of the candidate ITR sequence being identical to a wild type ITR sequence or an engineered ITR sequence, the plurality of AAV vectors for distribution.

The method 2100 may further comprise administering to a human subject a therapeutically effective amount of the manufactured recombinant AAV vectors.

Figure 22:
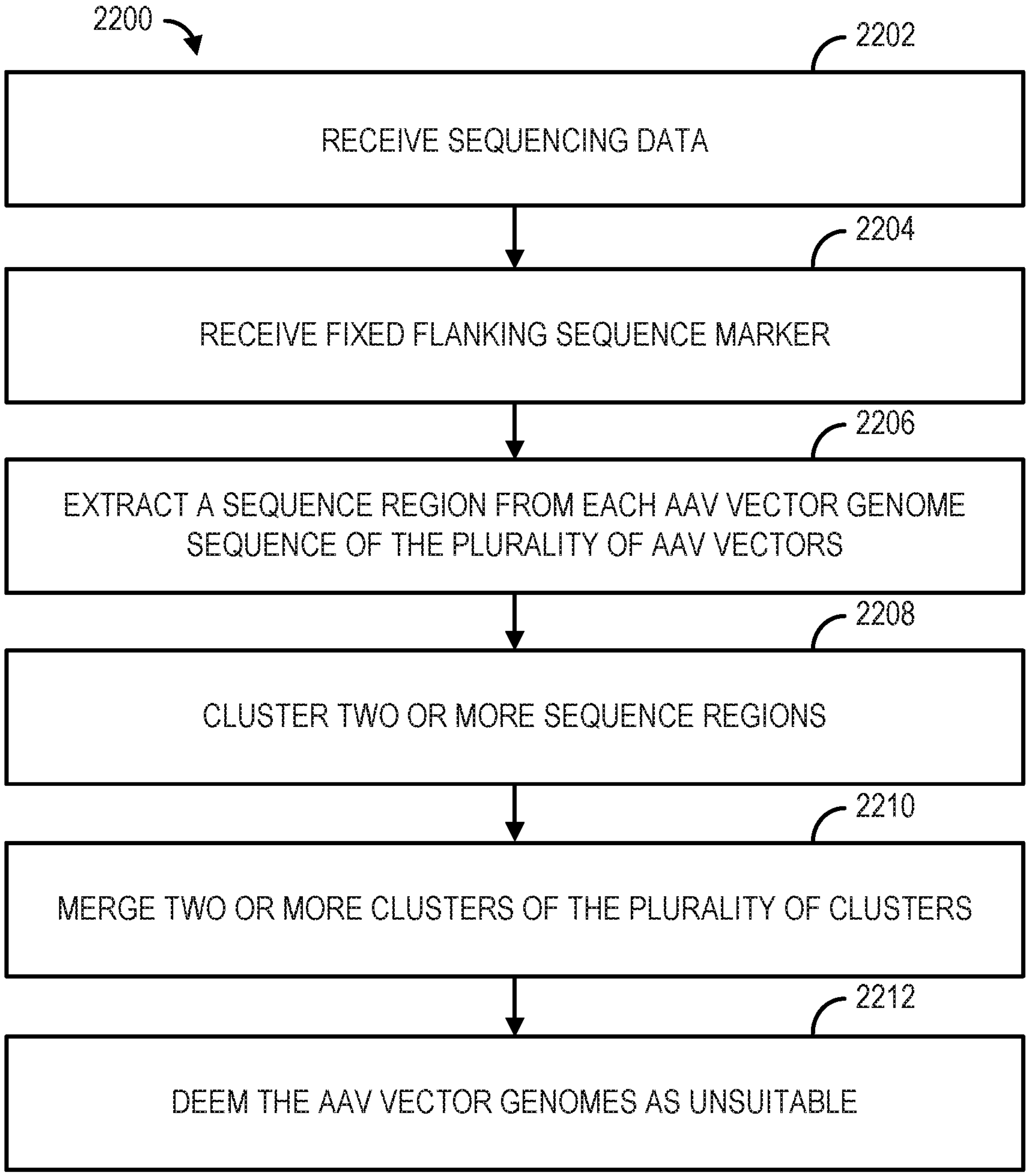
FIG. 22 shows an example method for assessing ITRs in AAV vectors.

In an embodiment, the software 1822 may be configured to perform a method 2200, shown in FIG. 22. The method 2200 may be performed in whole or in part by a single computing device, a plurality of electronic devices, and the like. The method 2200 may comprise receiving sequencing data at 2202. Sequencing data may comprise a plurality of Adeno-associated virus (AAV) vector genome sequences. Receiving sequencing data may comprise determining sequencing data. Receiving sequencing data may comprise sequencing genomes of a plurality of Adeno-associated virus (AAV) vectors to obtain a plurality of Adeno-associated virus (AAV) vector genome sequences. For example, via sequencer 1830. Sequencing the plurality of Adeno-associated virus (AAV) vectors may comprise sequencing via long read sequencing or circular consensus sequencing.

The method 2200 may comprise receiving a specification of a fixed flanking sequence marker at 2204. The specification may comprise any form of data structure, for example a string, a flat file, and the like. The fixed flanking sequence marker may comprise a sequence of at least 15 nucleotides. The fixed flanking sequence marker may comprises at least a portion of a transgene to be delivered by the plurality of AAV vectors.

The method 2200 may comprise extracting a sequence region from each AAV vector genome sequence of the plurality of AAV vectors at 2206. Sequence regions may be extracted based on the presence of the fixed flanking sequence markers in the AAV vector genome sequences. Each sequence region may be immediately to the left or immediately to the right of a fixed flanking sequence marker. Each sequence region may comprise a candidate inverted terminal repeat (ITR) sequence.

Extracting, from each AAV vector genome sequence of the plurality of AAV vectors, based on the presence of the fixed flanking sequence markers in that AAV vector genome sequence, a sequence region immediately to the left or immediately to the right of a fixed flanking sequence marker comprises locating, in the AAV vector genome sequence, the fixed flanking sequence marker and extracting the sequence region from the fixed flanking sequence marker in a 5' to 3' direction relative to the orientation of the fixed flanking sequence marker.

Extracting, from each AAV vector genome sequence of the plurality of AAV vectors, based on the presence of the fixed flanking sequence markers in that AAV vector genome sequence, a sequence region immediately to the left or immediately to the right of a fixed flanking sequence marker comprises locating, in the AAV vector genome sequence, the fixed flanking sequence marker and extracting the sequence region from the fixed flanking sequence marker in a 3' to 5' direction relative to the orientation of the fixed flanking sequence marker.

Extracting, from each AAV vector genome sequence of the plurality of AAV vectors, based on the presence of the fixed flanking sequence markers in that AAV vector genome sequence, a sequence region immediately to the left or immediately to the right of a fixed flanking sequence marker comprises locating, in the AAV vector genome sequence, a plurality of fixed flanking sequence markers and extracting the sequence region between the plurality of fixed flanking sequence markers.

The method 2200 may comprise clustering two or more sequence regions of the plurality of sequence regions to generate a plurality of clusters at 2208. Clustering may be based on sequence identity. The clustering may be based on perfect sequence identity. The clustering may be based on at least 99% sequence identity. The clustering may be based on at least 98% sequence identity.

The method 2200 may further comprise, for each sequence region of the plurality of sequence regions determining a length of that sequence region and excluding that sequence region from the clustering step if its length is above a first threshold or below a second threshold. The first threshold may be about 700 base pairs long and the second threshold may be about 150 base pairs long.

The method 2200 may comprise merging two or more clusters of the plurality of clusters at 2210. Merging two or more clusters of the plurality of clusters may be based on an alignment between their corresponding sequence regions. Merging two or more clusters of the plurality of clusters may comprise iteratively merging two or more clusters of the plurality of clusters into one or more modified clusters. Each iterative merging of two or more clusters of the plurality of clusters may be based on aligning a representative sequence region from each cluster using a different sequence identity for each iteration. Iteratively merging two or more clusters of the plurality of clusters is performed until a predetermined number clusters is generated. The predetermined number of clusters is 1.

The method 2200 may further comprise generating, based on sequence regions associated with clusters comprising two or more sequence regions, a database of ITR genotypes. The method 2200 may further comprise manufacturing recombinant AAV vectors based on the database of ITR genotypes.

The method 2200 may comprise deeming the AAV vector genomes as unsuitable at 2212. Deeming the AAV vector genomes as unsuitable may be based on based on two or more clusters remaining after the merging. The existence of two or more clusters after merging indicates that the AAV vector genomes contain variability within the ITRs that exceeds a threshold for AAV vectors. The method 2200 may further comprise disposing of any AAV vectors related to the plurality of AAV vectors.

Figure 23:
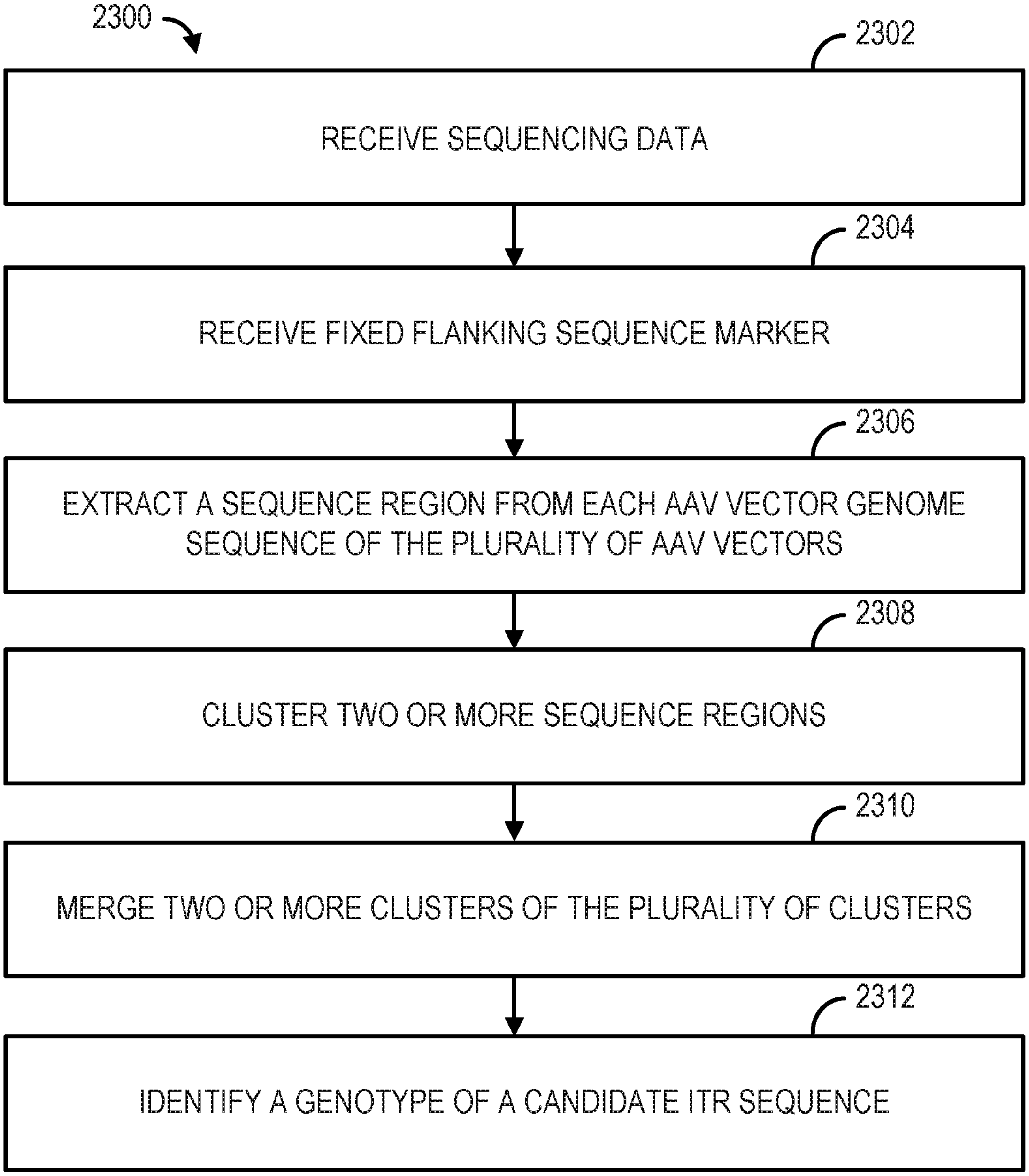
FIG. 23 shows another example method for assessing ITRs in AAV vectors.

In an embodiment, the software 1822 may be configured to perform a method 2300, shown in FIG. 23. The method 2300 may be performed in whole or in part by a single computing device, a plurality of electronic devices, and the like. The method 2300 may comprise receiving sequencing data at 2302. Sequencing data may comprise a plurality of Adeno-associated virus (AAV) vector genome sequences. Receiving sequencing data may comprise determining sequencing data. Receiving sequencing data may comprise sequencing genomes of a plurality of Adeno-associated virus (AAV) vectors to obtain a plurality of Adeno-associated virus (AAV) vector genome sequences. For example, via sequencer 1830. Sequencing the plurality of Adeno-associated virus (AAV) vectors may comprise sequencing via long read sequencing or circular consensus sequencing.

The method 2300 may comprise receiving a specification of a fixed flanking sequence marker at 2304. The specification may comprise any form of data structure, for example a string, a flat file, and the like. The fixed flanking sequence marker may comprise a sequence of at least 15 nucleotides. The fixed flanking sequence marker may comprises at least a portion of a transgene to be delivered by the plurality of AAV vectors.

The method 2300 may comprise extracting a sequence region from each AAV vector genome sequence of the plurality of AAV vectors at 2306. Sequence regions may be extracted based on the presence of the fixed flanking sequence markers in the AAV vector genome sequences. Each sequence region may be immediately to the left or immediately to the right of a fixed flanking sequence marker. Each sequence region may comprise a candidate inverted terminal repeat (ITR) sequence.

Extracting, from each AAV vector genome sequence of the plurality of AAV vectors, based on the presence of the fixed flanking sequence markers in that AAV vector genome sequence, a sequence region immediately to the left or immediately to the right of a fixed flanking sequence marker comprises locating, in the AAV vector genome sequence, the fixed flanking sequence marker and extracting the sequence region from the fixed flanking sequence marker in a 5' to 3' direction relative to the orientation of the fixed flanking sequence marker.

Extracting, from each AAV vector genome sequence of the plurality of AAV vectors, based on the presence of the fixed flanking sequence markers in that AAV vector genome sequence, a sequence region immediately to the left or immediately to the right of a fixed flanking sequence marker comprises locating, in the AAV vector genome sequence, the fixed flanking sequence marker and extracting the sequence region from the fixed flanking sequence marker in a 3' to 5' direction relative to the orientation of the fixed flanking sequence marker.

Extracting, from each AAV vector genome sequence of the plurality of AAV vectors, based on the presence of the fixed flanking sequence markers in that AAV vector genome sequence, a sequence region immediately to the left or immediately to the right of a fixed flanking sequence marker comprises locating, in the AAV vector genome sequence, a plurality of fixed flanking sequence markers and extracting the sequence region between the plurality of fixed flanking sequence markers.

The method 2300 may comprise clustering two or more sequence regions of the plurality of sequence regions to generate a plurality of clusters at 2308. Clustering may be based on sequence identity. The clustering may be based on perfect sequence identity. The clustering may be based on at least 99% sequence identity. The clustering may be based on at least 98% sequence identity.

The method 2300 may further comprise, for each sequence region of the plurality of sequence regions determining a length of that sequence region and excluding that sequence region from the clustering step if its length is above a first threshold or below a second threshold. The first threshold may be about 700 base pairs long and the second threshold may be about 150 base pairs long.

The method 2300 may comprise merging two or more clusters of the plurality of clusters at 2310. Merging two or more clusters of the plurality of clusters may be based on an alignment between their corresponding sequence regions. Merging two or more clusters of the plurality of clusters may comprise iteratively merging two or more clusters of the plurality of clusters into one or more modified clusters. Each iterative merging of two or more clusters of the plurality of clusters may be based on aligning a representative sequence region from each cluster using a different sequence identity for each iteration. Iteratively merging two or more clusters of the plurality of clusters is performed until a predetermined number clusters is generated. The predetermined number of clusters is 1.

The method 2300 may further comprise generating, based on sequence regions associated with clusters comprising two or more sequence regions, a database of ITR genotypes. The method 2300 may further comprise manufacturing recombinant AAV vectors based on the database of ITR genotypes.

The method 2300 may comprise identifying a genotype of a candidate ITR sequence of a representative sequence region of a single cluster at 2312. Identifying a genotype of a candidate ITR sequence of the representative sequence region may be performed when a single cluster remains after said merging at 2310. Identifying a genotype of a candidate ITR sequence may be based on a local alignment. Identifying a genotype of a candidate ITR sequence may be based on aligning the candidate ITR sequence to a reference sequence. The reference sequence may be a reference ITR sequence. The reference ITR sequence may be a wild type ITR sequence. The reference ITR sequence may be an engineered ITR sequence. The genotype of the candidate ITR sequence may be identical to a wild type ITR sequence or an engineered ITR sequence.

The method 2300 may further comprise manufacturing a plurality of AAV vectors. Manufacturing a plurality of AAV vectors may be based on the genotype of the candidate ITR sequence. Manufacturing a plurality of AAV vectors may be based on the genotype of the candidate ITR sequence being identical to a wild type ITR sequence or an engineered ITR sequence. Manufacturing a plurality of AAV vectors may comprise manufacturing a plurality of AAV vectors using plasmids having ITR sequences with the genotype of the candidate ITR sequence. The method 2300 may further comprise manufacturing an additional plurality of AAV vectors using the same plasmids used to manufacture the plurality of AAV vectors. The method 2300 may further comprise packaging, based on the genotype of the candidate ITR sequence being identical to a wild type ITR sequence or an engineered ITR sequence, the plurality of AAV vectors for distribution.

The method 2300 may further comprise administering to a human subject a therapeutically effective amount of the manufactured recombinant AAV vectors.

In view of the described methods, systems, and apparatuses and variations thereof, herein below are described certain more particularly described embodiments of the invention. These particularly recited embodiments should not however be interpreted to have any limiting effect on any different claims containing different or more general teachings described herein, or that the "particular" embodiments are somehow limited in some way other than the inherent meanings of the language literally used therein.

Embodiment 1 is a method of manufacturing comprising: sequencing genomes of a plurality of plasmids to obtain a plurality of plasmid genome sequences; receiving a specification of a fixed flanking sequence marker; extracting, from each plasmid genome sequence, based on the presence of the fixed flanking sequence markers in the plasmid genome sequence, a plurality of sequence regions, wherein each sequence region is within the fixed flanking sequence markers and comprises a candidate inverted terminal repeat (ITR) sequence; clustering, based on perfect sequence identity, two or more sequence regions of the plurality of sequence regions to generate a plurality of clusters; merging, based on an alignment between their corresponding sequence regions, two or more clusters of the plurality of clusters; when a single cluster remains, identifying, based on a local alignment, a genotype of a candidate ITR sequence of the single cluster; and manufacturing, based on the genotype of the candidate ITR sequence, a plurality of AAV vectors using plasmids having ITR sequences with the genotype of the candidate ITR sequence.

In Embodiment 2, the subject matter of Embodiment 1 includes, wherein sequencing the plurality of plasmids comprises sequencing via long read sequencing or circular consensus sequencing.

In Embodiment 3, the subject matter of Embodiments 1-2 includes, wherein the fixed flanking sequence marker comprises a sequence of at least 15 nucleotides.

In Embodiment 4, the subject matter of Embodiments 1-3 includes, wherein the fixed flanking sequence marker comprises at least a portion of a transgene to be delivered by an AAV vector.

In Embodiment 5, the subject matter of Embodiments 1-4 includes, wherein extracting the plurality of sequence regions comprises: locating, in the plasmid genome sequence, the fixed flanking sequence marker; and extracting the sequence region from the fixed flanking sequence marker in a 5' to 3' direction relative to the orientation of the fixed flanking sequence marker.

In Embodiment 6, the subject matter of Embodiments 1-5 includes, wherein extracting the plurality of sequence regions comprises: locating, in the plasmid genome sequence, the fixed flanking sequence marker; and extracting the sequence region from the fixed flanking sequence marker in a 3' to 5' direction relative to the orientation of the fixed flanking sequence marker.

In Embodiment 7, the subject matter of Embodiments 1-6 includes, wherein extracting the plurality of sequence regions comprises: locating, in the plasmid genome sequence, a plurality of fixed flanking sequence markers; and extracting the sequence region between the plurality of fixed flanking sequence markers.

In Embodiment 8, the subject matter of Embodiments 1-7 includes, for each sequence region of the plurality of sequence regions: determining a length of that sequence region; and excluding that sequence region from the clustering step if its length is above a first threshold or below a second threshold.

In Embodiment 9, the subject matter of Embodiment 8 includes, wherein the first threshold is about 700 base pairs long and the second threshold is about 150 base pairs long.

In Embodiment 10, the subject matter of Embodiments 1-9 includes, generating, based on sequence regions associated with clusters comprising two or more sequence regions, a database of ITR genotypes; and manufacturing recombinant AAV vectors based on the database of ITR genotypes.

In Embodiment 11, the subject matter of Embodiments 1-10 includes, wherein merging two or more clusters of the plurality of clusters comprises iteratively merging two or more clusters of the plurality of clusters into one or more modified clusters.

In Embodiment 12, the subject matter of Embodiment 11 includes, wherein each iterative merging of two or more clusters of the plurality of clusters is based on aligning a representative sequence region from each cluster using a different sequence identity for each iteration.

In Embodiment 13, the subject matter of Embodiments 11-12 includes, wherein iteratively merging two or more clusters of the plurality of clusters is performed until a predetermined number clusters is generated.

In Embodiment 14, the subject matter of Embodiment 13 includes, wherein the predetermined number of clusters is 1.

In Embodiment 15, the subject matter of Embodiments 1-14 includes, wherein the genotype of the candidate ITR sequence is identical to a wild type ITR sequence or an engineered ITR sequence.

In Embodiment 16, the subject matter of Embodiments 1-15 includes, packaging, based on the genotype of the candidate ITR sequence being identical to a wild type ITR sequence or an engineered ITR sequence, the plurality of AAV vectors for distribution.

In Embodiment 17, the subject matter of Embodiments 1-16 includes, administering to a human subject a therapeutically effective amount of the manufactured recombinant AAV vectors.

Embodiment 18 is a method, comprising: sequencing genomes of a plurality of plasmids to obtain a plurality of plasmid genome sequences; receiving a specification of a fixed flanking sequence marker; extracting, from each plasmid genome sequence, based on the presence of the fixed flanking sequence marker in that plasmid genome sequence, a plurality of sequence regions, wherein each sequence region is within the fixed flanking sequence markers and comprises a candidate inverted terminal repeat (ITR) sequence; clustering, based on sequence identity, two or more sequence regions of the plurality of sequence regions to generate a plurality of clusters; merging, based on an alignment between their corresponding sequence regions, two or more clusters of the plurality of clusters; and deeming, based on two or more clusters remaining after the merging, the plurality of plasmids unsuitable for production of recombinant vector genomes.

In Embodiment 19, the subject matter of Embodiment 18 includes, wherein sequencing the plurality of plasmids comprises sequencing via long read sequencing or circular consensus sequencing.

In Embodiment 20, the subject matter of Embodiments 18-19 includes, wherein the fixed flanking sequence marker comprises a sequence of at least 15 nucleotides.

In Embodiment 21, the subject matter of Embodiments 18-20 includes, wherein the fixed flanking sequence marker comprises at least a portion of a transgene to be delivered by an AAV vector.

In Embodiment 22, the subject matter of Embodiments 18-21 includes, wherein extracting the plurality of sequence regions comprises: locating, in the plasmid genome sequence, the fixed flanking sequence marker; and extracting the sequence region from the fixed flanking sequence marker in a 5' to 3' direction relative to the orientation of the fixed flanking sequence marker.

In Embodiment 23, the subject matter of Embodiments 18-22 includes, wherein extracting the plurality of sequence regions comprises: locating, in the plasmid genome sequence, the fixed flanking sequence marker; and extracting the sequence region from the fixed flanking sequence marker in a 3' to 5' direction relative to the orientation of the fixed flanking sequence marker.

In Embodiment 24, the subject matter of Embodiments 18-23 includes, wherein extracting the plurality of sequence regions comprises: locating, in the plasmid genome sequence, a plurality of fixed flanking sequence markers; and extracting the sequence region between the plurality of fixed flanking sequence markers.

In Embodiment 25, the subject matter of Embodiments 18-24 includes, for each sequence region of the plurality of sequence regions: determining a length of that sequence region; and excluding that sequence region from the clustering step if its length is above a first threshold or below a second threshold.

In Embodiment 26, the subject matter of Embodiment 25 includes, wherein the first threshold is about 700 base pairs long and the second threshold is about 150 base pairs long.

In Embodiment 27, the subject matter of Embodiments 18-26 includes, generating, based on sequence regions associated with clusters comprising two or more sequence regions, a database of ITR genotypes; and manufacturing recombinant AAV vectors based on the database of ITR genotypes.

In Embodiment 28, the subject matter of Embodiments 18-27 includes, wherein clustering two or more sequence regions of the plurality of sequence regions to generate a plurality of clusters is based on perfect sequence identity.

In Embodiment 29, the subject matter of Embodiments 18-28 includes, wherein clustering two or more sequence regions of the plurality of sequence regions to generate a plurality of clusters is based on at least 99% sequence identity.

In Embodiment 30, the subject matter of Embodiments 18-29 includes, wherein clustering two or more sequence regions of the plurality of sequence regions to generate a plurality of clusters is based on at least 98% sequence identity.

In Embodiment 31, the subject matter of Embodiments 18-30 includes, wherein merging two or more clusters of the plurality of clusters comprises iteratively merging two or more clusters of the plurality of clusters into one or more modified clusters.

In Embodiment 32, the subject matter of Embodiment 31 includes, wherein each iterative merging of two or more clusters of the plurality of clusters is based on aligning a representative sequence region from each cluster using a different sequence identity for each iteration.

In Embodiment 33, the subject matter of Embodiments 31-32 includes, wherein iteratively merging two or more clusters of the plurality of clusters is performed until a predetermined number clusters is generated.

In Embodiment 34, the subject matter of Embodiment 33 includes, wherein the predetermined number of clusters is 1.

In Embodiment 35, the subject matter of Embodiments 18-34 includes, wherein the genotype of the candidate ITR sequence is identical to a wild type ITR sequence or an engineered ITR sequence.

In Embodiment 36, the subject matter of Embodiments 18-35 includes, disposing of any plasmids related to the plurality of plasmids.

Embodiment 37 is a method, comprising: sequencing genomes of a plurality of plasmids to obtain a plurality of plasmid genome sequences; receiving a specification of a fixed flanking sequence marker; extracting, from each plasmid genome sequence, based on the presence of the fixed flanking sequence markers in that plasmid genome sequence, a plurality of sequence regions, wherein each sequence region is within the fixed flanking sequence markers and comprises a candidate inverted terminal repeat (ITR) sequence; clustering, based on sequence identity, two or more sequence regions of the plurality of sequence regions to generate a plurality of clusters; merging, based on an alignment between their corresponding sequence regions, two or more clusters of the plurality of clusters; and when a single cluster remains after said merging, identifying, based on a local alignment, a genotype of a candidate ITR sequence of a representative sequence region of the single cluster.

In Embodiment 38, the subject matter of Embodiment 37 includes, wherein sequencing the plurality of plasmids comprises sequencing via long read sequencing or circular consensus sequencing.

In Embodiment 39, the subject matter of Embodiments 37-38 includes, wherein the fixed flanking sequence marker comprises a sequence of at least 15 nucleotides.

In Embodiment 40, the subject matter of Embodiments 37-39 includes, wherein the fixed flanking sequence marker comprises at least a portion of a transgene to be delivered by an AAV vector.

In Embodiment 41, the subject matter of Embodiments 37-40 includes, wherein extracting the plurality of sequence regions comprises: locating, in the plasmid genome sequence, the fixed flanking sequence marker; and extracting the sequence region from the fixed flanking sequence marker in a 5' to 3' direction relative to the orientation of the fixed flanking sequence marker.

In Embodiment 42, the subject matter of Embodiments 37-41 includes, wherein extracting the plurality of sequence regions comprises: locating, in the plasmid genome sequence, the fixed flanking sequence marker; and extracting the sequence region from the fixed flanking sequence marker in a 3' to 5' direction relative to the orientation of the fixed flanking sequence marker.

In Embodiment 43, the subject matter of Embodiments 37-42 includes, wherein extracting the plurality of sequence regions comprises: locating, in the plasmid genome sequence, a plurality of fixed flanking sequence markers; and extracting the sequence region between the plurality of fixed flanking sequence markers.

In Embodiment 44, the subject matter of Embodiments 37-43 includes, for each sequence region of the plurality of sequence regions: determining a length of that sequence region; and excluding that sequence region from the clustering step if its length is above a first threshold or below a second threshold.

In Embodiment 45, the subject matter of Embodiment 44 includes, wherein the first threshold is about 700 base pairs long and the second threshold is about 150 base pairs long.

In Embodiment 46, the subject matter of Embodiments 37-45 includes, generating, based on sequence regions associated with clusters comprising two or more sequence regions, a database of ITR genotypes; and manufacturing recombinant AAV vectors based on the database of ITR genotypes.

In Embodiment 47, the subject matter of Embodiments 37-46 includes, wherein clustering two or more sequence regions of the plurality of sequence regions to generate a plurality of clusters is based on perfect sequence identity.

In Embodiment 48, the subject matter of Embodiments 37-47 includes, wherein clustering two or more sequence regions of the plurality of sequence regions to generate a plurality of clusters is based on at least 99% sequence identity.

In Embodiment 49, the subject matter of Embodiments 37-48 includes, wherein clustering two or more sequence regions of the plurality of sequence regions to generate a plurality of clusters is based on at least 98% sequence identity.

In Embodiment 50, the subject matter of Embodiments 37-49 includes, wherein merging two or more clusters of the plurality of clusters comprises iteratively merging two or more clusters of the plurality of clusters into one or more modified clusters.

In Embodiment 51, the subject matter of Embodiment 50 includes, wherein each iterative merging of two or more clusters of the plurality of clusters is based on aligning a representative sequence region from each cluster using a different sequence identity for each iteration.

In Embodiment 52, the subject matter of Embodiments 50-51 includes, wherein iteratively merging two or more clusters of the plurality of clusters is performed until a predetermined number clusters is generated.

In Embodiment 53, the subject matter of Embodiment 52 includes, wherein the predetermined number of clusters is 1.

In Embodiment 54, the subject matter of Embodiments 37-53 includes, wherein the genotype of the candidate ITR sequence is identical to a wild type ITR sequence or an engineered ITR sequence.

In Embodiment 55, the subject matter of Embodiments 37-54 includes, manufacturing, based on the genotype of the candidate ITR sequence being identical to a wild type ITR sequence or an engineered ITR sequence, a plurality of AAV vectors using plasmids having ITR sequences with the genotype of the candidate ITR sequence.

In Embodiment 56, the subject matter of Embodiment 55 includes, packaging, based on the genotype of the candidate ITR sequence being identical to a wild type ITR sequence or an engineered ITR sequence, the plurality of AAV vectors for distribution.

In Embodiment 57, the subject matter of Embodiments 55-56 includes, administering to a human subject a therapeutically effective amount of the manufactured recombinant AAV vectors.

Embodiment 58 is a method, comprising: sequencing Adeno-associated virus (AAV) vector genomes, from a plurality of AAV vectors, to obtain a plurality of AAV vector genome sequences; receiving a specification of a fixed flanking sequence marker; extracting, from each AAV vector genome sequence of the plurality of AAV vectors, based on the presence of the fixed flanking sequence markers in that AAV vector genome sequence, a sequence region immediately to the left or immediately to the right of a fixed flanking sequence marker, wherein the sequence region comprises a candidate ITR sequence; clustering, based on perfect sequence identity, two or more sequence regions of the plurality of sequence regions to generate a plurality of clusters; merging, based on an alignment between their corresponding sequence regions, two or more clusters of the plurality of clusters; and deeming, based on two or more clusters remaining after the merging, the plurality of AAV vector genomes as unsuitable.

In Embodiment 59, the subject matter of Embodiment 58 includes, wherein sequencing the plurality of AAV genomes comprises sequencing via long read sequencing or circular consensus sequencing.

In Embodiment 60, the subject matter of Embodiments 58-59 includes, wherein the fixed flanking sequence marker comprises a sequence of at least 15 nucleotides.

In Embodiment 61, the subject matter of Embodiments 58-60 includes, wherein the fixed flanking sequence marker comprises at least a portion of a transgene to be delivered by the plurality of AAV vectors.

In Embodiment 62, the subject matter of Embodiments 58-61 includes, wherein extracting, from each AAV vector genome sequence of the plurality of AAV vectors, based on the presence of the fixed flanking sequence markers in that AAV vector genome sequence, a sequence region immediately to the left or immediately to the right of a fixed flanking sequence marker comprises: locating, in the AAV vector genome sequence, the fixed flanking sequence marker; and extracting the sequence region from the fixed flanking sequence marker in a 5' to 3' direction relative to the orientation of the fixed flanking sequence marker.

In Embodiment 63, the subject matter of Embodiments 58-62 includes, wherein extracting, from each AAV vector genome sequence of the plurality of AAV vectors, based on the presence of the fixed flanking sequence markers in that AAV vector genome sequence, a sequence region immediately to the left or immediately to the right of a fixed flanking sequence marker comprises: locating, in the AAV vector genome sequence, the fixed flanking sequence marker; and extracting the sequence region from the fixed flanking sequence marker in a 3' to 5' direction relative to the orientation of the fixed flanking sequence marker.

In Embodiment 64, the subject matter of Embodiments 58-63 includes, wherein extracting, from each AAV vector genome sequence of the plurality of AAV vectors, based on the presence of the fixed flanking sequence markers in that AAV vector genome sequence, a sequence region immediately to the left or immediately to the right of a fixed flanking sequence marker comprises: locating, in the AAV vector genome sequence, a plurality of fixed flanking sequence markers; and extracting the sequence region between the plurality of fixed flanking sequence markers.

In Embodiment 65, the subject matter of Embodiments 58-64 includes, for each sequence region of the plurality of sequence regions: determining a length of that sequence region; and excluding that sequence region from the clustering step if its length is above a first threshold or below a second threshold.

In Embodiment 66, the subject matter of Embodiment 65 includes, wherein the first threshold is about 700 base pairs long and the second threshold is about 150 base pairs long.

In Embodiment 67, the subject matter of Embodiments 58-66 includes, generating, based on sequence regions associated with clusters comprising two or more sequence regions, a database of AAV ITR genotypes.

In Embodiment 68, the subject matter of Embodiments 58-67 includes, wherein clustering two or more sequence regions of the plurality of sequence regions to generate a plurality of clusters is based on perfect sequence identity.

In Embodiment 69, the subject matter of Embodiments 58-68 includes, wherein clustering two or more sequence regions of the plurality of sequence regions to generate a plurality of clusters is based on at least 99% sequence identity.

In Embodiment 70, the subject matter of Embodiments 58-69 includes, wherein clustering two or more sequence regions of the plurality of sequence regions to generate a plurality of clusters is based on at least 98% sequence identity.

In Embodiment 71, the subject matter of Embodiments 58-70 includes, wherein merging two or more clusters of the plurality of clusters comprises iteratively merging two or more clusters of the plurality of clusters into one or more modified clusters.

In Embodiment 72, the subject matter of Embodiment 71 includes, wherein each iterative merging of two or more clusters of the plurality of clusters is based on aligning a representative sequence region from each cluster using a different sequence identity for each iteration.

In Embodiment 73, the subject matter of Embodiments 71-72 includes, wherein iteratively merging two or more clusters of the plurality of clusters is performed until a predetermined number clusters is generated.

In Embodiment 74, the subject matter of Embodiment 73 includes, wherein the predetermined number of clusters is 1.

In Embodiment 75, the subject matter of Embodiments 58-74 includes, wherein the genotype of the candidate ITR sequence is identical to a wild type AAV ITR sequence or an engineered AAV ITR sequence.

In Embodiment 76, the subject matter of Embodiments 58-75 includes, disposing of any AAV vectors related to the plurality of AAV vectors.

Embodiment 77 is a method, comprising: sequencing a plurality of Adeno-associated viral (AAV) vector genomes to obtain a plurality of AAV vector genome sequences; receiving a specification of a fixed flanking sequence marker; extracting, from each AAV vector genome sequence of the plurality of AAV vectors, based on the presence of the fixed flanking sequence markers in that AAV vector genome sequence, a sequence region immediately to the left or immediately to the right of a fixed flanking sequence marker, wherein the sequence region comprises a candidate ITR sequence; clustering, based on perfect sequence identity, two or more sequence regions of the plurality of sequence regions to generate a plurality of clusters; merging, based on an alignment between their corresponding sequence regions, two or more clusters of the plurality of clusters to generate a modified plurality of clusters; and when a single cluster remains after said merging, identifying, based on a local alignment, a genotype of a candidate ITR sequence of a representative sequence region of the single cluster.

In Embodiment 78, the subject matter of Embodiment 77 includes, wherein sequencing the plurality of AAV vector genomes comprises sequencing via long read sequencing or circular consensus sequencing.

In Embodiment 79, the subject matter of Embodiments 77-78 includes, wherein the fixed flanking sequence marker comprises a sequence of at least 15 nucleotides.

In Embodiment 80, the subject matter of Embodiment 79 includes, wherein the fixed flanking sequence marker comprises at least a portion of a transgene to be delivered by the plurality of AAV vectors.

In Embodiment 81, the subject matter of Embodiments 77-80 includes, wherein extracting, from each AAV vector genome sequence of the plurality of AAV vectors, based on the presence of the fixed flanking sequence markers in that AAV vector genome sequence, a sequence region immediately to the left or immediately to the right of a fixed flanking sequence marker comprises: locating, in the AAV vector genome sequence, the fixed flanking sequence marker; and extracting the sequence region from the fixed flanking sequence marker in a 5' to 3' direction relative to the orientation of the fixed flanking sequence marker.

In Embodiment 82, the subject matter of Embodiments 77-81 includes, wherein extracting, from each AAV vector genome sequence of the plurality of AAV vectors, based on the presence of the fixed flanking sequence markers in that AAV vector genome sequence, a sequence region immediately to the left or immediately to the right of a fixed flanking sequence marker comprises: locating, in the AAV vector genome sequence, the fixed flanking sequence marker; and extracting the sequence region from the fixed flanking sequence marker in a 3' to 5' direction relative to the orientation of the fixed flanking sequence marker.

In Embodiment 83, the subject matter of Embodiments 77-82 includes, wherein extracting, from each AAV vector genome sequence of the plurality of AAV vectors, based on the presence of the fixed flanking sequence markers in that AAV vector genome sequence, a sequence region immediately to the left or immediately to the right of a fixed flanking sequence marker comprises: locating, in the AAV vector genome sequence, a plurality of fixed flanking sequence markers; and extracting the sequence region between the plurality of fixed flanking sequence markers.

In Embodiment 84, the subject matter of Embodiments 77-83 includes, for each sequence region of the plurality of sequence regions: determining a length of that sequence region; and excluding that sequence region from the clustering step if its length is above a first threshold or below a second threshold.

In Embodiment 85, the subject matter of Embodiment 84 includes, wherein the first threshold is about 700 base pairs long and the second threshold is about 150 base pairs long.

In Embodiment 86, the subject matter of Embodiments 77-85 includes, generating, based on sequence regions associated with clusters comprising two or more sequence regions, a database of ITR genotypes; and manufacturing recombinant AAV vectors based on the database of ITR genotypes.

In Embodiment 87, the subject matter of Embodiments 77-86 includes, wherein clustering two or more sequence regions of the plurality of sequence regions to generate a plurality of clusters is based on perfect sequence identity.

In Embodiment 88, the subject matter of Embodiments 77-87 includes, wherein clustering two or more sequence regions of the plurality of sequence regions to generate a plurality of clusters is based on at least 99% sequence identity.

In Embodiment 89, the subject matter of Embodiments 77-88 includes, wherein clustering two or more sequence regions of the plurality of sequence regions to generate a plurality of clusters is based on at least 98% sequence identity.

In Embodiment 90, the subject matter of Embodiments 77-89 includes, wherein merging two or more clusters of the plurality of clusters comprises iteratively merging two or more clusters of the plurality of clusters into one or more modified clusters.

In Embodiment 91, the subject matter of Embodiment 90 includes, wherein each iterative merging of two or more clusters of the plurality of clusters is based on aligning a representative sequence region from each cluster using a different sequence identity for each iteration.

In Embodiment 92, the subject matter of Embodiments 90-91 includes, wherein iteratively merging two or more clusters of the plurality of clusters is performed until a predetermined number clusters is generated.

In Embodiment 93, the subject matter of Embodiment 92 includes, wherein the predetermined number of clusters is 1.

In Embodiment 94, the subject matter of Embodiments 77-93 includes, wherein the genotype of the candidate ITR sequence is identical to a wild type AAV ITR sequence or an engineered AAV ITR sequence.

In Embodiment 95, the subject matter of Embodiments 77-94 includes, manufacturing, based on the genotype of the candidate ITR sequence being identical to a wild type AAV ITR sequence or an engineered AAV ITR sequence, an additional plurality of AAV vectors using the same plasmids used to manufacture the plurality of AAV vectors.

In Embodiment 96, the subject matter of Embodiment 95 includes, packaging, based on the genotype of the candidate ITR sequence being identical to a wild type ITR sequence or an engineered ITR sequence, the plurality of AAV vectors for distribution.

In Embodiment 97, the subject matter of Embodiments 95-96 includes, administering to a human subject a therapeutically effective amount of the manufactured recombinant AAV vectors.

Embodiment 98 is a method of treating a subject in need thereof comprising: administering to the subject a therapeutically effective amount of an Adeno-associated virus (AAV) vector comprising a vector genome encapsulated by an AAV capsid, wherein the AAV genome comprises at least two AAV inverted terminal repeats (ITR), a nucleic acid sequence encoding a therapeutic, wherein a genotype of the at least two AAV ITRs is identical to a reference AAV ITR as determined based on the method of Embodiment 77.

Embodiment 99 is computer readable medium having processor-executable instructions embodiment thereon configured to cause an apparatus to perform any of the embodiments 1-98.

Embodiment 100 is an apparatus configured to to implement of any of Embodiments 1-98.

Embodiment 101 is a system to implement of any of Embodiments 1-98.

While specific configurations have been described, it is not intended that the scope be limited to the particular configurations set forth, as the configurations herein are intended in all respects to be possible configurations rather than restrictive.

Unless otherwise expressly stated, it is in no way intended that any method set forth herein be construed as requiring that its steps be performed in a specific order. Accordingly where a method claim does not actually recite an order to be followed by its steps or it is not otherwise specifically stated in the claims or descriptions that the steps are to be limited to a specific order, it is in no way intended that an order be inferred, in any respect. This holds for any possible non-express basis for interpretation, including: matters of logic with respect to arrangement of steps or operational flow; plain meaning derived from grammatical organization or punctuation; the number or type of configurations described in the specification.

It will be apparent to those skilled in the art that various modifications and variations may be made without departing from the scope or spirit. Other configurations will be apparent to those skilled in the art from consideration of the specification and practice described herein. It is intended that the specification and described configurations be considered as exemplary only, with a true scope and spirit being indicated by the following claims.

The invention claimed is:

1. A method of manufacturing comprising:

sequencing genomes of a plurality of plasmids to obtain a plurality of plasmid genome sequences;

receiving a specification of a fixed flanking sequence marker;

extracting, from each plasmid genome sequence, based on the presence of the fixed flanking sequence markers in the plasmid genome sequence, a plurality of sequence regions, wherein each sequence region is within the fixed flanking sequence markers and comprises a candidate inverted terminal repeat (ITR) sequence;

clustering, based on perfect sequence identity, two or more sequence regions of the plurality of sequence regions to generate a plurality of clusters;

merging, based on an alignment between their corresponding sequence regions, two or more clusters of the plurality of clusters;

when a single cluster remains, identifying, based on a local alignment, a genotype of a candidate ITR sequence of the single cluster; and manufacturing, based on the genotype of the candidate ITR sequence, a plurality of adeno-associated virus (AAV) vectors using plasmids having ITR sequences with the genotype of the candidate ITR sequence.

2. The method of claim 1, wherein:

sequencing the plurality of plasmids comprises sequencing via long read sequencing or circular consensus sequencing; and/or the fixed flanking sequence marker comprises:

a sequence of at least 15 nucleotides; and/or at least a portion of a transgene to be delivered by an AAV vector.

3. The method of claim 1, wherein extracting the plurality of sequence regions comprises:

locating, in the plasmid genome sequence, the fixed flanking sequence marker; and extracting the sequence region from the fixed flanking sequence marker in a 5' to 3' direction or in a 3' to 5' direction relative to the orientation of the fixed flanking sequence marker; or locating, in the plasmid genome sequence, a plurality of fixed flanking sequence markers; and extracting the sequence region between the plurality of fixed flanking sequence markers.

4. The method of claim 1, further comprising, for each sequence region of the plurality of sequence regions:

determining a length of that sequence region; and excluding that sequence region from the clustering step if its length is above a first threshold or below a second threshold; and optionally, wherein the first threshold is about 700 base pairs long and the second threshold is about 150 base pairs long.

5. The method of claim 1, further comprising:

generating, based on sequence regions associated with clusters comprising two or more sequence regions, a database of ITR genotypes; and manufacturing recombinant AAV vectors based on the database of ITR genotypes.

6. The method of claim 1, wherein merging two or more clusters of the plurality of clusters comprises iteratively merging two or more clusters of the plurality of clusters into one or more modified clusters.

7. The method of claim 6, wherein:

each iterative merging of two or more clusters of the plurality of clusters is based on aligning a representative sequence region from each cluster using a different sequence identity for each iteration; and/or iteratively merging two or more clusters of the plurality of clusters is performed until a predetermined number clusters is generated; and optionally, wherein the predetermined number of clusters is 1.

8. The method of claim 1, wherein the genotype of the candidate ITR sequence is identical to a wild type ITR sequence or an engineered ITR sequence; and/or further comprising:

packaging, based on the genotype of the candidate ITR sequence being identical to a wild type ITR sequence or an engineered ITR sequence, the plurality of AAV vectors for distribution; and/or administering to a human subject a therapeutically effective amount of the manufactured recombinant AAV vectors.

9. One or more non-transitory computer-readable media storing instructions that, when executed by one or more processors, cause the one or more processors to:

sequence genomes of a plurality of plasmids to obtain a plurality of plasmid genome sequences;

receive a specification of a fixed flanking sequence marker;

extract, from each plasmid genome sequence, based on the presence of the fixed flanking sequence markers in the plasmid genome sequence, a plurality of sequence regions, wherein each sequence region is within the fixed flanking sequence markers and comprises a candidate inverted terminal repeat (ITR) sequence;

cluster, based on perfect sequence identity, two or more sequence regions of the plurality of sequence regions to generate a plurality of clusters;

merge, based on an alignment between their corresponding sequence regions, two or more clusters of the plurality of clusters;

when a single cluster remains, identifying, based on a local alignment, a genotype of a candidate ITR sequence of the single cluster; and cause, based on the genotype of the candidate ITR sequence, manufacture of a plurality of AAV vectors using plasmids having ITR sequences with the genotype of the candidate ITR sequence.

10. The one or more non-transitory computer-readable media of claim 9, wherein:

the instructions that cause the one or more processors to sequence the plurality of plasmids further comprises instructions that cause the one or more processors to sequence via long read sequencing or circular consensus sequencing; and/or the fixed flanking sequence marker comprises:

a sequence of at least 15 nucleotides; and/or at least a portion of a transgene to be delivered by an AAV vector.

11. The one or more non-transitory computer-readable media of claim 9, wherein the instructions that cause the one or more processors to extract the plurality of sequence regions further comprise instructions that cause the one or more processors to:

locate, in the plasmid genome sequence, the fixed flanking sequence marker; and extract the sequence region from the fixed flanking sequence marker in a 5' to 3' direction or in a 3' to 5' direction relative to the orientation of the fixed flanking sequence marker; or locate, in the plasmid genome sequence, a plurality of fixed flanking sequence markers; and extract the sequence region between the plurality of fixed flanking sequence markers.

12. The one or more non-transitory computer-readable media of claim 9, wherein, for each sequence region of the plurality of sequence regions, the instructions further cause the one or more processors to:

determine a length of that sequence region; and exclude that sequence region from the clustering step if its length is above a first threshold or below a second threshold; and optionally, wherein the first threshold is about 700 base pairs long and the second threshold is about 150 base pairs long.

13. The one or more non-transitory computer-readable media of claim 9, wherein the instructions further cause the one or more processors to:

generate, based on sequence regions associated with clusters comprising two or more sequence regions, a database of ITR genotypes; and cause manufacture of recombinant AAV vectors based on the database of ITR genotypes.

14. The one or more non-transitory computer-readable media of claim 9, wherein the instructions that cause the one or more processors to merge two or more clusters of the plurality of clusters further comprises instructions that cause the one or more processors to iteratively merge two or more clusters of the plurality of clusters into one or more modified clusters.

15. The one or more non-transitory computer-readable media of claim 14:

wherein the instructions that cause the one or more processors to perform each iterative merge of two or more clusters of the plurality of clusters is based on the one or more processors executing the instructions to align a representative sequence region from each cluster using a different sequence identity for each iteration; and/or iteratively merge two or more clusters of the plurality of clusters is performed until a predetermined number clusters are generated; and optionally, wherein the predetermined number of clusters is 1.

16. The one or more non-transitory computer-readable media of claim 9, wherein the genotype of the candidate ITR sequence is identical to a wild type ITR sequence or an engineered ITR sequence; and/or wherein the instructions further cause the one or more processors to:

package, based on the genotype of the candidate ITR sequence being identical to a wild type ITR sequence or an engineered ITR sequence, the plurality of AAV vectors for distribution; and/or cause administration of a therapeutically effective amount of the manufactured recombinant AAV vectors to a human subject.

17. An apparatus, comprising:

one or more processors; and a memory storing processor-executable instructions that, when executed by the one or more processors, cause the apparatus to:

sequence genomes of a plurality of plasmids to obtain a plurality of plasmid genome sequences;

receive a specification of a fixed flanking sequence marker;

extract, from each plasmid genome sequence, based on the presence of the fixed flanking sequence markers in the plasmid genome sequence, a plurality of sequence regions, wherein each sequence region is within the fixed flanking sequence markers and comprises a candidate inverted terminal repeat (ITR) sequence;

cluster, based on perfect sequence identity, two or more sequence regions of the plurality of sequence regions to generate a plurality of clusters;

merge, based on an alignment between their corresponding sequence regions, two or more clusters of the plurality of clusters;

when a single cluster remains, identifying, based on a local alignment, a genotype of a candidate ITR sequence of the single cluster; and cause, based on the genotype of the candidate ITR sequence, manufacture of a plurality of AAV vectors using plasmids having ITR sequences with the genotype of the candidate ITR sequence.

18. The apparatus of claim 17, wherein:

the instructions that cause the apparatus to sequence the plurality of plasmids further comprises instructions that cause the apparatus to sequence via long read sequencing or circular consensus sequencing; and/or the fixed flanking sequence marker comprises:

a sequence of at least 15 nucleotides; and/or at least a portion of a transgene to be delivered by an AAV vector.

19. The apparatus of claim 17, wherein the instructions that cause the apparatus to extract the plurality of sequence regions further comprise instructions that cause the apparatus to:

locate, in the plasmid genome sequence, the fixed flanking sequence marker; and extract the sequence region from the fixed flanking sequence marker in a 5' to 3' direction or in a 3' to 5' direction relative to the orientation of the fixed flanking sequence marker; or locate, in the plasmid genome sequence, a plurality of fixed flanking sequence markers; and extract the sequence region between the plurality of fixed flanking sequence markers.

20. The apparatus of claim 17, wherein, for each sequence region of the plurality of sequence regions, the instructions further cause the apparatus to:

determine a length of that sequence region; and exclude that sequence region from the clustering step if its length is above a first threshold or below a second threshold; and optionally, wherein the first threshold is about 700 base pairs long and the second threshold is about 150 base pairs long.

21. The apparatus of claim 17, wherein the instructions further cause the apparatus to:

generate, based on sequence regions associated with clusters comprising two or more sequence regions, a database of ITR genotypes; and cause manufacture of recombinant AAV vectors based on the database of ITR genotypes.

22. The apparatus of claim 17, wherein the instructions that cause the apparatus to merge two or more clusters of the plurality of clusters further comprises instructions that cause the apparatus to iteratively merge two or more clusters of the plurality of clusters into one or more modified clusters.

23. The apparatus of claim 22:

wherein the instructions that cause the apparatus to perform each iterative merge of two or more clusters of the plurality of clusters is based on the one or more processors executing the instructions to cause the apparatus to align a representative sequence region from each cluster using a different sequence identity for each iteration; and/or iteratively merge two or more clusters of the plurality of clusters is performed until a predetermined number clusters are generated; and optionally, wherein the predetermined number of clusters is 1.

24. The apparatus of claim 17, wherein the genotype of the candidate ITR sequence is identical to a wild type ITR sequence or an engineered ITR sequence.

25. The apparatus of claim 17, wherein the instructions further cause the apparatus to:

package, based on the genotype of the candidate ITR sequence being identical to a wild type ITR sequence or an engineered ITR sequence, the plurality of AAV vectors for distribution; and/or cause administration of a therapeutically effective amount of the manufactured recombinant AAV vectors to a human subject.

* * * * *